United States Patent
Kim et al.

(10) Patent No.: US 10,357,223 B2
(45) Date of Patent: Jul. 23, 2019

(54) METHOD AND APPARATUS TO DETECT LIPID CONTENTS IN TISSUES USING ULTRASOUND

(71) Applicant: University of Pittsburgh—Of the Commonwealth System of Higher Education, Pittsburgh, PA (US)

(72) Inventors: Kang Kim, Pittsburgh, PA (US); Ahmed M. Mahmoud, Giza (EG); Debaditya Dutta, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 378 days.

(21) Appl. No.: 14/409,378

(22) PCT Filed: Jul. 3, 2013

(86) PCT No.: PCT/US2013/049342
§ 371 (c)(1),
(2) Date: Dec. 18, 2014

(87) PCT Pub. No.: WO2014/008408
PCT Pub. Date: Jan. 9, 2014

(65) Prior Publication Data
US 2015/0327835 A1    Nov. 19, 2015

Related U.S. Application Data

(60) Provisional application No. 61/667,807, filed on Jul. 3, 2012, provisional application No. 62/831,072, filed on Jun. 4, 2013.

(51) Int. Cl.
*A61B 8/00* (2006.01)
*A61B 8/08* (2006.01)
(Continued)

(52) U.S. Cl.
CPC ............. *A61B 8/08* (2013.01); *A61B 5/0095* (2013.01); *A61B 5/4872* (2013.01); *A61B 8/48* (2013.01);
(Continued)

(58) Field of Classification Search
CPC ......... A61B 5/4869; A61B 8/00; A61B 18/20; A61B 5/01; A61B 8/5223; A61B 2017/00084; A61B 2017/00106
See application file for complete search history.

(56) References Cited

U.S. PATENT DOCUMENTS 5,635,344 A    6/1997    Garcia et al.
9,655,594 B2 *  5/2017    Oraevsky ............... A61B 8/587
(Continued)

FOREIGN PATENT DOCUMENTS

WO    WO 2011-062621    5/2011

*Primary Examiner* — Joel Lamprecht
(74) *Attorney, Agent, or Firm* — Klarquist Sparkman, LLP

(57) ABSTRACT

A method for quantifying an amount of fat contained in a liver or other tissue of a subject in vivo includes varying the temperature of a target area in a subject, imaging thermal strain of the target area using an ultrasound scanner, and quantifying the amount of fat in the targeted area based on the thermal strain imaging. In some embodiments, the thermal strain imaging is performed using high-resolution, phase-sensitive speckle tracking to differentiate between fat-based tissue and water-based tissue.

17 Claims, 44 Drawing Sheets

(51) Int. Cl.
  *A61B 5/00* (2006.01)
  *A61B 5/01* (2006.01)

(52) U.S. Cl.
  CPC ............ *A61B 8/485* (2013.01); *A61B 8/5223* (2013.01); *A61B 5/015* (2013.01); *A61B 8/4416* (2013.01); *A61B 8/543* (2013.01)

(56) References Cited

U.S. PATENT DOCUMENTS

| | | |
|---|---|---|
| 2001/0038845 A1 | 11/2001 | Williams |
| 2005/0175540 A1 | 8/2005 | Oraevsky et al. |
| 2006/0166360 A1 | 7/2006 | Berthiaume et al. |
| 2009/0105588 A1* | 4/2009 | Emelianov ............ A61B 5/4869 600/438 |
| 2011/0319765 A1* | 12/2011 | Gertner ................... A61N 7/00 600/453 |

* cited by examiner

FIG. 6A
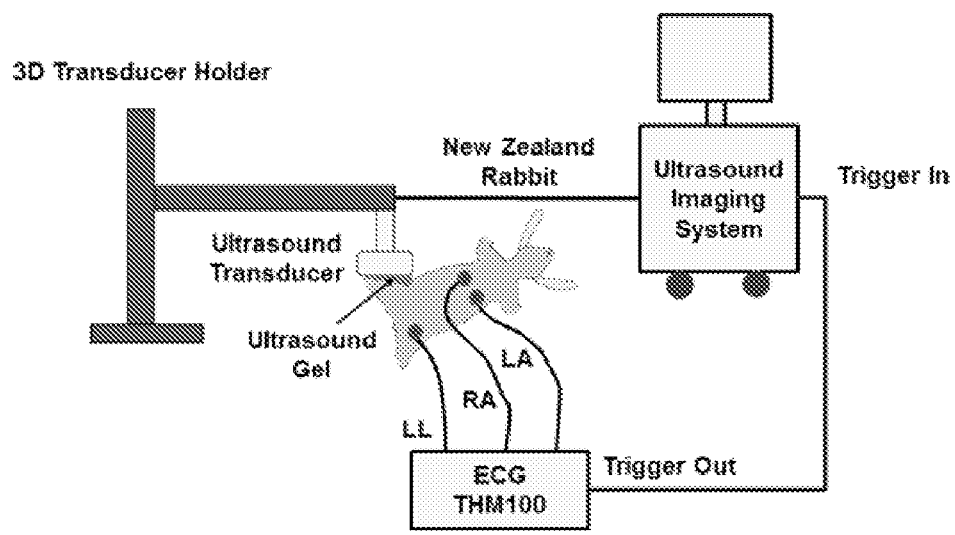
FIG. 6B  Average heart rate= 260 beats/minute
ECG trigger period= 230 ms
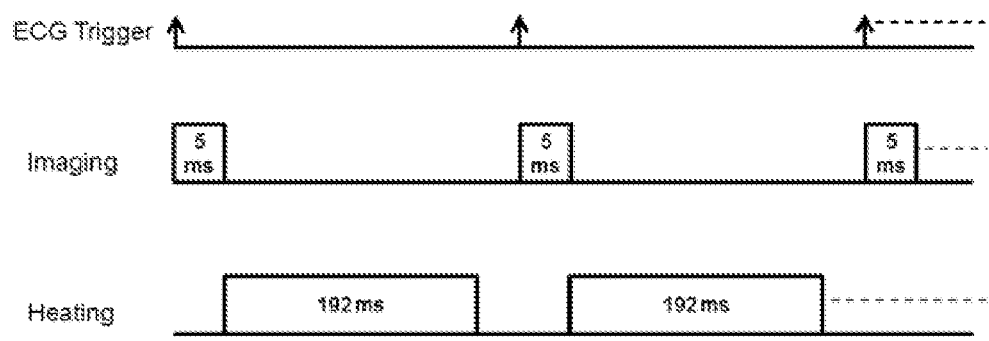

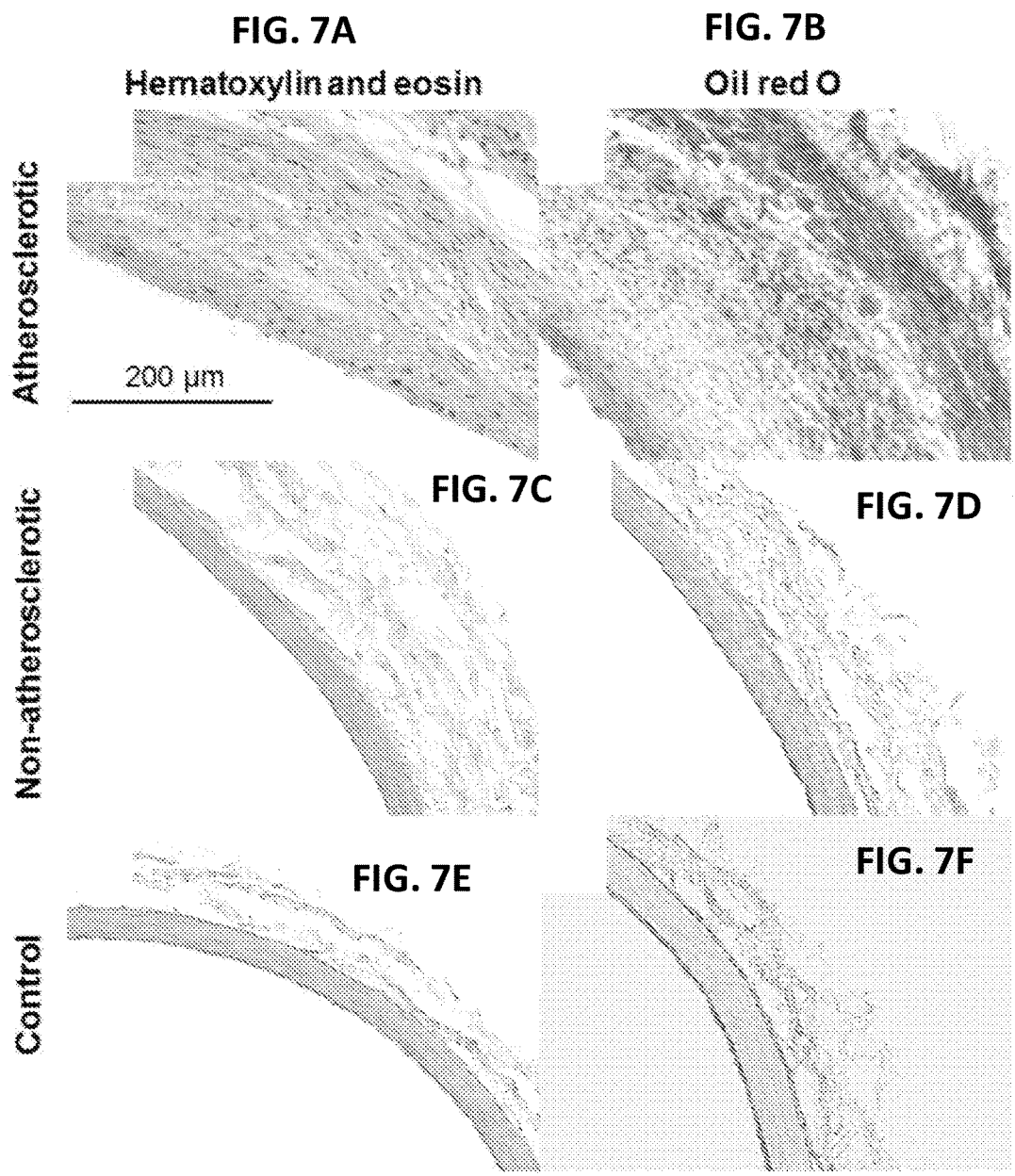

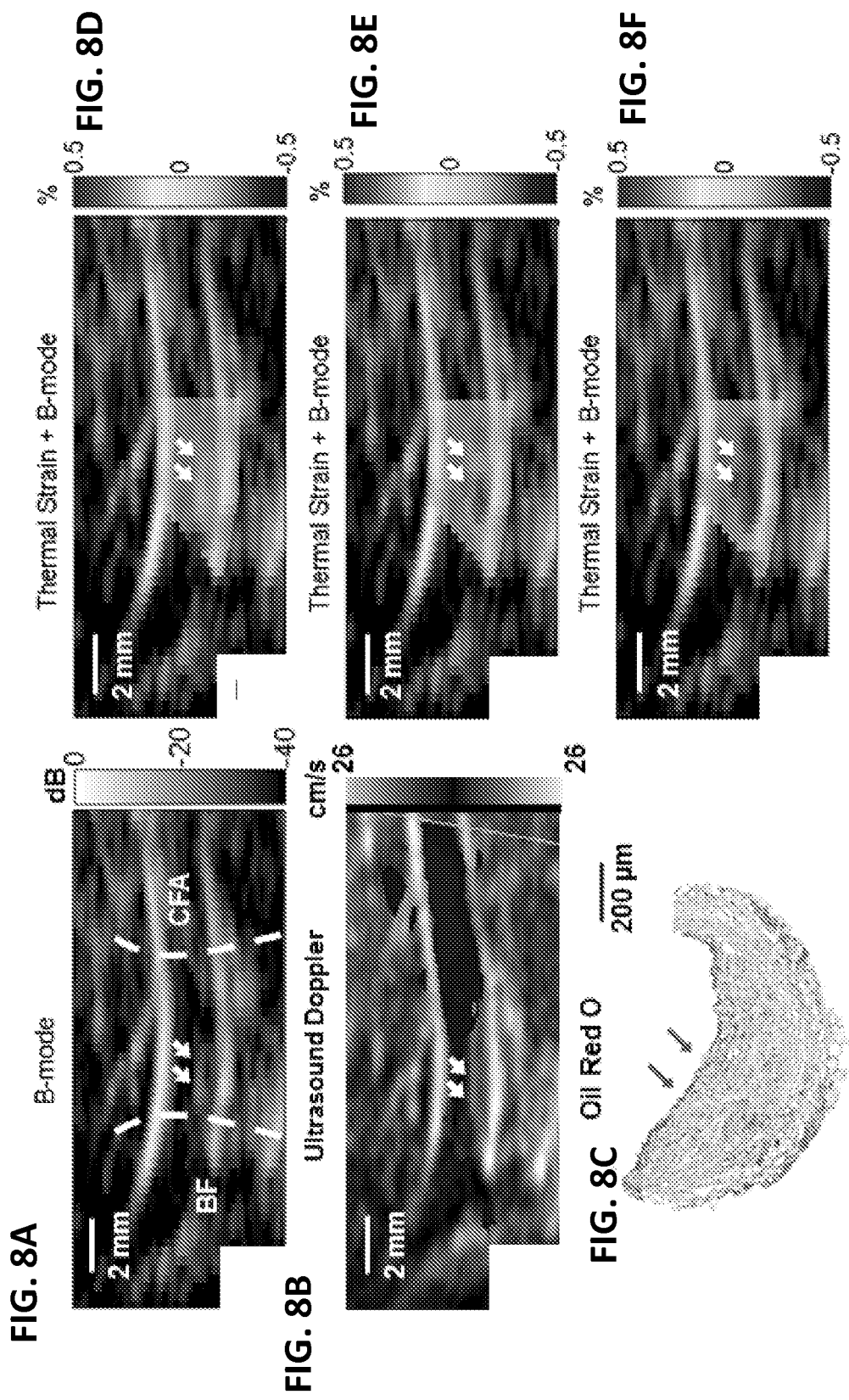

FIG. 9A B-mode
FIG. 9B
FIG. 9C
FIG. 9D Thermal Strain + B-mode
FIG. 9E
FIG. 9F
FIG. 9G Oil Red O
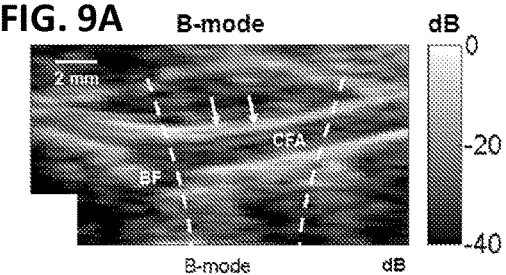
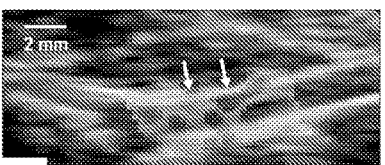
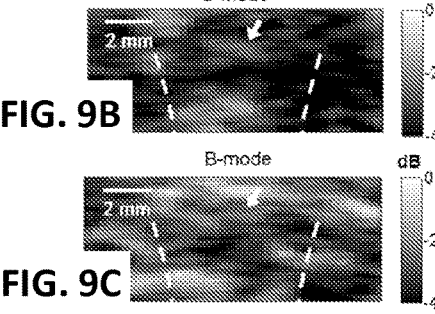
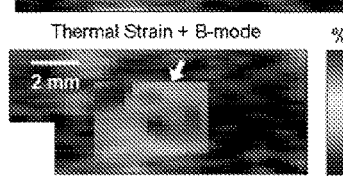
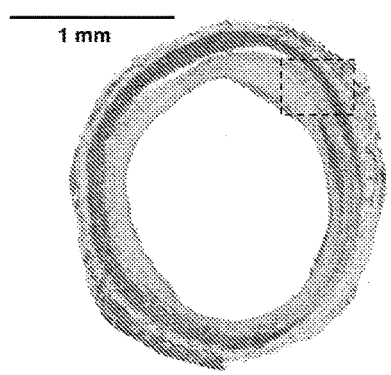

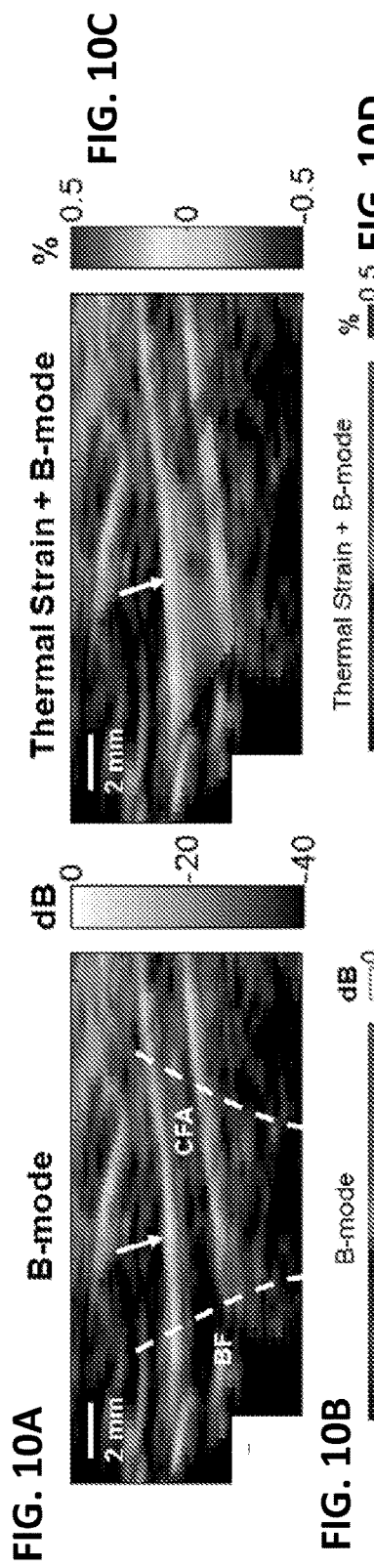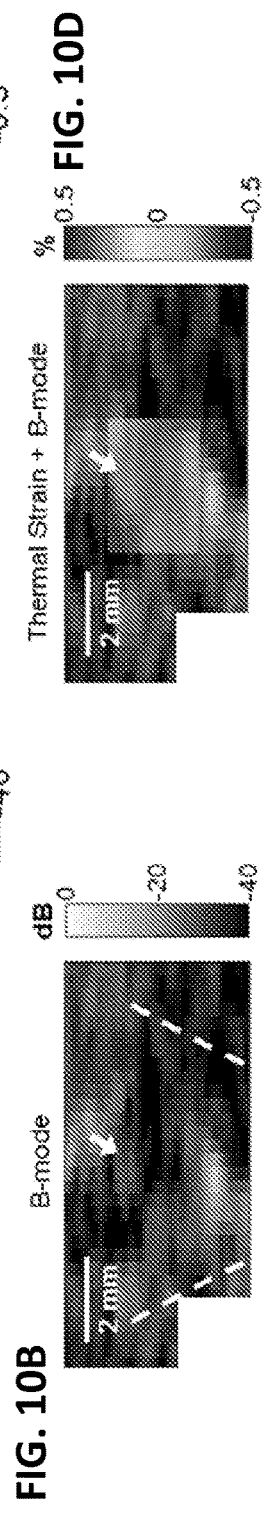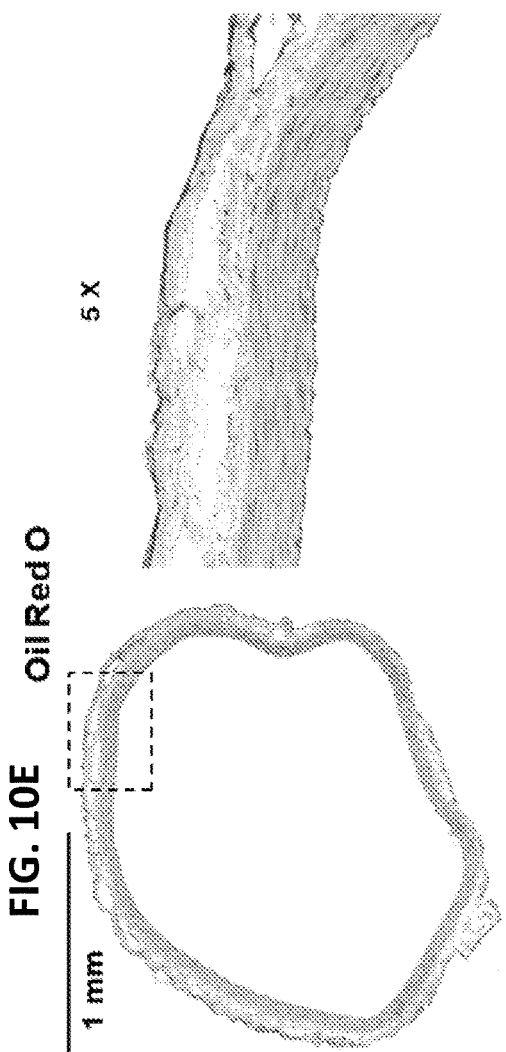
FIG. 10A  FIG. 10B  FIG. 10C  FIG. 10D  FIG. 10E

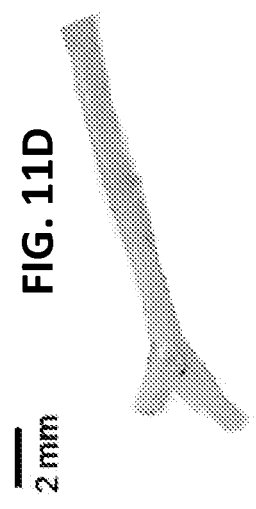
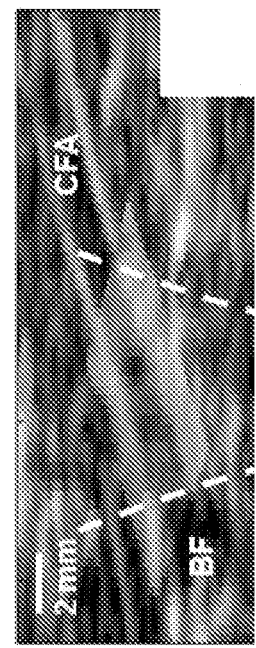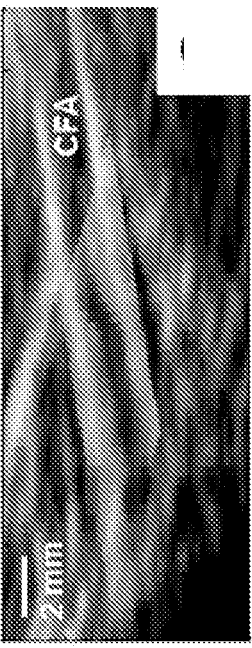
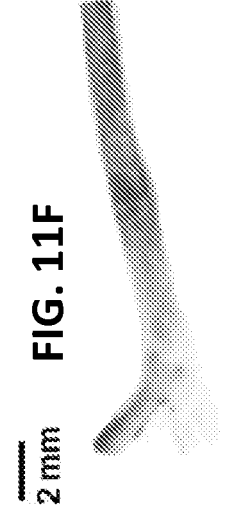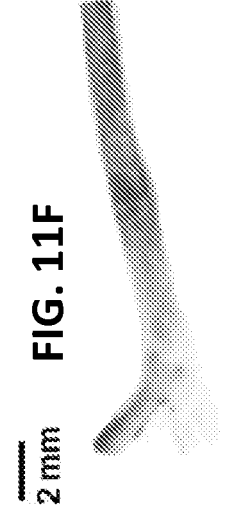
FIG. 11A · FIG. 11B · FIG. 11C · FIG. 11D · FIG. 11E · FIG. 11F

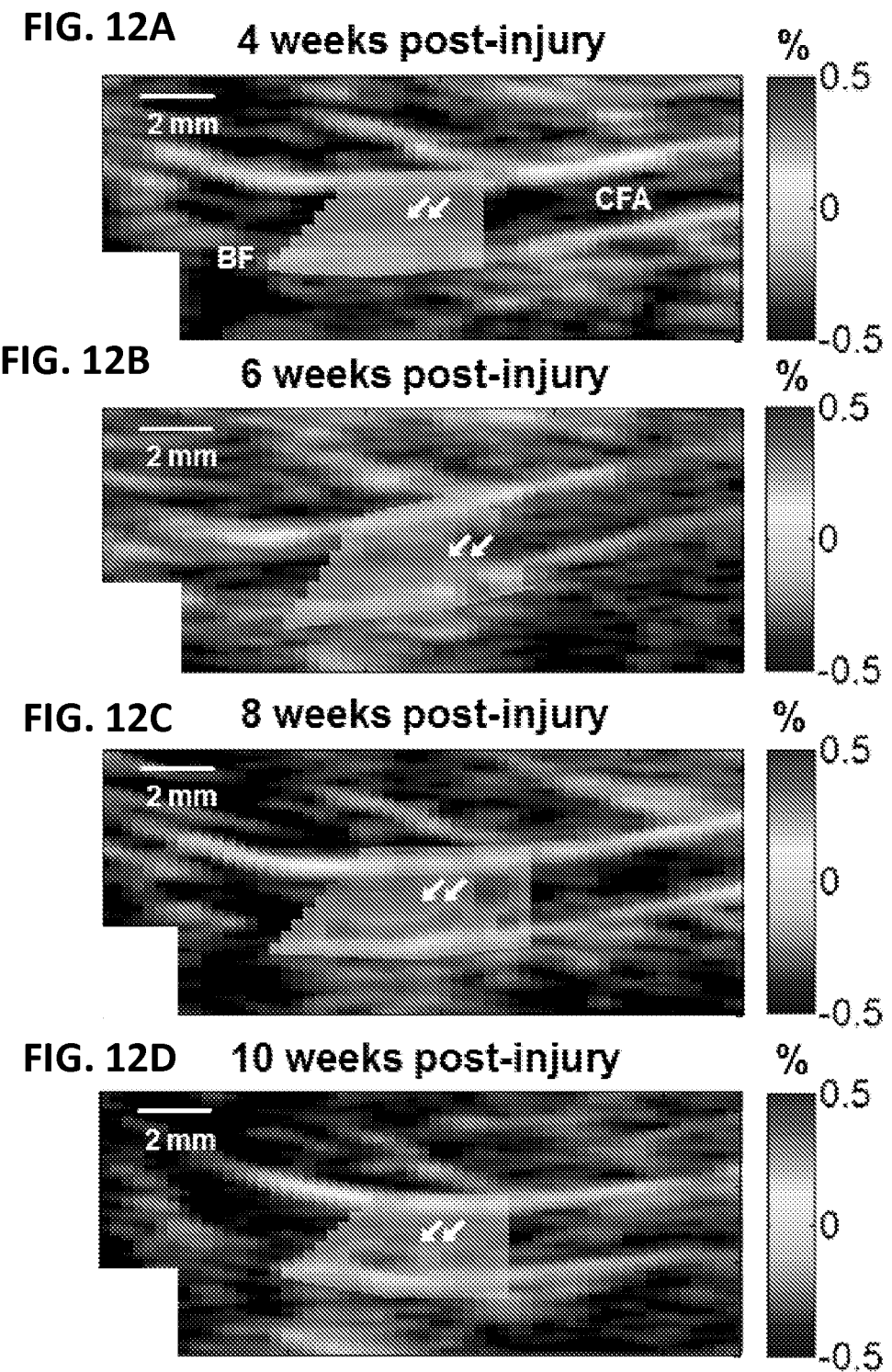

FIG. 13A
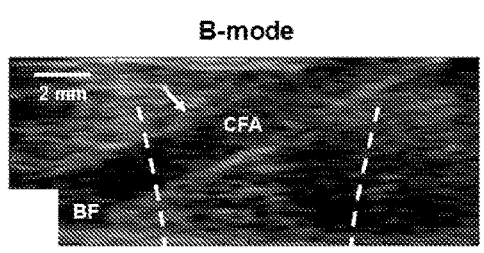
FIG. 13B
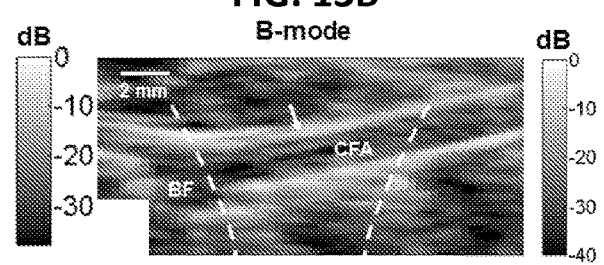
FIG. 13C
Oil Red O
FIG. 13D
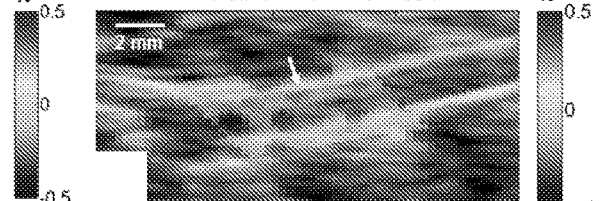
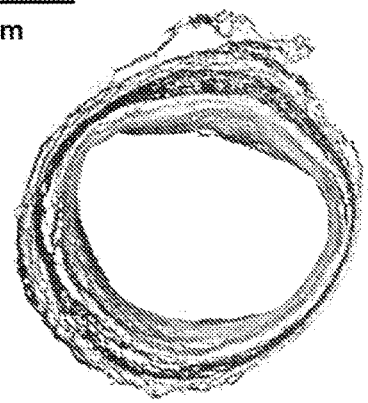
FIG. 13E

FIG. 15

| Thermal and mechanical properties of tissue used in the FE simulation. | | | | |
|---|---|---|---|---|
| Tissue | Thermal properties | | Mechanical properties | |
| | Specific heat (C [J/kg.K]) | Coeff. of sound speed change ($\alpha$) | Mass density ($\rho$ [kg/m$^3$]) | Stiffness [kPa] |
| Lipid | 2490 | -0.15% | 910 | Viscoelastic $G' = 5, G'' = 4$ |
| Fibrous cap | 3590 | 0.1% | 1050 | Neo-Hooekan $G=10$ |
| Vessel wall | 3590 | 0.1% | 1050 | Mooney-Rivlin $C_1 = 47, C_2 = 357$ |
| Muscle | 3590 | 0.1% | 1050 | Linear elastic $E = 100$ |
| Blood | 3600 | - | 1060 | Viscous $\eta = 0.003$ Pa.s |

FIG. 16

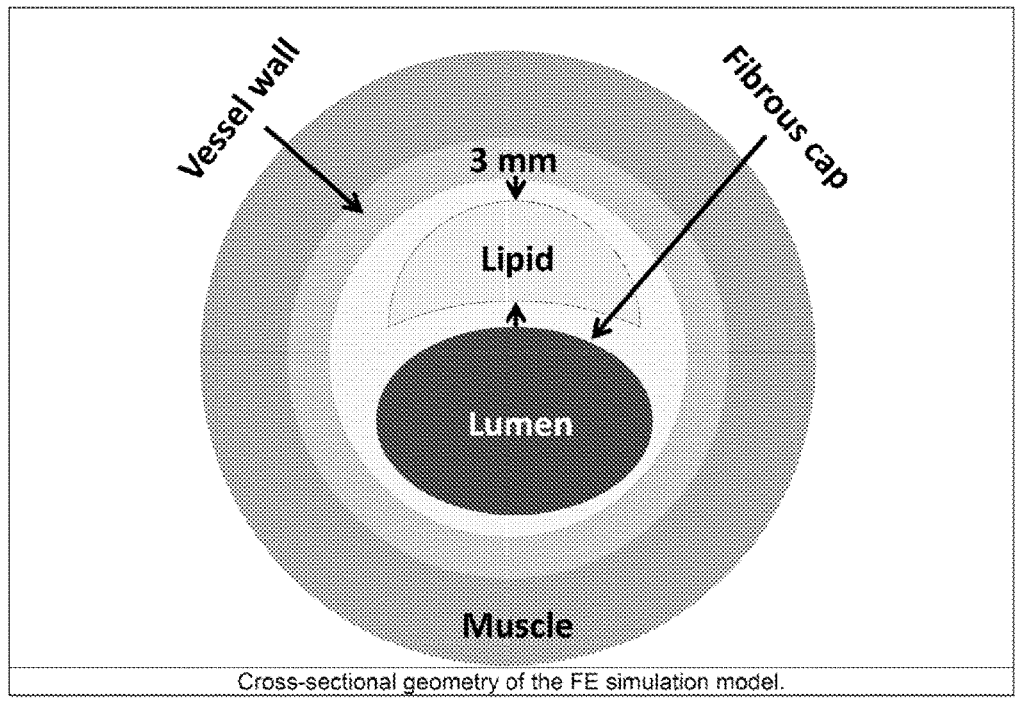

Cross-sectional geometry of the FE simulation model.

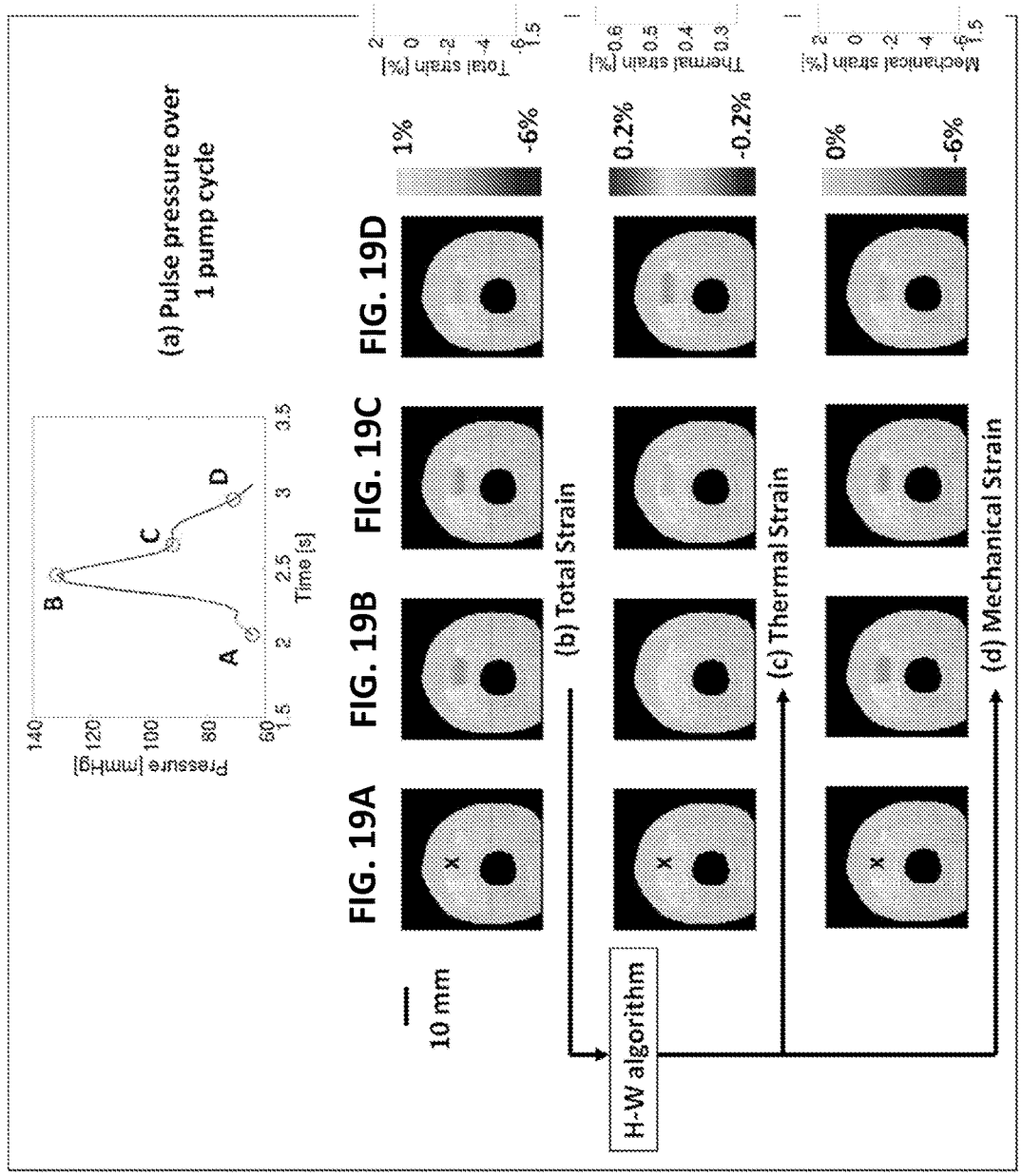

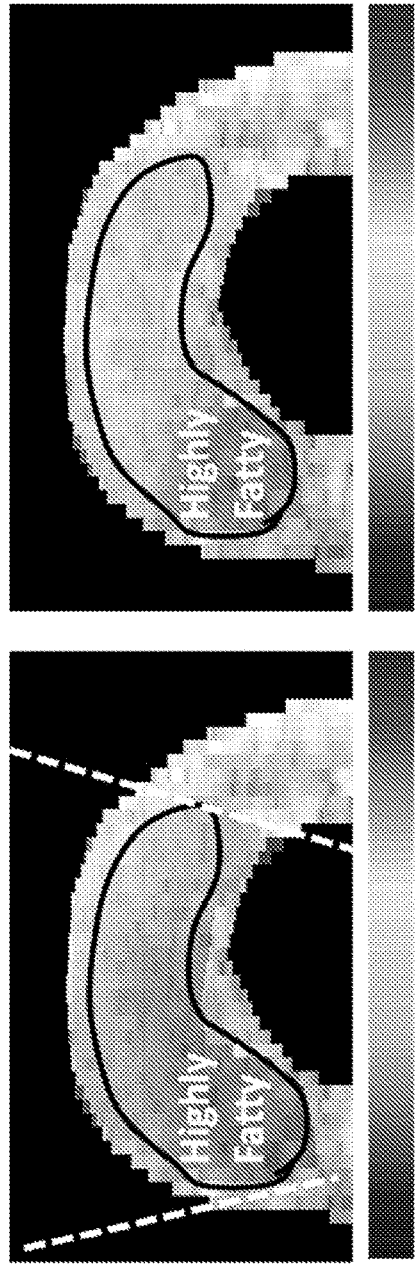
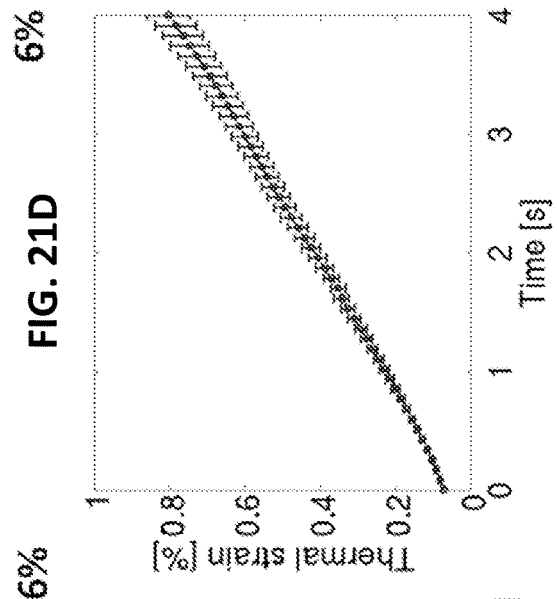
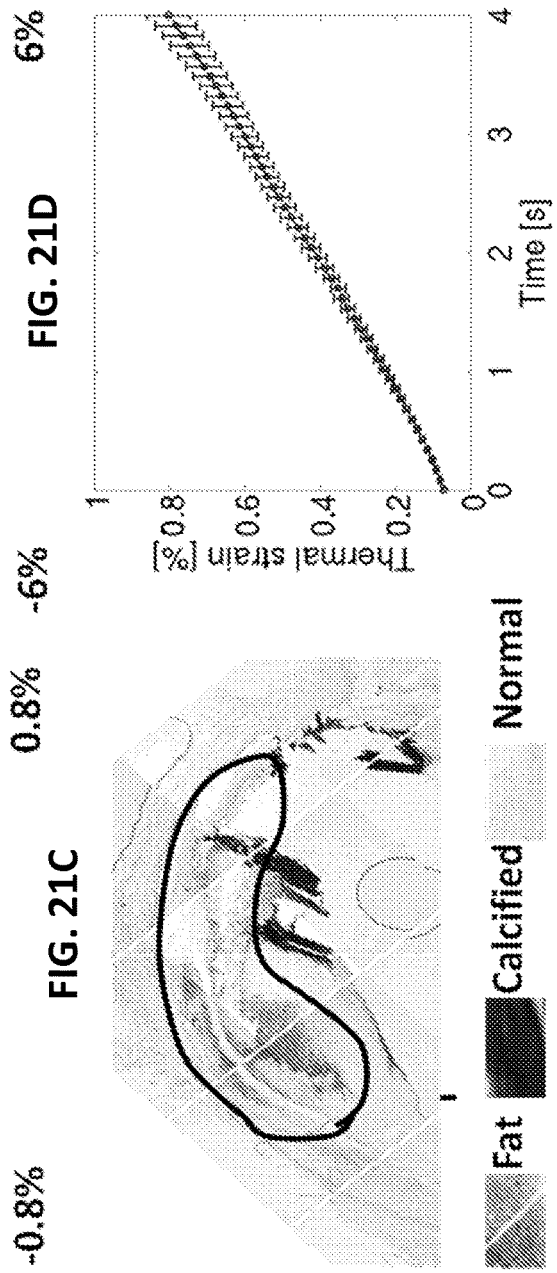
FIG. 21A   FIG. 21B   FIG. 21C   FIG. 21D
— 1 mm in (a), (b) and (c)

Output Power variation with Ag-Epoxy Thickness

FIG. 24

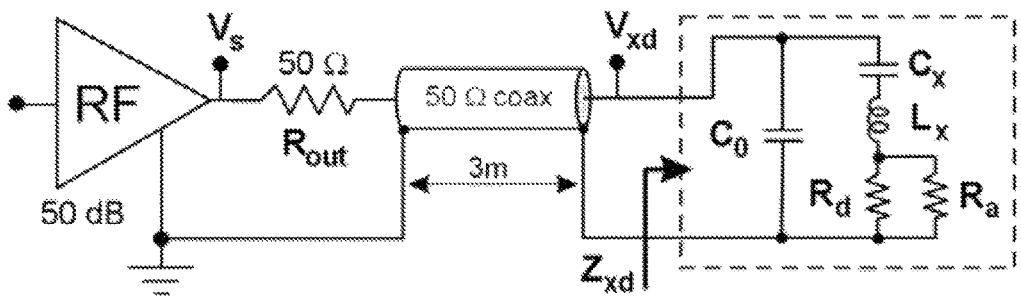

FIG. 25

TABLE I. Transducer Model Parameters

| Transducer (PZT - 5H) | | Matching Layer (Ag-Epoxy) | |
|---|---|---|---|
| diameter | 8.8 mm | thickness | 100 E-6 m (nominal) |
| frequency | 3.5 (flat) – 4.1(spher) MHz | $Z_{acous}$ | 5.14 E+6 kg s$^{-1}$ m$^{-2}$ |
| thickness | 0.57 mm | velocity | 1900 m/s |
| rel. dielectric | 1413 | absorption | 322 Np/m at 3.5 MHz |
| $Z_{acous}$ | 34.9 E+6 kg s$^{-1}$ m$^{-2}$ | Insulator (EpoTek 301) | |
| velocity | 4650 m/s | thickness | 25 - 40 E-6 m (nominal) |
| $k_t$ | 0.54 | $Z_{acous}$ | 2.85 E+6 kg s$^{-1}$ m$^{-2}$ |
| tan δ | 0.017 | velocity | 2680 m/s |
| absorption | 36 Np/m at 3.5 MHz | absorption | 150 Np/m at 3.5 MHz |
| Au thickness | 0.6 E-6 m | | |
| Transducer Tank Model Parameters | | RF Source Parameters | |
| $C_0$ | 1335 pF | $R_{out}$ | 50 Ohms |
| $C_x$ | 445 pF | $Z_{cable}$ | 50 Ohms (RG174) |
| $L_x$ | 4.5 uH | Length$_{cable}$ | 3.0 m |
| $Z_{xd}$ | 30.5 – j24 Ohms at 4 MHz | $R_{cable}$ | 0.4 Ohms/m (at 3.5MHz) |
| $S_{xd}$ | 17.5 kPa/V | $L_{cable}$ | 252 nH/m |
| $Z_w$ | 1.5 E+6 kg s$^{-1}$ m$^{-2}$ | $C_{cable}$ | 102 pF/m |
| $A_{xd}$ | 0.61 cm$^2$ | | |

FIG. 29

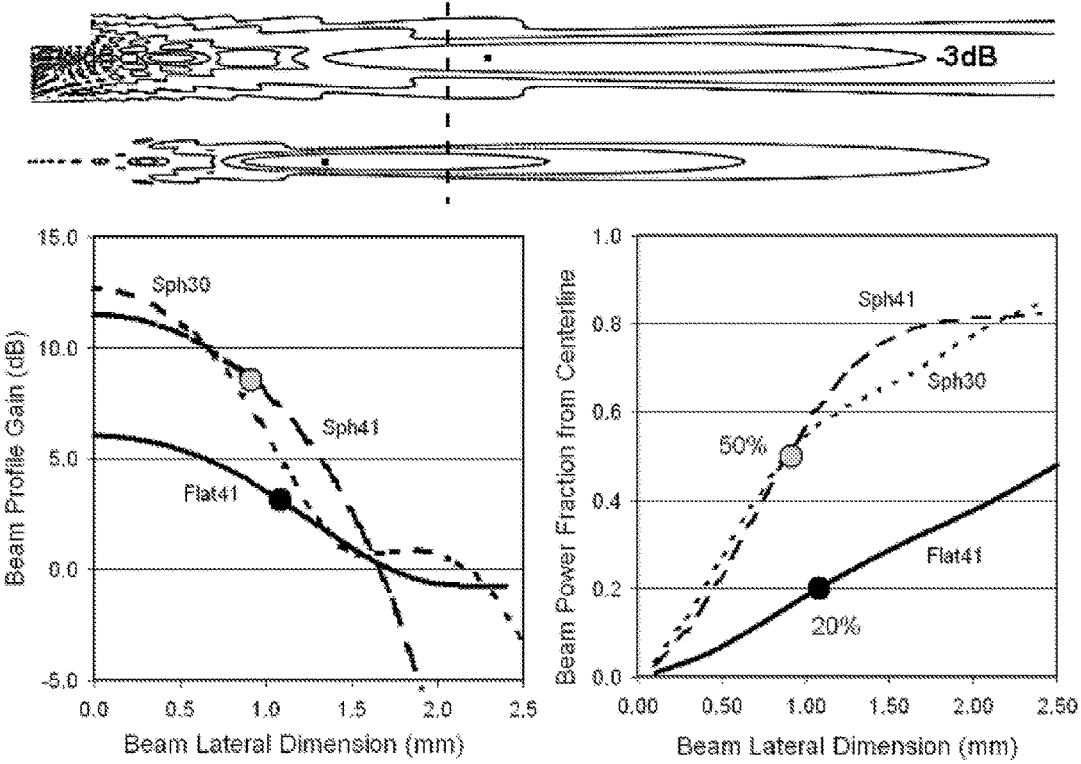

FIG. 30

Table II. Physical Properties of the Test Phantom

| Properties | Units | Gelatin Matrix | Rubber Target |
|---|---|---|---|
| Density | kg/m³ | 1050 [20] | 880 |
| Acoustic Speed | m/s | 1510 [20], [21] | 1387+/- 30 |
| Acoustic Attenuation | dB/cm/MHz | 0.3 [21] | 1.68 +/- 0.11 |
| Thermal Conductivity | W/mK | 0.6 [22], [21] | 0.04 |
| Heat Capacity | J/kgK | 4180 [22] | 600 |

Table III. In Vitro US-TSI Study Heating Array Excitation Parameters

| Parameter | Units | Flat Element Array | Spherical Element Array |
|---|---|---|---|
| Excitation Freq. | MHz | 3.55 | 4.0 |
| Duty Cycle | % | 56 | 56 |
| System Input Power | W | 25 | 25 |
| TSI Sequence Duration | seconds | 6.8 | 0.5 |

FIG. 32

TABLE IV. Metrics to produce 3C Tissue Rise in 2 seconds

| Aperture Type | At Aperture | At Target Plane Depth | | | |
|---|---|---|---|---|---|
| | $P_{pk}$ | $P_{pk}$ | MI | $I_{pk}$ | $I_{avg}$ |
| Flat | 445 kPa | 1.3 MPa | 0.7 | 56 W/cm$^2$ | 12.4 W/cm$^2$ |
| Spherical | 334 kPa | 1.1 MPa | 0.6 | 40 W/cm$^2$ | 11.8 W/cm$^2$ |

TABLE V. Heating Effectiveness for the Flat and Spherical Apertures

| Aperture | Focus Length | Beam Path | $Pw_{ap}$ | YZ Area | Efficiency Ratio |
|---|---|---|---|---|---|
| Flat | 44 mm | 41 mm | 24.1 W | 35 mm$^2$ | 1.45 |
| Spherical | 30 mm | 41 mm | 13.7 W | 31 mm$^2$ | 2.26 |

FIG. 33

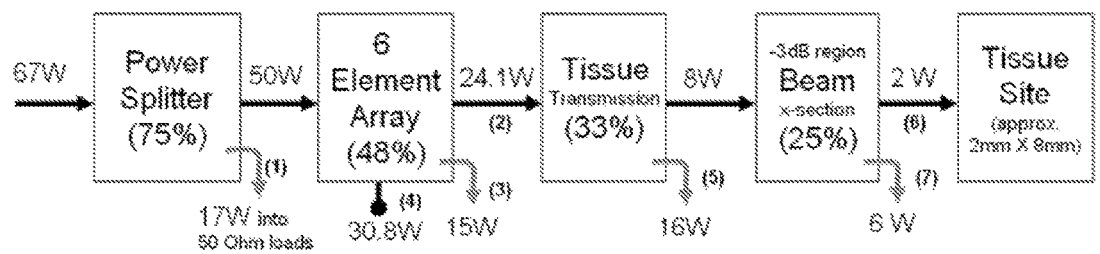

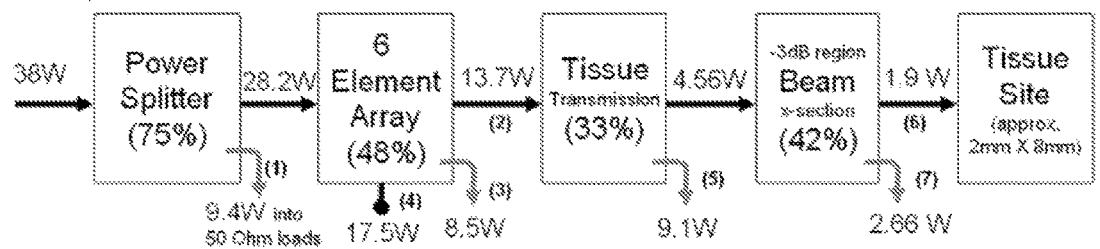

Heating pulse sequence

Imaging frame rate= 10 frames per seconds
(Vevo 2100)

B-mode

Thermal Strain + B-mode

Oil Red O Histology

B-mode

Thermal Strain + B-mode

Oil Red O Histology

Oil Red O Histology

B-mode

Thermal Strain + B-mode

Oil Red O Histology

FIG. 43
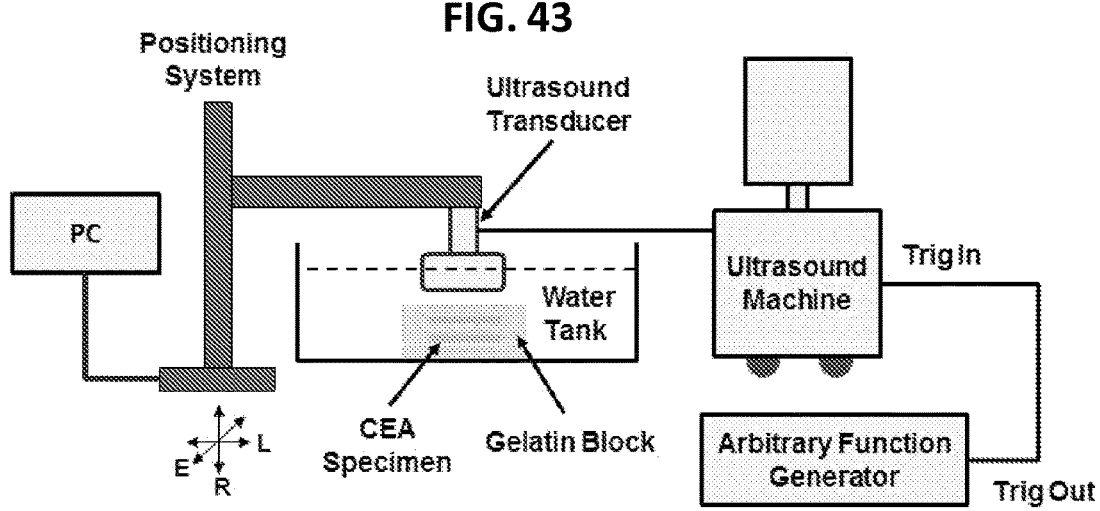
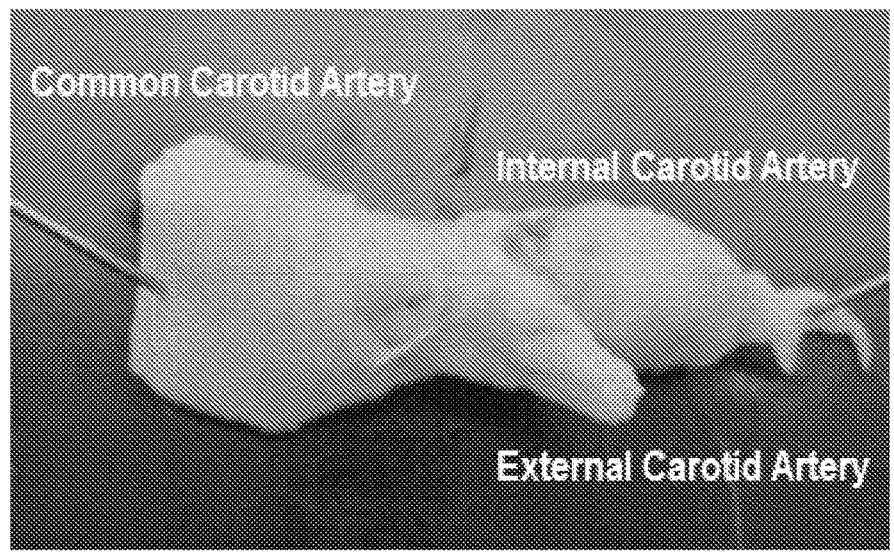

FIG. 46
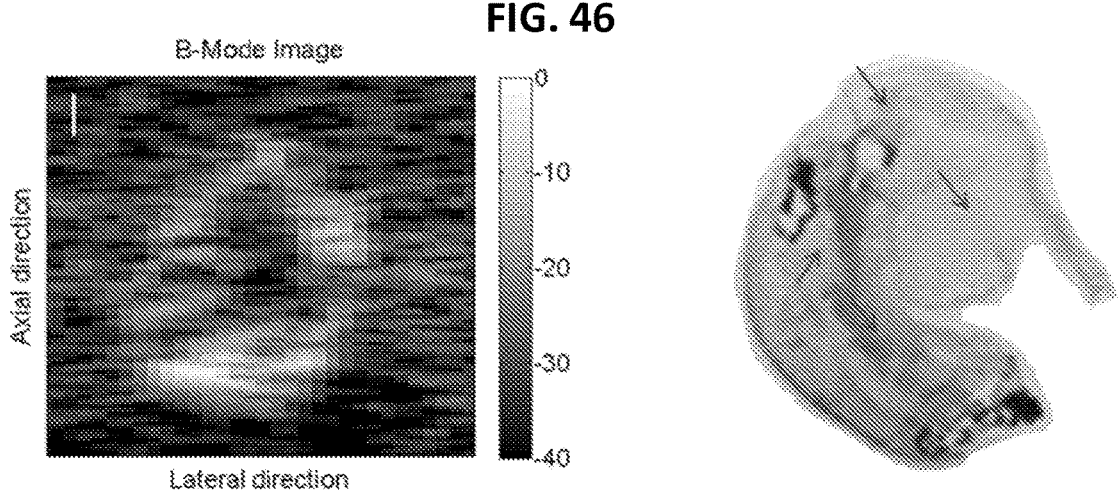
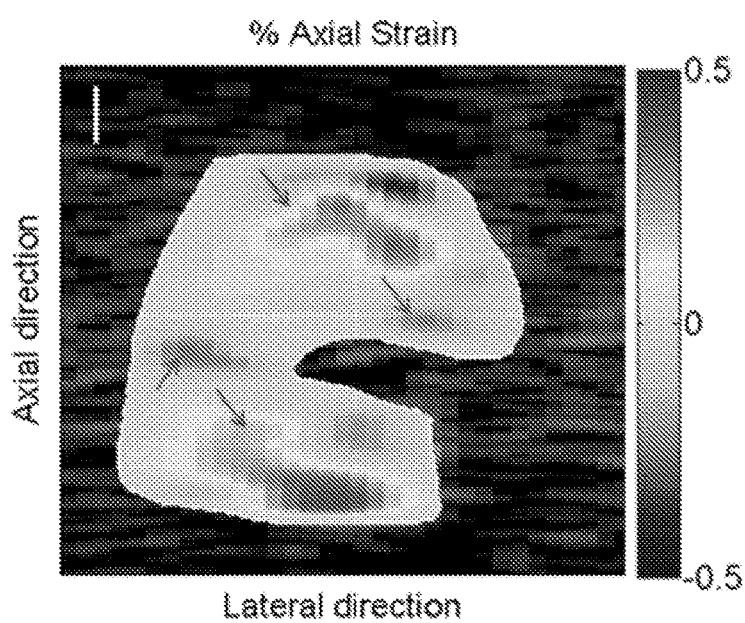

TSI pulse/imaging sequences and strain estimate flow chart

METHOD AND APPARATUS TO DETECT LIPID CONTENTS IN TISSUES USING ULTRASOUND

CROSS-REFERENCE TO RELATED APPLICATIONS

This is the U.S. National Stage of International Application No. PCT/US2013/049342, filed Jul. 3, 2013, which was published in English under PCT Article 21(2), which in turn claims the benefit of U.S. Provisional Application No. 61/667,807, which was filed on Jul. 3, 2012, and U.S. Provisional Application No. 61/831,072, which was filed on Jun. 4, 2013. The disclosures of U.S. Provisional Application No. 61/667,807 and U.S. Provisional Application No. 61/831,072 are incorporated herein by reference in their entirety.

ACKNOWLEDGMENT OF GOVERNMENT SUPPORT

This invention was made with government support under Grant Number HL098230-01A1 and Grant Number 1S10RR027383-01, both awarded by the National Institutes of Health. The government has certain rights in the invention.

FIELD

The present disclosure relates to methods and systems for detecting and quantifying accumulated fat-containing substances in tissue and organs of a subject.

BACKGROUND

The accumulation of various substances in tissues and organs of the body can be an indicator of certain conditions or diseases. For example, accumulation of fat-containing substances in the liver is an indicator of fatty liver disease, the most common cause of chronic liver disease in the United States. In addition, in the United States, the prevalence of nonalcoholic fatty liver disease (NAFLD) is increasing and has been estimated to affecting up to 30% of the general population. Although NAFLD was initially thought to be a benign condition, it has been increasingly recognized as a major cause of liver-related morbidity and mortality, capable of progressing to cirrhosis, liver failure, and hepatocellular carcinoma. With the rise of obesity and diabetes in United States, the prevalence of NAFLD is expected to continually increase.

Other accumulations in the body can be a significant indicator of other conditions and diseases as well. For example, accumulations of plaque in arteries can be an indicator of heart disease. Unfortunately, conventional techniques for detecting and quantifying substances in the liver, arties, and other tissue and organs of the body have many disadvantages. Many are invasive and/or expensive. For example, a needle biopsy is invasive and poorly suited as a diagnostic test in such a prevalent condition because of its expense and risks of complications. Available non-invasive imaging techniques, such as MR imaging and CT scans, are expensive and can have other disadvantages (e.g., exposure to ionizing radiation).

Accordingly, there is a need for improved systems and methods for assessing the condition of tissues and organs, and in particular, for detecting and quantifying the accumulation of these substances therein.

SUMMARY

The embodiments described herein relate to non-invasive imaging systems and methods for detecting and quantifying accumulations of fat-containing substances within tissues and organs of a subject. In some embodiments, the non-invasive imaging systems and methods can detect and quantify the accumulation of fat-containing substances within the liver of the subject.

A method for quantifying an amount of fat contained in a liver of a subject in vivo is provided. The method includes varying the temperature of a target area of a liver in a subject, imaging thermal strain of the target area using an ultrasound scanner, and quantifying the amount of fat in the targeted area based on the thermal strain imaging. In some embodiments, the thermal strain imaging comprises high-resolution, phase-sensitive speckle tracking to differentiate between fat-based tissue and water-based tissue. The variation of temperature can include varying the temperature by less than three degrees Celsius or, in some embodiments, less than two degrees Celsius. The variation of temperature can be performed over a period of less than about 10 minutes or, in some embodiments, less than about 5 minutes.

In some embodiments, the variation of temperature comprises heating the target area. The heating of the target area can include directing a near infrared heating source at the target area, with the near infrared heating source being coupled to the ultrasound scanner or separate from the ultrasound scanner. Alternatively, or in addition, the heating of the target area can include directing a second ultrasound device at the target area to heat the target area.

In some embodiments, the variation of temperature can include cooling the target area. The cooling of the target area can include applying a cooling pad to a surface adjacent the targeted tissue.

In other embodiments, a system is provided for identifying, in vivo, fat-containing tissue in a liver of a subject. The system can include an ultrasound imaging device for providing high-resolution, phase-sensitive speckle tracking and a temperature variation device for modulating the temperature of a target area of the liver of the subject between about three degrees Celsius. In some embodiments, the temperature variation device comprises a heating source. The heating source can include a near infrared heating source, either coupled to and integrated with the ultrasound imaging device or separate from the ultrasound imaging device. Alternatively, or in addition to, the heating source can include a second ultrasound source.

In some embodiments, the temperature variation device can include a cooling source. The cooling source can be, for example, a cooling pad.

The foregoing and other objects, features, and advantages of the invention will become more apparent from the following detailed description, which proceeds with reference to the accompanying figures.

BRIEF DESCRIPTION OF THE DRAWINGS

FIGS. 6A-6B US-TSI Experimental Configuration. (A) In vivo experimental set-up. (B) imaging-heating pulse sequence.

FIGS. 7A-7H illustrate wall thickening in different vessel groups. Atherosclerotic vascular segments in the CFA exhibited wall thickening (FIG. 7A) due to the formation of lipid-rich AP (FIG. 7B). No plaque was observed in both non-atherosclerotic (FIGS. 7C-D) and normal diet control (FIGS. 7E-F) groups. Atherosclerotic vessels exhibited a significant increase in wall thickness (*p<0.001) versus both non-atherosclerotic and control vessels, while no significant difference was observed between non-atherosclerotic and control vessels (†p=0.126) (FIG. 7G). US and histological measurements of wall thickness showed good correlation (FIG. 7H).

FIGS. 8A-8F illustrate US-TSI Contrast Versus Temperature Rise. US B-mode image (FIG. 8A) for a longaxis view of atherosclerotic CFA 10 weeks post-injury shows a luminal stenosis (arrows) and US Doppler (FIG. 8B) exhibits reduced blood flow signal (arrows). Histological cross-section within the stenotic lesion (FIG. 8C) confirms lipid-rich AP (arrows). US-TSI maps co-registered to the B-mode (FIG. 8A) were reconstructed at ~0.5° C. (FIG. 8D), ~1.5° C. (FIG. 8E), and ~2.5° C. (FIG. 8F) temperature rise. The dashed lines in (FIG. 8A) and subsequent B-mode highlight the area receiving most of heating beam (from maximum and to −3 dB). BF: bifurcation.

FIGS. 9A-9G illustrate US-TSI of atherosclerotic vessels. (FIG. 9A) US B-mode long-axis and (FIG. 9B-C) short axis (arrows) views of atherosclerotic CFA 12 weeks post-injury. US-TSI (FIG. 9D-F) for the three views in (FIG. 9A-C) identified lipids as positive TS in the vessel wall. Long-axis (FIG. 9D) and short-axis (FIG. 9E-F) US-TSI exhibited good agreement in detecting lipid-rich lesions. (FIG. 9G) Oil red O stained histological cross-section of CFA 5 mm proximal to the BF (left) with rectangular inset shown at 5× magnification on right. US-TSI and histology showed good agreement in detecting lipids (red) in the vascular wall. BF: bifurcation.

FIGS. 10A-10E illustrate US-TSI of non-atherosclerotic vessel. (FIG. 10A) US B-mode long-axis view of the contralateral uninjured CFA of the rabbit in FIG. 4. (FIG. 10B) B-mode short axis view of the CFA at the level of the arrows in (FIG. 10A-B). US-TSI of the same long- and short-axis views (FIG. 10C-D) shows mostly WBT (blue and green) with no lipid contents (yellow and red) near the inner vessel layer. (FIG. 10E) Oil red O stained histological cross-section of CFA 5 mm proximal to the BF (left panel) with rectangular inset shown at 5× magnification on the right. Histology shows no signs of AP, concordant with the absence of positive TS signal with US-TSI. BF: bifurcation.

FIGS. 11A-11F illustrate detection of different lipid progression in vascular segments by US-TSI. (FIG. 11A) US-TSI of the non-atherosclerotic CFA showing predominantly negative TS. FIG. 11B-C) US-TSI of atherosclerotic CFAs at 8 and 12 weeks post-injury, respectively. The US-TSI in (C) exhibits larger areas of lipids (positive TS) than those detected in (FIG. 11B). (FIG. 11D-F) Gross specimens of the CFAs shown in (FIG. 11A-C), respectively, excised on the day of imaging, and stained with oil red O for lipids. The uninjured non-atherosclerotic CFA (D) shows no lipid staining, while there was progressively more extensive lipid staining of the CFA at 8 (FIG. 11E) and 12 (FIG. 11F) weeks, paralleled with more spatially extensive positive US-TSI distribution. BF: bifurcation.

FIGS. 12A-12D illustrate longitudinal monitoring of lipids by US-TSI. (FIG. 12A-D) US-TSI at ~1.5° C. temperature rise for the CFA in FIG. 8 showing lipid progression in AP at different time points up to 10 weeks post-injury. The value and total area of positive TS in US-TSI increased gradually between 4 and 10 weeks, consistent with increasing lipid content of AP. AP development was confirmed using histology (FIG. 8C). BF: bifurcation.

FIGS. 13A-13E illustrate high-resolution US-TSI. (FIG. 13A) High-resolution US B-mode long-axis view of atherosclerotic CFA acquired using high-frequency scanner. (FIG. 13B) B-mode for the same CFA acquired using the clinical mid-frequency US scanner. The high-resolution US-TSI (FIG. 13C) for the view in (FIG. 13A) shows lesions of lipids (positive TS) in the CFA similar to those detected in the US-TSI (FIG. 13D) for the view in (FIG. 13B). (FIG. 13E) Histology for the cross-section indicated by arrows on US images confirms the development of lipid-rich AP. BF: bifurcation.

FIG. 15 illustrates types of tissue and its typical thermal and mechanical properties.

FIG. 16 illustrates a TSI process governed by equations (1)-(5) that was numerically solved using the finite element (FE) method (COMSOL V.3.5a, Burlington, Mass.) for a plaque, the geometry of which is outlined in FIG. 16.

FIGS. 19A-19D illustrates (a) pulse pressure over 1 pump cycle (b) total strain (c) decomposed thermal strain and (d) decomposed mechanical strain. The images are reported at different phases of the cardiac cycle marked by circles in (a). Line plots show the corresponding strains in a region in rubber marked by x.

FIGS. 21A-21D illustrate thermal strain (a), peak mechanical strain (b) and Oil-Red-O staining (c) of excised human atherosclerotic vessel. (d) Thermal strain in a fatty region as a function of time. Dashed lines in (a) indicate the US heating beam (full width at half max.).

FIG. 24 illustrates a simplified tank circuit model near resonance used to calculate the heating element electrical to acoustic efficiency.

FIG. 25 shows a table of transducer model parameters.

FIG. 29 provides a comparison between flat and spherical apertures.

FIG. 30 shows tables of physical properties of a test phantom and an in vitro US-TSI study heating array excitation parameters.

FIG. 32 shows a table of metrics to produce 3° C. tissue rise in 2 seconds and properties of a test phantom and a table indicating the heating effectiveness for flat and spherical apertures.

FIG. 33 illustrates a power flow link budget for both flat and spherical apertures to account for the translation efficiencies at each point in the transmission pathway.

FIG. 40 illustrates ultrasound images acquired using the high-frequency ultrasound configuration for a control liver.

FIG. 41 illustrates ultrasound images acquired using the high-frequency ultrasound configuration for a fatty liver.

FIG. 43 illustrates an exemplary experimental set-up and an optical image of a typical CEA specimen.

FIG. 46 shows the results of another in vitro study to image an atherosclerotic cross-section.

DETAILED DESCRIPTION

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language. The terms "fats" and "lipids" are interchangeably used herein to refer to any fat-containing substance in a subject.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

The accumulation of lipids in tissues and organs in the body can reflect important signatures of biological and clinical process of high-risk diseases. As discussed herein, early detection, characterization, and continued monitoring of lipid contents in such tissues and organs can provide critical information for diagnosis and treatment managements.

Steatosis, the accumulation of fat-containing vacuoles within hepatocytes, is a key histological feature of fatty liver disease. However, conventional techniques for obtaining such information about the accumulation of these fat-containing substances are invasive (e.g., biopsies), expensive (e.g., MR images or CT scans), and/or ionizing (e.g., CT scans).

Other techniques, such as ultrasound B-scan imaging are unable to provide sufficient quantitative information about the degree of fat accumulation. For example, conventional ultrasound imaging of certain non-fatty substances, such as hemangioma, render them indistinguishable from fatty substances. The sensitivity of US to detect steatosis also decreases sharply if the degree of fat infiltration is less than about 30%, while the liver condition with fat above 10% is termed a fatty liver disease or steatosis. Therefore, current US modalities are not sensitive enough to detect early steatosis, which greatly limits their use in preventative management of liver disease such as NAFLD.

Figure 1:
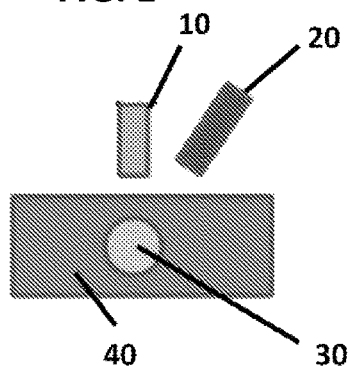
FIG. 1 illustrates a schematic illustration of a system for providing non-invasive detection of fat-containing substances.

FIG. 1 illustrates a schematic imaging system that utilizes US-induced thermal-strain imaging for fat quantification in liver at high sensitivity and high resolution. Thermal strain imaging exploits the relationship between temperature and sound speed in different types of materials to create thermal strain images. In particular, sound speed in lipids decrease with increase in temperature (i.e., a negative temperature dependence), while sound speed increases in water-based tissues with increases in temperature (i.e., a positive temperature dependence). By combining controlled temperatures modulation with high resolution phase sensitive speckle tracking, lipid contents in tissues or organs can be accurately characterized.

As shown in FIG. 1, an ultrasound imaging system 10 can be used in combination with a temperature variation source 20 to obtain thermal strain images of a targeted area 30 of a subject 40. In FIG. 1, subject 40 is schematically represented; however, it should be understood that subject 40 represents any physical object such as a human or other mammal, or a structure that is capable of simulating the targeted tissue of a subject (e.g., a phantom). Targeted area 30 is surrounded by adjacent structure, which represents the tissue surrounding the liver of the subject.

The temperature variation source can be any source capable of altering the temperature within the targeted area of the phantom, such as a heating source. In some embodiments, the temperature variation source can be controlled so that the temperature of the targeted area changes by about 5 degrees Celsius or less during thermal strain imaging, and, in some embodiments, by about 3 degrees Celsius or less, and, in some embodiments, by about 2 degrees Celsius or less.

The temperature variation source can comprise a device capable of heating the targeted area by a desired amount (e.g., +2 degrees Celsius) and/or cooling the targeted area by a desired amount (e.g., −2 degrees Celsius). Various noninvasive heating and/or cooling sources can be used including, for example, heating/cooling pads, light sources, or focused ultrasound energy.

In some embodiments, the temperature variation source can comprise near infrared (NIR) heating. For larger targeted areas, like the liver, near infrared heating can be advantageous over other heating devices, such as focused ultrasound energy, because NIR heating can heat larger areas more effectively. In this manner, a larger area of the US field of view (or potentially the entire US field of view) can be assessed.

In some embodiments, temperature variation source, such as an US and/or NIR heating source, can be coupled to the ultrasound scanner. For example, a custom designed heating array transducer of 6 elements can be coupled to an imaging US probe, such as SonixTOUCH (Ultrasonix) for mid-range clinical frequency (5-10 MHz) and Vevo2100 (VisualSonics) for high frequency (20-50 MHz), which can provide radio frequency (RF) data and highly accurate speckle tracking for TSI. In another embodiment, a NIR light source can be used in combination with the US probe. For example, a NIR light source can be coupled to the US probe or can be separately provided, e.g., via a handheld source (CS-1000, Genesis, Canada) to provide a heating source.

NIR can be used to increase the body temperature uniformly by about 1-2° Celsius over an extended region in tissues. Preferably, the period in which the temperature is increased is less than about 10 minutes, and in some embodiments less than about 5 minutes. The light-illuminating area and wavelengths of the NIR can be selected to provide efficient and uniform heating of the tissue in the targeted area, depending on the tissue to be heated and its location in the subject (e.g., depth within the subject). The total heat delivered to any part of the tissue can be selected to meet safety requirements, such as the FDA limits of 8 W/kg for 5 minutes.

Figure 2A:
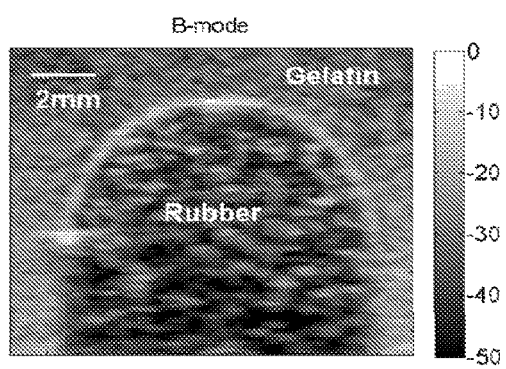
FIGS. 2A and 2B illustrate the use of a B-mode ultrasound image and US-TSI on a phantom.
Figure 2B:
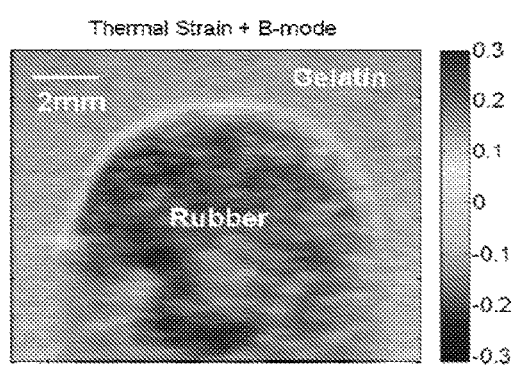
Figure 3A:
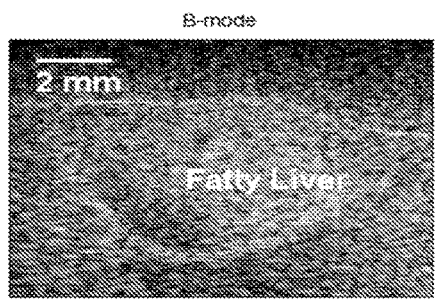
FIGS. 3A and 3B illustrate the use of a B-mode ultrasound image and US-TSI on a fatty liver.
Figure 3B:
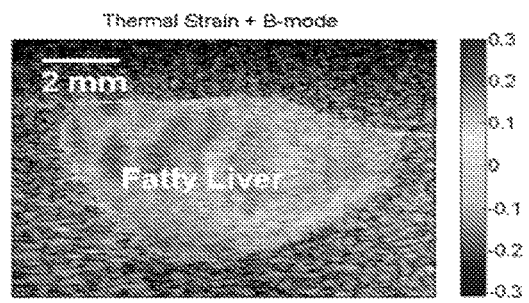

FIGS. 2A and 2B illustrate the use of a B-mode ultrasound image and US-TSI on a phantom. In FIGS. 3A and 3B, these same imaging techniques are demonstrated on a fatty liver, illustrating the ability to detect and quantify fat tissue in the liver in US-TSI in contrast to the B-mode ultrasound image.

Example 1

Figure 4:
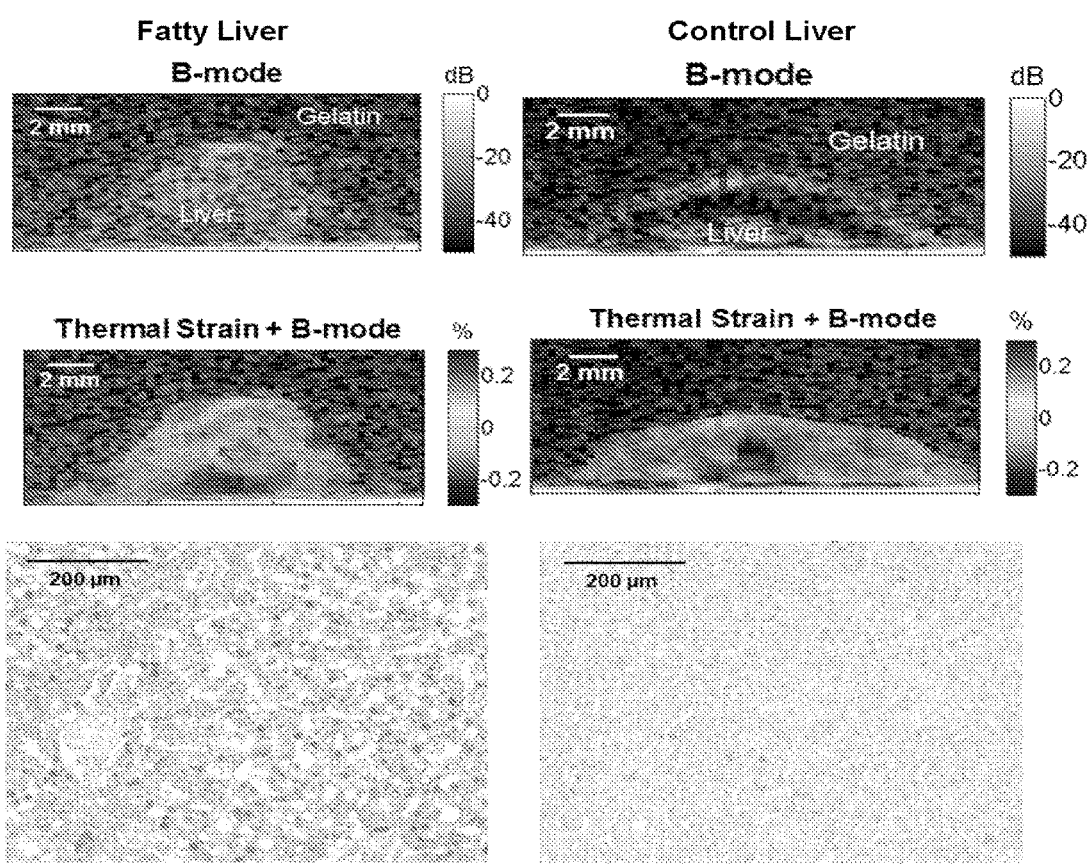
FIG. 4 illustrates temperature-strain maps and histologies of fatty and control livers of mice.

FIG. 4 illustrates temperature-strain maps and histologies of fatty and control livers of mice. FIG. 4(a) illustrates a B-mode ultrasound image for a fatty liver, FIG. 4(b) illustrates ultrasound TSI of the fatty liver in FIG. 4(a), and FIG. 4(c) illustrates a histology slide stained with Oil-Red-O for the fatty liver in FIG. 4(a). A similar analysis was performed for a control liver in FIGS. 4(d)-(f). Positive thermal strains (≈+0.12%, red, shown by arrows) were distributed over the areas where a small temperature increase (less than 2° C.) was induced by either US or NIR was observed in fatty livers, while mostly negative strains (≈−0.08%, blue) were found in control livers for same temperature rise. TSI maps overall matched well with Oil-red-O staining.

Figure 5A:
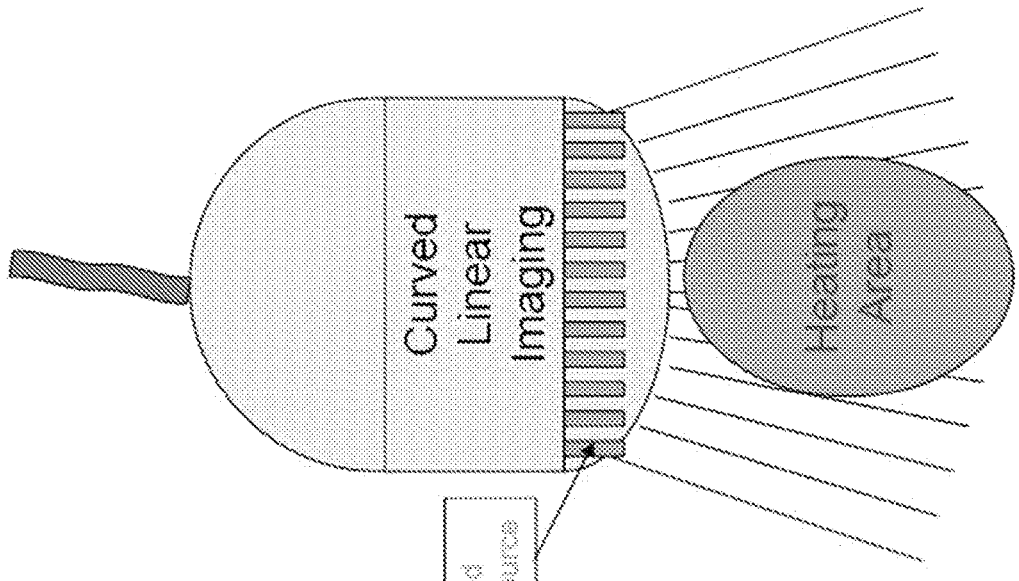
FIGS. 5A-5C illustrate different imaging techniques.
Figure 5B:
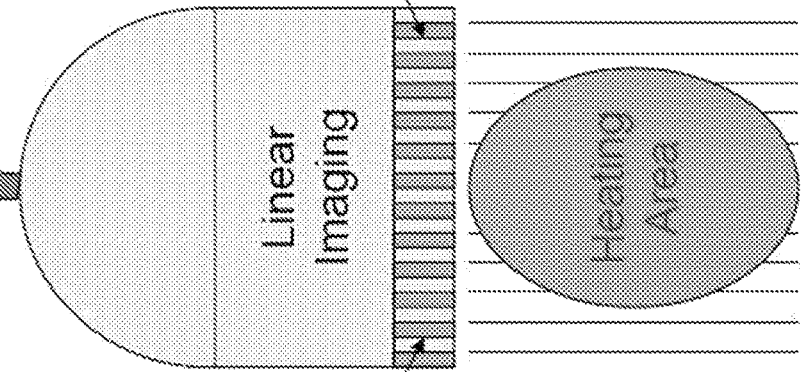
Figure 5C:
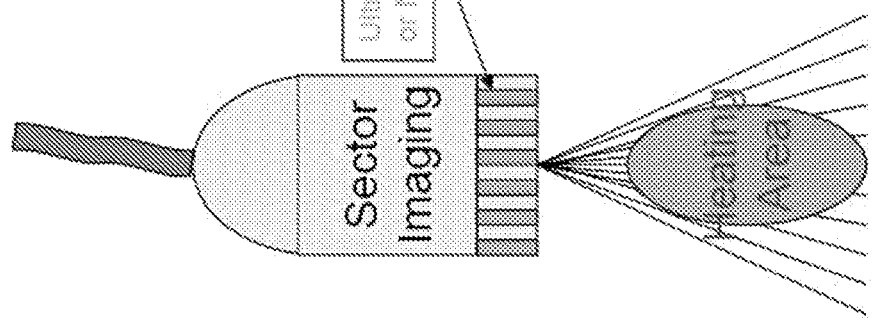

In some embodiments, the NIR light source can be selected to have a beam diameter generally wide enough to cover the targeted area (e.g., liver) of a subject, although in other embodiments, it can be applied to only a portion of the targeted area (e.g., liver) at a time. For example, FIGS. 5A, 5B, and 5C illustrate different designs that provide varied beam diameters of the heating source (e.g., ultrasound and/or NIR). As shown in FIGS. 5A-5C, the heating source can be combined with an imaging device capable of sector imaging, linear imaging, or curved linear imaging.

The TSI techniques described above can effective detect lipid contents in a fatty liver in a non-invasive manner, allowing for the detection and monitoring of lipid deposits in the liver of subjects (e.g., humans and other mammals) with a high degree of sensitivity and resolution. In addition, NIR light source can safely increase the tissue temperature high enough to induce thermal strain in larger organs, such as the liver, to provide more effective TSI.

The ultrasound imaging techniques described herein provide many benefits over conventional techniques for detection and quantification of fats in the tissue and organs of a subject. For example, the systems described herein are non-invasive and non-ionizing. In addition, in some embodiments, the systems can be performed in real-time using portable equipment that is relatively inexpensive. Also, because relatively low temperature changes (e.g., about two degree Celsius) can be used with the thermal strain imaging systems disclosed herein, the heating and/or cooling sources of these combinations is highly translatable as it can be directly applied to a commercial ultrasound scanner with minor modification.

The systems and methods described herein for detection and quantification of fats in the liver can also be used to facilitate screening, either in vivo or in vitro, fatty livers from donated livers for transplantation. For example, the systems and methods disclosed herein (e.g., US-TSI and NIR-TSI) can be used to screen fatty livers either before or after removal of the liver from the donor body to determine the suitability of that liver for transplantation.

In other embodiments, the systems and methods described herein can be used to identify the vulnerability of atherosclerotic plaques. For example, the embodiments disclosed herein that utilize NIR heating (e.g., NIR-TSI) can be adapted for identifying the vulnerability of vascular plaques.

In other embodiments, the systems and methods disclosed herein can be used to differentiate benign (fibroadenoma) from malignant (carcinoma) breast cancer. Currently, the most commonly used breast imaging modalities, including X-ray, ultrasound, and MRI, look for density changes in the breast. However, these techniques cannot reliably distinguish between benign and malignant tumors, and thus can only be used to detect suspicious lesions and not for diagnosis. A tissue biopsy must be performed to determine whether or not a lesion is malignant, and it has been estimated that 70-90% of breast biopsies are found to be benign upon pathological analysis. Accordingly, the systems and methods disclosed herein can be used to differentiate benign from malignant breast tumor to avoid unnecessary biopsies.

As with the embodiments disclosed above relating to the detection and quantification of fats in the liver, ultrasound thermal strain imaging can be used for tissue differentiation within the breast based on the acoustic properties of tissue. That is, the utilization of the underlying principle that sound speed increases with temperature in water-bearing tissue (e.g., a positive temperature dependence) while sound speed in lipid-bearing tissue decreases with temperature in the range of 37 degrees Celsius to 50 degrees Celsius (e.g., a negative temperature dependence). As in other embodiments, the systems and methods disclosed herein can track speckle displacements of temperature varied tissue (e.g., tissue heated 1 degree Celsius) to determine thermal strains and produce images related to the temperature dependency of sound speed.

This modality features strong contrast between lipid-bearing (+0.17%/degree) and water-bearing (−0.1%/degree) tissue with a temperature change of less than about 1 degree Celsius. Also, correlation-based phase sensitive speckle tracking can accurately measure small strains with sub-micron precision.

Because fibroadenoma contains little fat (2%) and carcinoma maintains significant percentage of fat (26%), the strong negative average thermal strain in fibroadenoma can differentiate it from carcinoma which will produce close to zero average strain. In practice, fat in carcinoma is not uniformly distributed. High resolution UTSI can detect this heterogeneity, providing an additional factor for differentiation.

In some embodiments, ultrasound can be used both to heat and image. Among many other forms of heating tissue, ultrasound can be used for its simplicity, safety, and accuracy. In addition, a commercial ultrasound probe can be easily adapted to produce a pulse sequence interleaving heating and imaging. In other embodiments, other temperature variation devices (e.g., NIR heating) can be used to modulate the temperature in the targeted tissue in the breast.

In other embodiments, the systems and methods disclosed herein, including, for example, US-TSI and NIR-TSI, can be used to detect and monitor fat contents in connection with plastic surgery procedures that use fat to shape and support other tissues (e.g., damaged tissues) in any part of the body where ultrasound scanning is accessible.

Example 2—Non-Invasive Detection of Lipids in Atherosclerotic Plaque using TSI

The following example relates to in vivo detection of lipid bearing atherosclerotic plaque (AP) by ultrasound (US) thermal strain imaging (TSI).

Vulnerable AP is recognized by its large lipid pool and thin fibrous cap. Lipids exhibit a distinctive physical characteristic of temperature dependent US speed by comparison to water-bearing tissues. As tissue temperature changes, US radiofrequency (RF) echo signals shift in time of flight which produces an apparent strain (called temporal or thermal strain: TS) which can be differentiated from the mechanical strains generated by cardiac pulsation.

The methods used in the following example include US heating-imaging pulse sequences, transducers, and electronics were designed and integrated into commercial US scanners for US-TSI of arterial segments. US-RF data were collected for maximum 10 s while gradually increasing tissue temperature. 2D phase-sensitive speckle tracking was applied to reconstruct TS maps co-registered to B-scans. Segments from injured atherosclerotic and uninjured non-atherosclerotic common femoral arteries in cholesterol fed New Zealand rabbits, and segments from control normal diet fed rabbits (n=12 total) were scanned in vivo for lipids at different time points during atherosclerotic progression up to 12 weeks.

As discussed in more detail below, lipid-rich atherosclerotic lesions exhibited distinct positive TS (+0.20±0.09%) compared with that in non-atherosclerotic (−0.08±0.14%) and control (−0.09±0.09%) segments (p<0.001), for a temperature rise of ~1.5° C. US-TSI enabled serial monitoring of lipids during atherosclerosis development. The co-registered set of morphological and compositional information of US-TSI showed good agreement with histological findings. US-TSI successfully detected and longitudinally monitored lipid progression in atherosclerotic femoral arteries. US-TSI of relatively superficial arteries may be a modality, which could be easily integrated into a commercial US system to complement other methods for AP characterization.

Introduction

Atherosclerosis, a leading cause of major adverse cardiovascular events, is an arterial disease characterized by vessel wall inflammation and thickening, where lipids, cells, and scar tissue deposit. These compositional changes in the vascular wall lead to the formation of atherosclerotic plaque (AP). APs can rupture and cause major cardiovascular events such as acute coronary syndromes or ischemic stroke. However, the accurate identification of rupture-prone plaques ("vulnerable plaque") has been elusive; the culprit lesions may not be large, nor need they be particularly old. Post-mortem studies have suggested that vulnerable plaque consists mostly of a lipid-rich core separated from the arterial bloodstream by a thin fibrous cap. Accordingly, there has been an increasing need for imaging techniques able to characterize AP composition, particularly lipid content, along with morphological changes. Some of these imaging approaches are in clinical use, undergoing clinical trials, or still under pre-clinical development.

US-TSI is based on the observation that lipid-bearing tissue (LBT) has a negative temperature dependence of sound speed change, while water-bearing tissue (WBT) has a positive dependence. As temperature changes, radiofrequency (RF) US signals either advance or retard in time due to increase or decrease of sound speed. These time shifts produce corresponding apparent temporal, or thermal strain (TS), which has no relation to the mechanical strains generated by tissue compression. US-TSI can add additional information to US elastography by providing direct measurement of plaque lipid content. Previous studies have shown the feasibility of US-TSI to characterize lipids in WBT ex vivo and the possibility of using a single transcutaneous US probe for such purpose. Based on these considerations, this example illustrates that lipids in AP can be characterized via their distinct positive strains in US-TSI in response to the induction of a slight tissue temperature increase. Using a rabbit atherosclerotic model, this example demonstrates the feasibility of detecting lipids in AP non-invasively using US-TSI an in vivo study.

Methods—Animals

Twelve male New Zealand white rabbits (3.5-4 kg) were studied (4 controls, accelerated atherosclerosis. The rabbits in the atherosclerosis group were fed an atherogenic diet (peanut oil 6%, cholesterol 1%) for 5 weeks. One week after commencing this diet, rabbits were anesthetized with ketamine (35-50 mg/kg IM), xylazine (2-10 mg/kg IM) and 2.5% inhaled isoflurane. Under Duplex US guidance, a balloon catheter (2F Fogarty, Edwards Life Sciences LLC, CA) was introduced into the right superficial femoral artery, advanced into the common femoral artery (CFA), inflated at 2 atm, then advanced and withdrawn 3 times to induce injury. Injured right common femoral arteries served as "atherosclerotic" vessels (n=8), while uninjured contralateral common femoral arteries in the same atherosclerosis rabbit group were used as "non-atherosclerotic" vessels (n=8). In an additional 4 rabbits that were fed a normal diet and did not undergo balloon injury, the right CFA served as a negative control for atherosclerosis ("normal diet control") (n=4).

US-TSI

The schematic in FIG. 6A describes the experimental set-up of US-TSI. In vivo US-TSI procedures were performed using a single US transducer (5-14 MHz, axial resolution≈200 μm) for both heating and imaging. The transducer was attached to a clinical US scanner specially featured for RF access and customized beamforming (Sonix-TOUCH, Ultrasonix Medical Corp., Canada). A digital signal derived from the rabbit ECG (THM100, Indus Instruments, TX) served as a trigger to synchronize US-TSI frame acquisition to end-systole (or end-diastole) to eliminate the mechanical strain periodically produced by the cardiac pulsation. An US-TSI imaging-heating sequence was adapted as follows (FIG. 6B): The US sequence begins with imaging for 5 ms from receiving the trigger, followed by heating for 192 ms, and then a short pause (up to 33 ms depending on heart rate) until the next trigger arrives.

In a subset of the animals (n=6), in vivo feasibility of high-resolution US-TSI was also investigated using a high-frequency US machine (Vevo2100, VisualSonics Inc., Canada). A custom designed US heating array transducer (6 elements, 3.55 MHz) was attached to the imaging linear array transducer (13-24 MHz, axial resolution≈75 μm) to efficiently deliver the US power required for tissue temperature increase. The heating pulse (sine wave, 50-60% duty cycle) was amplified via an RF power amplifier (100A250A, Amplifier Research, PA), then fed into a custom designed power splitter to drive the US heating array transducer. A synchronized US sequence similar to FIG. 6B was used.

These interleaving sequences were repeated for a maximum of 10 s while recording USRF frames. Frames were then transferred to Matlab 7.12.0 (The MathWorks Inc., MA) for USTSI signal processing. A temperature increase of 1.1±0.1° C. in 5 s was measured in vivo in tissue segments near the CFA using a temperature sensor attached to a multimeter (Fluke 116, Fluke Corporation, WA) when a heating pulse of 56% duty cycle was adopted.

Signal Processing 2D phase-sensitive speckle tracking was applied to the US-RF frames to estimate the temporal shifts associated with sound speed changes due to temperature rise. Temporal shifts can be seen in US frames as apparent axial displacements in the direction of US propagation. The complex cross-correlation coefficients between small windows (kernels) from successive frames were estimated. Displacements were estimated from the position of the maximum correlation coefficient, and were refined further using the phase zero-crossing of the complex correlation function. TS was computed as the spatial derivative of displacements. TS maps for regions of interest within the arterial segment, color coded such that red and blue indicated the positive and negative strain, respectively, were co-registered and superimposed on B-mode US images. The kernel size used for tracking was equal to US speckle size. For frames acquired by the clinical system, it was approximately 0.19 mm (axial)×0.30 mm (lateral), while for those of the high-resolution system it decreased to approximately 0.07 mm (axial)×0.18 mm (lateral).

Histology

Post-mortem, each CFA was perfusion-fixed, excised, embedded in molds of OCT compound, and frozen at −80° C. Short-axis sections (8-10 μm thick) were stained with general hematoxylin and eosin for morphological assessments and nuclei staining, and oil red O and hematoxylin counterstaining for lipid staining. The location of each histology section was identified relative to its distance from the common femoral bifurcation, which was similarly used as a landmark on the US images to enable comparison between the US findings and histology at anatomically concordant sites. Some arteries underwent whole vessel oil red O staining to investigate lipid infiltration along the vessel wall.

Vessel wall thickness, from lumen boundary to adventitial layer, was measured and compared with US B-mode measurement at the corresponding segment where US-TSI was performed. To quantify the percentage of lipid progression in an atherosclerotic vessel, a region of interest, from lumen boundary to adventitial layer, was manually segmented. Then, the area of red stained lipids (oil red O) was evaluated and divided by the total segmented area. Similar procedures were followed to quantify percentage lipids in corresponding segments within US-TSI for comparison. All histological quantitative measurements were performed using Image J software 1.46r (National Institutes of Health, Bethesda, Md.).

Statistical Analysis

Data analyses were performed using the Statistics Toolbox of Matlab 7.12.0. All values are expressed as the mean±SD. Wall thickness and TS assessments in the atherosclerotic, nonatherosclerotic, and control vessel groups were compared using Student's t test. Linear regression analysis was performed to compare US and histology measurements of wall thickness and lipid progression. A p value <0.05 was considered significant (two-tailed).

Experimental Protocol

Serial US-TSI of the CFA, co-registered to Duplex US, was performed on the rabbits at week 0 (day of injury), and 4, 6, 8, 10 or 12 weeks post-injury. Rabbits were euthanized at week 4 (n=1), 6 (n=1), 8 (n=2), 10 (n=1) and 12 (n=3) post-injury, and tissue was processed postmortem. This design enabled correlation of US-TSI and histological data from the same time point in some rabbits (terminal day) as well as serial monitoring of lipid composition over time in others (US-TSI data only). Blood was drawn on the day of injury and on the terminal day for measuring total serum cholesterol levels.

Results

Cholesterol levels. Serum cholesterol in the atherosclerosis rabbit group was 669±412 mg/dL on injury day and 517±296 mg/dL on the terminal points, whereas it was 32±15 mg/dL in the control group.

Figure 7H:
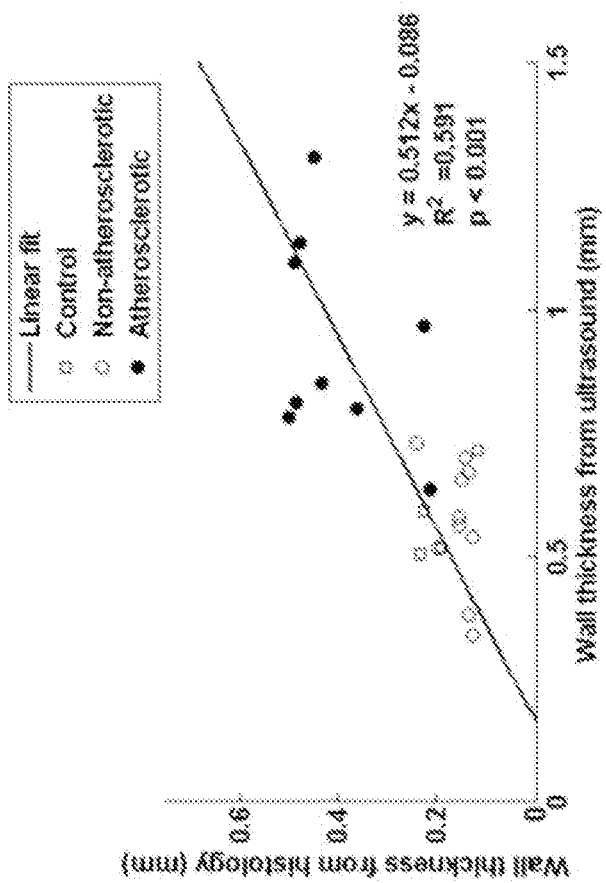
Figure 7G:
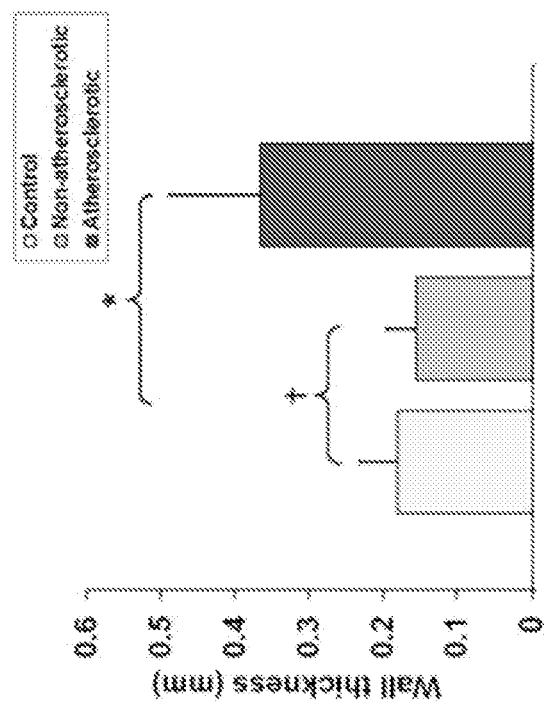

Plaque formation and vessel wall thickness. FIGS. 7A-B show representative histology of atherosclerotic common femoral arteries. The arteries exhibited lipid-rich AP formation (FIG. 7B), whereas no plaque developed in either the non-atherosclerotic (FIGS. 7C-D) or control (FIGS. 7E-F) vessel groups. Using histology measurements (FIG. 7G), the atherosclerosis group exhibited a significant increase in the vessel wall thickness (0.40±0.12 mm) compared with non-atherosclerotic (0.16±0.04 mm) and control (0.18±0.05 mm) groups (p<0.001). There was no difference in vessel wall thickness between the non-atherosclerotic and control vessel groups (p=0.126). US measurements of vessel wall thickness showed good correlation with those measured from the histology of approximately matched segments (FIG. 7H).

Effect of temperature on US-TSI contrast. FIG. 8 depicts in vivo US-TSI of an atherosclerotic CFA 10 weeks post-injury at three different levels of temperature rise. The long axis B-scan (FIG. 8A) shows a noticeable luminal stenosis (arrows) and correspondingly reduced US Doppler signal (FIG. 8B) in the lumen (arrows). The dash lines in FIG. 8A mark the area that receives most of the heating beam (from maximum and down to −3 dB). Small positive TS (0.09±0.02%) was measured within the suspected atherosclerotic lesion at ~0.5° C. (FIG. 8D), providing relatively low TS contrast relative to surrounding areas. The same lesion exhibited more positive TS of 0.30±0.08% and 0.45±0.10% at ~1.5° C. (FIG. 8E) and ~2.5° C. (FIG. 8F), respectively. Oil red O staining of the arterial segment corresponding to the US image (FIG. 8C) confirmed the presence of lipid-laden (red) AP (arrows). A temperature rise of ~1.5° C. was used for subsequent US-TSI experiments as it provided sufficient contrast between lipids and WBT while minimizing the required temperature rise.

US-TSI of atherosclerotic and non-atherosclerotic arteries. US-TSI of atherosclerotic and contralateral non-atherosclerotic (uninjured) common femoral arteries in a cholesterol-fed rabbit 12 weeks post-injury are shown in FIGS. 9 and 10, respectively. B-scans of the atherosclerotic artery were acquired in long-axis (FIG. 9A) and short-axis views (arrows in FIGS. 9B-C) at ~2 mm and ~4 mm from the bifurcation (arrow in FIG. 9A), respectively. The long-axis US-TSI (FIG. 9D) detected lipids (red) within the vessel wall including plaque. Lipids were also identified in short-axis US-TSI (FIGS. 9E-F), and exhibited good agreement with long-axis findings (FIG. 9D). Histology of the section imaged with US (FIG. 9G) indicated wall thickening, AP development, and lipid accumulation at these sites.

Similar procedures were applied to the non-atherosclerotic contralateral artery of the same rabbit. The B-mode image of the short-axis view (FIG. 10B) is ~4 mm from the bifurcation (arrow in long axis view in FIG. 10A). US-TSI (FIGS. 10C and D) did not indicate positive TS in the vascular wall near the lumen. Histology (FIG. 10E) showed normal vessel wall and confirmed the US-TSI findings.

Monitoring of lipid progression using US-TSI. FIGS. 11A-C depict the US-TSI of a nonatherosclerotic and 2 atherosclerotic common femoral arteries of cholesterol-fed rabbits euthanized at week 8 and 12 after injury, respectively. FIGS. 11D-F show the corresponding gross oil red O stained arterial segments. The non-atherosclerotic artery (FIG. 11A) exhibited predominantly negative TS values (WBT), consistent with the absence of lipid lesions (FIG. 11D). In comparison, very noticeable positive TS values were observed in the atherosclerotic arteries (FIGS. 11B-C). Progression of positive TS was observed at week 12 (FIG. 11C), corresponding to more widespread lipid infiltration at week 12 (FIG. 11F) compared to week 8 (FIG. 6E). Serial US-TSI was performed for the atherosclerotic CFA of the same rabbit shown in FIG. 3 at 4, 6, 8, and 10 weeks post-injury using a temperature rise of ~1.5° C. Slight positive TS values were observed in the plaque and vessel wall at week 4 (FIG. 12A), which increased at week 6 (FIG. 12B), and progressed in intensity and spatial extent in weeks 8 and 10 (FIG. 12C-D).

High-resolution US-TSI. The high-resolution B-scan (FIG. 13A) of an atherosclerotic CFA (12 weeks post-injury) exposed finer details than those shown by the clinical system (FIG. 13B) for the same vessel. The corresponding high-resolution US-TSI (FIG. 13C) identified lipids in the upper and lower vessel walls including AP. Lipids were detected in similar sites using US-TSI of the clinical system (FIG. 13D). Oil red O histology (FIG. 13E) of a corresponding cross-section (arrow in FIGS. 13A-D) showed lipid co-localization with the positive TS.

Figure 14A:
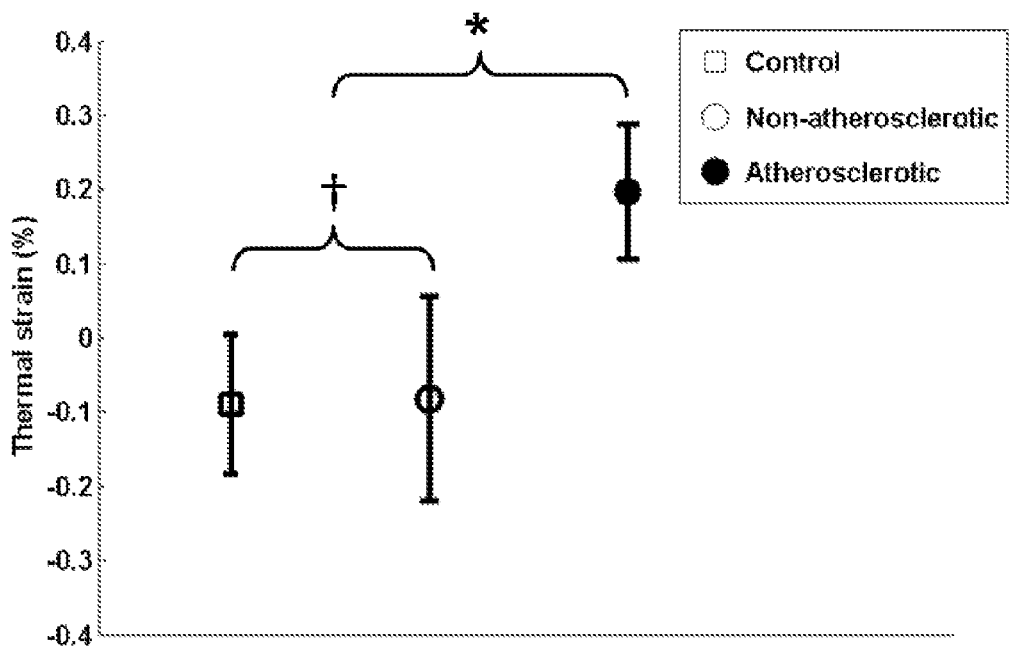
FIGS. 14A-14B illustrate quantitative analysis of TS and correlation with histology. TS in lipid-rich atherosclerotic segments significantly differed (*p<0.001) from that measured in similar segments in both non-atherosclerotic and normal diet control segments (FIG. 14A). No significant difference in TS was observed between non-atherosclerotic and normal diet control segments (†p=0.786). US-TSI and histology measurements of percentage lipid content in matched atherosclerotic segments exhibited close correlation (FIG. 14B).

Quantitative assessment of lipid-rich AP using US-TSI. TS in lipid-rich atherosclerotic segments (n=8) was significantly higher (p<0.001) than that measured in similar segments in both uninjured non-atherosclerotic (n=8) and normal diet control segments (n=4) (FIG. 14A). Atherosclerotic segments exhibited positive strains of +0.20±0.09%, whereas non-atherosclerotic and normal diet control segments exhibited mostly negative strains of −0.08±0.14% and −0.09±0.09%, respectively. No significant difference in TS was observed between nonatherosclerotic and normal diet control segments (p=0.786).

A close correlation was found between histological and US-TSI measurements of percentage lipid content in matched atherosclerotic segments (n=8) (FIG. 19B).

Discussion

This example demonstrates that US-TSI is capable of identifying lipid content in atherosclerotic plaques in vivo. Using a rabbit model of accelerated atherosclerosis, our data are the first in vivo demonstration that differences in TS between atherosclerotic and normal segments can be spatially mapped and shown to co-localize with histologically proven lipid-laden atherosclerotic plaque. These data have major implications for the in vivo detection of rupture-prone plaques and perhaps for clinical prediction of plaque instability.

A significant difference in TS was measured between normal diet control and nonatherosclerotic (uninjured) segments versus atherosclerotic (injured) segments. Atherosclerotic segments exhibited distinct positive TS as would be expected in LBT, whereas control and nonatherosclerotic segments possessed negative TS typical of WBT. Similar TS values have been measured in vitro by others at similar temperatures. We observed relatively large SD of TS in atherosclerotic segments, probably for several reasons. First, because we lumped together all AP measurements over time, variations in lipid content with atherosclerosis progression from 4 to 12 weeks increased the range of positive TS measurements. Second, atherosclerotic segments contain different WBT such as smooth muscle cells, connective tissue, and fibrosis, which would have negative temperature dependences of the speed of sound. This would result in heterogeneous TS maps, which would increase the variation in TS measures, as the varied tissue components cannot be completely excluded during image segmentation. TS in normal diet control and non-atherosclerotic segments also had large SD, as some areas in these arteries exhibited positive TSs, which could be due to normal adventitial fat. Notwithstanding these inherent limitations, the average TS clearly differentiated lipid-rich AP from WBT with high significance ($p<0.001$).

Terminal study points were varied to compare US-TSI and histology findings at different stages of atherosclerosis progression. The US-TSI and histological data exhibited good agreement in detecting lipids at different weeks postinjury. Atherosclerotic segments at 4 weeks post-injury may show mostly intimal and medial SMC proliferation and early fatty streaks typical of early atherogenesis, co-incident with small values of positive TS (FIG. 12A). Although some atherosclerotic vessels did not show a significant stenosis in conventional Duplex US, US-TSI was able to detect AP fatty lesions in their walls that was not flow limiting. Furthermore, US-TSI tracked serially lipid accumulation during AP progression exhibiting a continuous change in the area or/and value of positive TS in AP over time (FIG. 12). Continuous remodeling in the shape of AP at different stages may suggest corresponding changes in lipid distribution. Although a slight misalignment in our imaging planes between each week is possible, the overall observations were consistent with the interpretation of AP progression.

Figure 14B:
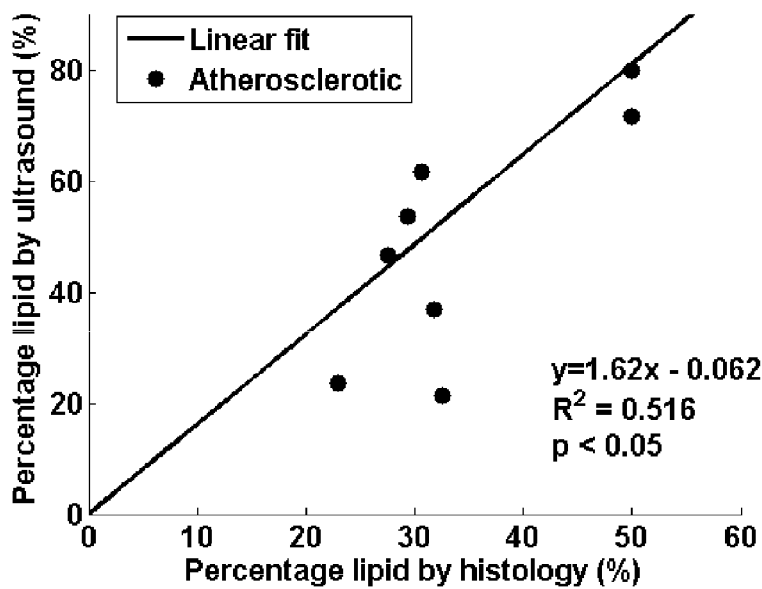

Our quantitative analyses showed good correlation between US and histology measurements (FIGS. 7H and 14B). Any discrepancies between absolute magnitudes in US and histology measurements may be due to the limited resolution of US compared to highmagnification histology optical images, and/or the potential post-mortem changes in vessels during histology processing.

Although attempts have been made to modify the beamforming of the clinical transducer to perform both imaging and heating, there are still inherent limitations, such as limited heating beam width since it was originally designed for conventional US "imaging". To address this issue, separate heating transducer can be incorporated with an imaging transducer, and provide compactness and ease of translation. In this effort, a prototype heating transducer was developed and tested with the Vevo2100 US system. Our data showed a larger and more uniform heating pattern for US-TSI (FIGS. 13A and C). US-TSI on a high-resolution scanner can be performed, which may permit research studies of atherogenesis in small animals.

US-TSI relies on inducing a slight temperature rise in tissue, so it is important to control the temperature rise for safe in vivo use. Direct in vivo temperature measurements exhibited a temperature rise of $1.1\pm0.1°$ C. per 5 s using current US-TSI configurations. At this small temperature ($<10°$ C.), a linear relationship between sound speed change and temperature rise can be assumed. Accordingly, the temperature rise during US-TSI can be estimated using the linear relationship between heating time (number of US frames) and thermal strain. In this example, US-TSI reconstructed using a temperature rise of ~1.5° C. provided a TS difference of about 0.30% distinguishing lipid-rich atherosclerotic segments from control and nonatherosclerotic segments (FIG. 14A), whereas a temperature rise of ~0.5° C. (FIG. 8D), produced relatively low (insufficient) TS contrast. Inducing relatively higher temperature of ~2.5° C. enhanced the contrast between lipids (red) and WBT (blue) even more (FIG. 8F), but did not provide additional US-TSI information compared to ~1.5° C. (FIG. 8E). For future clinical implementation, we chose an US-TSI temperature increase of ~1.5° C. in less than 10 s, which generated sufficient signal/noise without conferring significant adverse biological effects as outlined by the American Institute of Ultrasound in Medicine. Also, the mechanical index (MI) was estimated during US-TSI procedures using both machines. MI was found to be maximum 0.96, which is below the FDA maximum allowance (MI<1.9) to avoid adverse biological effects.

ECG gating was adopted to acquire US-TSI frames at the same phase of the cardiac cycle to eliminate the mechanical strain associated with arterial pulsations. However, other sources of physiologic motion, such as breathing, may result in artifacts. To minimize breathing motion artifact, rabbits were intubated for breathing under anesthesia, and their legs were fixed to the scanning table using surgical tape. Also, breathing motion did not vary locally in the relatively small imaging area, and was eliminated in the course of thermal strain computation through spatial differentiation. When translated to humans, this challenge may be circumvented by breath hold for considerably less than 10 s. In one embodiment, a US-TSI configuration using spherically focused heating US array can increase tissue temperature by a rate of ~1° C. per human cardiac cycle, which will minimize motion artifacts and potential patient discomfort due to breath hold. Additionally, the use of spatial interpolation and linear least squares fitting can further reduce the adverse effects of motion.

Accordingly, as discussed above, US-TSI was able to detect and longitudinally monitor lipids in the APs of rabbits subjected to accelerated atherosclerosis. Lipids in atherosclerotic arterial segments exhibited distinct positive TS, whereas normal diet control and uninjured non-atherosclerotic arterial segments of cholesterol fed rabbits, comprising mostly WBT, showed predominantly negative TS. Lipid-rich lesions identified by US-TSI co-localized and were quantitatively concordant with histological data. These findings demonstrate the potential utility of US-TSI for noninvasive lipid detection and monitoring in AP in vivo. These novel systems and methods for tissue characterization have various useful applications not only in preclinical research studies, but also on clinical management and risk stratification of patients.

Example 3—Motion Artifact Reduction

The following example relates to motion artifact reduction in US based TSI. As discussed above, large lipid pools in vulnerable plaques can be detected using US based thermal strain imaging (US-TSI). One practical challenge for in vivo cardiovascular application of US-TSI is that the thermal strain is masked by the mechanical strain caused by cardiac pulsation. ECG gating is a widely adopted method for cardiac motion compensation, but it is often susceptible to electrical and physiological noise. This example illustrates an alternative time series analysis approach to separate thermal strain from the mechanical strain without using ECG. As described in detail below, the performance and feasibility of the time-series analysis technique was established via numerical simulation as well as in vitro water tank experiments using a vessel mimicking phantom and an excised human atherosclerotic artery where the cardiac pulsation is simulated by a pulsatile pump.

Introduction

Plaques characterized by a large, soft lipid core and a thin fibrous cap have been identified as "vulnerable plaques", or "rupture-prone plaques." Identifying these potentially fatal plaques before their disruption is clinically desirable and will help predict vascular risk and guide therapies. Ultrasound (US) based thermal strain imaging (US-TSI) is being investigated as a potential modality to detect lipid cores buried in normal tissue non-invasively. US-TSI is based on the temperature dependence of the speed of US waves in tissue. For a small rise in temperature (<10° C.) near the normal body temperature of 37° C., US speed increases linearly in non-fatty tissue and decreases linearly in fatty (lipid bearing) tissue. This change in US speed manifests as apparent strain (also called thermal strain) between two US frames captured before and after temperature rise: in lipid, it appears as positive strain or stretching; in normal tissue, it appears as negative strain or compression. In US-TSI, one exploits this contrast in apparent strain to identify a lipid pool buried in normal tissue. In US-TSI, not only the imaging is done using US, but the slight local temperature rise (2-3° C.) required for TSI is also achieved through US induced heating. US-TSI can be performed either using IVUS or using a commercial US linear array transducer that is traditionally used for imaging. The latter approach is non-invasive and is suitable for applications in superficial arteries such as the carotid atherosclerotic plaques. In this example, a single commercial linear array transducer is used to perform US-TSI.

A practical difficulty for in vivo cardiovascular application of US-TSI is posed by another source of strain in the artery, viz. the mechanical strain due to pulsatile blood pressure which is higher in magnitude than the thermal strain. The total strain measured by US is a sum of the larger mechanical strain and the smaller thermal strain. If proper steps are not taken, thermal strain is completely masked by the mechanical strain. ECG gating can be a solution to the above problem. Since ECG and arterial pulsation have the same periodicity, two US frames can be captured at the same blood pressure level using ECG gating, thereby eliminating any mechanical strain between them. If ECG and blood pressure are perfectly synchronous, one can ensure that mechanical strain does not mask the thermal strain. However, noise in the electrical circuits often interferes with the relatively weak ECG signal since the typical ECG output level is 1 mV or less. In many cases ECG gating becomes unreliable due to electromagnetic interference through electrodes and cables, bad coupling, or false peak detection. In some patients, the synchrony and regularity of ECG and cardiac pulsation may also be affected by physiological factors.

To avoid the above technical difficulties arising from ECG and make US-TSI technique ECG independent, we propose a time series analysis technique to separate the thermal strain and the mechanical strain from the mixed signal. We note that the mechanical strain is periodic—rising and falling periodically with blood pressure, while the thermal strain is monotonically increasing—since we keep on slowly increasing the temperature of the tissue throughout the entire imaging period. The total strain measured via US speckle tracking with a frame rate several times the heart rate, therefore, is a sum of a trend and a periodic component. The Holt-Winters (H-W) algorithm was proposed in the early 1960s to separate trends from periodic variations and has since been used extensively in business management and inventory control. In this paper, we adopt the H-W algorithm to extract the thermal strain (trend component) and the mechanical strain (cyclic component) from the total strain measured by US. H-W does not make any prior assumption about the shape of the trend or the periodic component, making it ideal for the current application where the exact temporal patterns of the thermal and mechanical strains are expected to vary from patient to patient depending on the composition and structure of the plaque and vessel wall as well as the patient's heart condition. In this example, the applicability of US-TSI in conjunction with H-W algorithm for cardiovascular application is established using numerical simulation as well as in vitro experiments using a vessel mimicking phantom and an excised human atherosclerotic artery connected to a pulsatile pump in a water tank.

US-TSI and H-W

TSI of an atherosclerotic plaque in the presence of blood flow. The apparent strain (a.k.a. thermal strain) ($\varepsilon_{th}$) between two US frames captured at temperatures $\theta_0$ and $\theta$ respectively ($\theta > \theta_0$, $\theta_0 \approx 37°$ C., $\theta - \theta_0 < 10°$ C.) as a function of location ($\underline{x}$) is given by:

$$\varepsilon_{th}(\underline{x}) = [(\beta - \alpha)(\theta - \theta_0)](\underline{x}) \approx [-\alpha(\theta - \theta_0)](\underline{x}) \text{ when } |\beta| << |\alpha| \quad (1)$$

where $\beta(\underline{x})$ is the thermal expansion coefficient and $$\alpha(x) = \left[\frac{1}{2} \times \frac{\partial c}{\partial \theta}\bigg|_{\theta = \theta_0}\right](x)$$

is the coefficient of thermal dependence of sound speed (c) at temperature $\theta_0$. For a small rise in temperature (<10° C.) near 37° C., both $\alpha$ and $\beta$ are practically constant over the range $\theta_0$ to $\theta$, and $|\beta| << |\alpha|$. In normal tissue, $\alpha$ is positive (i.e. US speed increases with temperature increase) while in fatty (lipid bearing) tissue $\alpha$ is negative (i.e. US speed decreases with temperature increase). As a result, the thermal strain $\varepsilon_{th}$ due to a rise in temperature is negative in normal tissue and positive in fatty tissue.

In US-TSI, the heat required for the temperature rise $\theta_0 \to \theta$ is induced by US according to the equation:

$$Q_{us}(\underline{x}) = (2\xi P_{np}^2 \gamma / \pi c)(\underline{x}) \quad (2)$$

where $Q_{us}$[W/cc] is the heat produced per unit time per unit volume, $\xi$ is the acoustic absorption coefficient, $P_{np}$ is the peak negative US pressure, $\gamma$ is the US transmit duty cycle, and c is the US speed. Typically, a longer ultrasound pulse than what is used for imaging is necessary to generate any appreciable temperature rise. The time required to ultrasonically increase the temperature of the tissue in a given region $\Omega$ from $\theta_0$ to $\theta$ is determined by the bioheat equation:

$$\rho C \frac{\partial \theta}{\partial t} = \nabla \cdot (k \nabla \theta) - W_b C_b (\theta - \theta_0) + Q_{us} \text{ in } \Omega \quad (3)$$

where $\rho$ is the density of the tissue, $C$ is its specific heat, t is time, k is the thermal conductivity of the tissue, $W$ is the blood perfusion rate and $C$ is the specific heat of blood. Since our target region $\Omega$ is an atherosclerotic plaque, the luminal boundary $\delta\Omega_{lum} \subset \delta\Omega$ undergoes a steady convectional cooling due to blood flow in the artery while the remaining boundary is assumed to be at constant temperature $\theta_0$:

$$\frac{\partial \theta}{\partial t} + \nabla \cdot (\underline{v}_b \theta) = 0 \text{ in } \delta\Omega_{lum} \subset \delta\Omega \quad (4)$$

$$\theta = \theta_0 \text{ in } \delta\Omega \setminus \delta\Omega_{lum}$$

where $\underline{v}_b$ is the blood flow velocity. Eq. (1)-(3) govern the thermal strain development in an atherosclerotic plaque. In addition to the thermal strain, there is also a mechanical strain ($\varepsilon_{ms}$) in the plaque caused by pulsatile blood pressure with a period $\tau$, so that the total strain ($\varepsilon$) at any given time t is given by:

$$\varepsilon(t) = \varepsilon_{ms}(t) + \varepsilon_{th}(t) \text{ in } \Omega \quad (5)$$

where the mechanical strain component satisfies the periodicity condition $\varepsilon_{ms}(t) = \varepsilon_{ms}(t-\tau) \forall t$. The total strain $\varepsilon$ is what a US imaging system will measure via speckle tracking. The challenge for cardiovascular TSI is to extract the thermal strain $\varepsilon_{th}$ from the total strain $\varepsilon$.

Extracting thermal strain from the total strain using H-W algorithm. There are various forms of the H-W. In one form, a first step in the H-W algorithm is to find an estimate $\hat{\tau}$ of the period $\tau$ (heart rate in our case) either through autocorrelation or through Fourier transform of $\varepsilon(t)$. This estimate is then used to solve the implicit set of equations:

$$\hat{\varepsilon}_{th}(t) = \kappa(\varepsilon(t) - \hat{\varepsilon}_{ms}(t-\hat{\tau})) + (1-\kappa)(\hat{\varepsilon}_{th}(t-1) + b(t-1))$$

$$b(t) = \lambda(\hat{\varepsilon}_{th}(t) - \hat{\varepsilon}_{th}(t-1)) + (1-\lambda)b(t-1)$$

$$\hat{\varepsilon}_{ms}(t) = \mu(\varepsilon(t) - \hat{\varepsilon}_{th}(t)) + (1-\mu)\hat{\varepsilon}_{ms}(t-\hat{\tau}) \; \forall t = 1, 2, 3, \ldots \quad (6)$$

where $\hat{\varepsilon}_{th}(t)$ and $\hat{\varepsilon}_{ms}(t)$ are the estimates of thermal and mechanical strains respectively. b(t) is a local slope term which can be interpreted as the rate of temperature rise. The parameters $\kappa$, $\lambda$ and $\mu$ can take any value between 0 and 1. In this paper, we chose $\kappa$, $\lambda$ and $\mu$ so that the squared sum of reconstruction errors ($\Sigma_t(\hat{\varepsilon}_{th}(t) + \hat{\varepsilon}_{ms}(t) - \varepsilon(t))^2$) is minimum. In Eq. (6), t is assumed to be discrete since US image frames are acquired at discrete intervals of time. When the expression $(t-\hat{\tau})$ is negative, it is replaced by $\tau$. Eq. (6) also needs initialization of b(0), $\hat{\varepsilon}_{th}(0)$ and $\hat{\varepsilon}_{ms}(i)|_{i=0:\hat{\tau}}$ which are obtained as following: (i) Compute the moving average of the original series $\varepsilon(t)$ between t=0:2$\hat{\tau}$ with window size $\hat{\tau}$. (ii) Ignoring the first and last $$\left[\frac{\hat{\tau}}{2}\right]$$

points, fit a linear trend to the moving averaged series. Extrapolate the fitted line down to t=0. The intercept of the extrapolated line at t=0 is $\hat{\varepsilon}_{th}(0)$ and the slope is b(0). (iii) Subtract the extrapolated fitted line between t=0: from the original series to get $\hat{\varepsilon}_{ms}(i)|_{i=0:\hat{\tau}}$. Once the initialization is complete, the system of equations (6) are solved for all following t with a march-forward approach until the thermal and mechanical strain estimates and $\hat{\varepsilon}_{th}(t)$ are $\hat{\varepsilon}_{ms}(t)$ obtained for the entire time series.

Materials and Methods

Numerical simulation of US-TSI of atherosclerotic plaque. The TSI process governed by equations (1)-(5) was numerically solved using the finite element (FE) method (COMSOL V.3.5a, Burlington, Mass.) for a plaque, the geometry of which is outlined in FIG. 16. In FIG. 16, the vessel with 8 mm inner diameter and 0.8 mm wall thickness contains a lipid pool that is 3 mm at its thickest portion with a 0.5 mm fibrous cap separating the lipid from the ~5 mm wide lumen (the dimensions are based on a typical plaque in human carotid artery). A 4 mm thick muscle layer surrounding the vessel provides additional stiffness against distension. Each type of tissue was assigned its typical thermal and mechanical properties as summarized in FIG. 15. Realistic heating and blood pressure data were used as inputs: (i) The US heat input was computed via Eq. (2) from the 3D pressure map of a commercial US linear array transducer (L 14-5/38, 6 MHz center frequency, SonixTOUCH, Ultrasonix Inc., Richmond, BC, Canada) measured in a water tank using a hydrophone (HNC, Onda, Sunnyvale, Calif.). (ii) The blood pressure of a subject with arrhythmia was taken from a clinical database. Although the material properties used in the FE simulation are based on literature review, no significant effort was made to mimic the exact in vivo physiological conditions. The purpose of the simulation was to test the feasibility of US-TSI+H-W in the presence of realistic US heating and arterial pulse pressure.

The simulation produced temperature rise ($\theta-\theta\_0$), thermal strain ($\varepsilon\_th$ (t)) and mechanical strain ($\varepsilon\_me$ (t)) as outputs. Synthetic 2D RF frame was constructed by convolving the measured point spread functions of the US linear array transducer (L14-5, 6 MHz, SonixTOUCH) with randomly distributed virtual US scatterers in the tissue geometry. The mechanical and thermal strains from the FE simulation were used to relocate the virtual scatterers, and subsequent synthetic RF frames were constructed in the same way. The total strain between the synthetic RF frames was computed through phase sensitive 2D speckle tracking and H-W was then applied to extract the thermal strain from the total strain.

US-TSI water tank experiments with arterial phantom. US-TSI+H-W was tested experimentally on a vessel-mimicking phantom connected to a pulsatile pump (model #1423, Harvard Apparatus, Holliston, Mass.). A hollow cylindrical phantom 120 mm long, 33 mm outer diameter and 12 mm thick, was fabricated with a three-layer shell—the inner and outer layers were made from 10% polyvinyl alcohol (PVA, Sigma-Aldrich, St. Louis, Mo.) while the 6 mm thick sandwiched middle layer was made from rubber (60% Hardener and 40% Plastic-Softener, M-F Manufacturing, Fort Worth, Tex.). In terms of sound speed change with temperature, rubber and PVA show similar behaviors as lipid and water bearing tissues respectively. To mimic the mechanical properties of plaque, PVA (which represents non-fatty tissue) was made stiffer than rubber (which represents lipid) by increasing the number of freeze-thaw cycles. Both PVA and rubber were seeded with US scatterers—cellulose powder (Sigmacell, 20 m, Sigma-Aldrich, St.

Louis, Mo.) for PVA and amberlite powder (150-300 m, Sigma-Aldrich, St. Louis, Mo.) for rubber. The phantom was placed in a water tank and connected to the pulsatile pump running at 60 RPM. The 6 MHz linear transducer connected to SonixTOUCH was used for both heating and imaging using an interleaved US pulse sequence described below. Each pulse sequence lasted for 100 ms and consisted of a 10 ms long imaging phase, a 40 ms long heating phase, and a 50 ms resting phase. During the imaging phase, beamformed RF data were acquired using standard diagnostic 0.16 s long B-mode pulses. After the imaging phase, 160 heating pulses (each pulse 2.56 s long with a repetition interval of 250 µs) were transmitted from the middle 64-element sub-array. In order to dampen the effects of undesired tissue motion due to acoustic radiation force (ARF) as well as allow the transducer to cool, a 50 ms waiting time was allowed after heating before acquiring a new RF data set. In all, the average heating duty cycle was (2.56 µs)/(250 µs)×(40 ms)/(100 ms)=0.4% (which is substantially low compared to ARF applications that needs about 15% duty cycle). A total of 40 frames were collected (corresponding to 40 US pulse sequence described above) and the entire US-TSI data acquisition took 40×100 ms=4 s (equivalent to 4 pump cycles). After collection, the RF data was processed using phase-sensitive 2D speckle tracking (2DST) to obtain the displacement fields between adjacent RF frames. The total strain field was computed through spatial derivative of the displacement field and H-W was applied to extract the thermal strain from the total strain. A second experiment was performed on the phantom with the pump off (i.e. there is no mechanical strain), all other conditions remaining the same. The thermal strain obtained with the pump off was compared with the thermal strain extracted using H-W.

US-TSI water tank experiment with excised human atherosclerotic vessel. Under IRB approval at University of Pittsburgh, a 40 mm long human atherosclerotic femoral artery was harvested from a consented patient during above-knee-amputation (AKA) surgery. The artery was connected to a pulsatile pump and the same US-TSI+H-W protocol described above for the phantom was followed. After data collection, the artery was fixed in formalin and embedded in a mold with OCT compound and placed in a −80 C freezer. The portion of the artery near the imaged section was then cut into 8-10 m thick slices and stained using Oil-Red-O to identify lipid rich areas. The stained image was observed under microscope (Olympus, IX81) using ×10 objective lens.

Results

Figure 17:
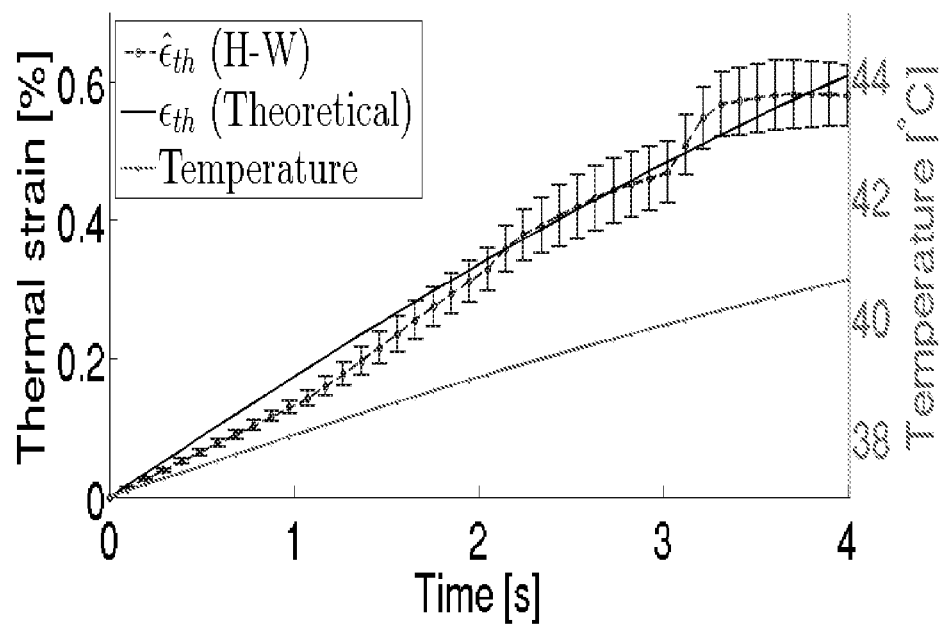
FIG. 17 shows the temperature, theoretical thermal strain, and the US-TSI+H-W estimate of thermal strain in lipid obtained via FE simulation.
Figure 18:
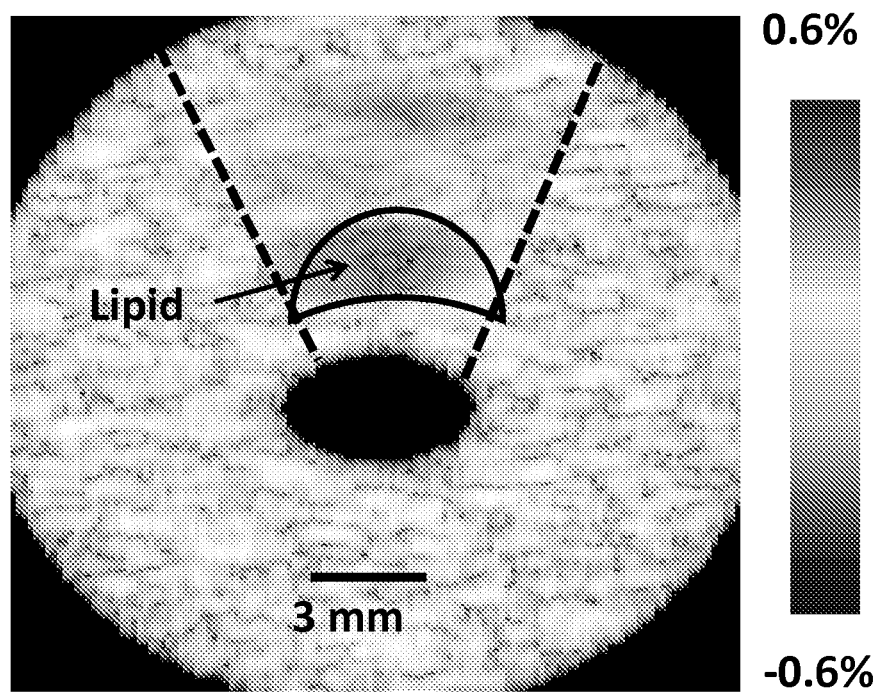
FIG. 18 shows the thermal strain image obtained via FE simulation and synthetic US-TSI+H-W. Dashed lines indicate the US heating beam (full width at half max.).

Numerical simulation of US-TSI. This subsection reports the results obtained from FE simulation and synthetic US-TSI+H-W. FIG. 17 shows that the temperature rise at a point in lipid in 4 s due to US heating is about 4° C. The corresponding theoretical estimate of the thermal strain in lipid is 0.6% (using=−0.15%). The US-TSI+H-W estimate of thermal strain stays close to the theoretical curve throughout the entire imaging time and neither converges to nor diverges from the theoretical value with increasing number of cycles. The error bars indicate variability of the H-W thermal strain estimate for five different synthetic speckle realizations. FIG. 18 shows the thermal strain image of the cross-section after 4 s. The lipid rich region shows positive (red) thermal strain while the water bearing part shows negative (blue) thermal strain (ref. FIG. 16).

US-TSI of arterial phantom. This subsection reports the results of US-TSI+H-W from vessel mimicking phantom connected to a pulsatile pump. The pulse pressure over one pump cycle and the corresponding total, mechanical, and thermal strains are reported in FIG. 19. The slightly positive thermal strain is totally suppressed by the strongly negative mechanical strain in the total strain image (FIG. 19B). However, after performing the time series analysis using H-W algorithm, the extracted thermal strain is clearly visible and shows a monotonically increasing trend (FIG. 19C). Similarly, the extracted mechanical strain shows an expected cyclic pattern (FIG. 19D). Note that the strain color bars differ for each row of images, and that the middle row, in particular, represent strains approximately one order of magnitude smaller than the other images. The line plots on the right show the corresponding average strains as functions of time (1 full pump cycle) around a 2 mm×2 mm region in rubber marked by x in the images on the left, with the error bars indicating spatial variability in the said region. Although a by-product of the time series analysis process, the mechanical strain is also useful to identify soft lipid pools. Due to the stiffness contrast with its surroundings, soft lipid pools can be identified with a high magnitude of mechanical strain—a fact that is used in ultrasound elasticity imaging (UEI).

Figure 20B:
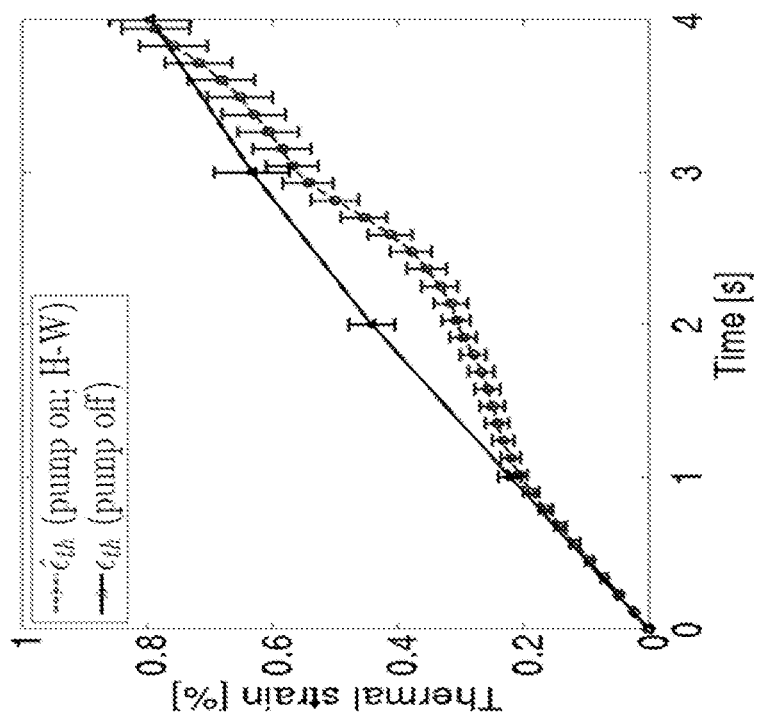
FIGS. 20A-B illustrate (a) total strain measured by US 2DST in a 2 mm×2 mm region in rubber when the pump was on and (b) comparison of the thermal strain extracted through H-W algorithm when the pump is on with the thermal strain obtained when the pump is off (when there is no mechanical strain).
Figure 20A:
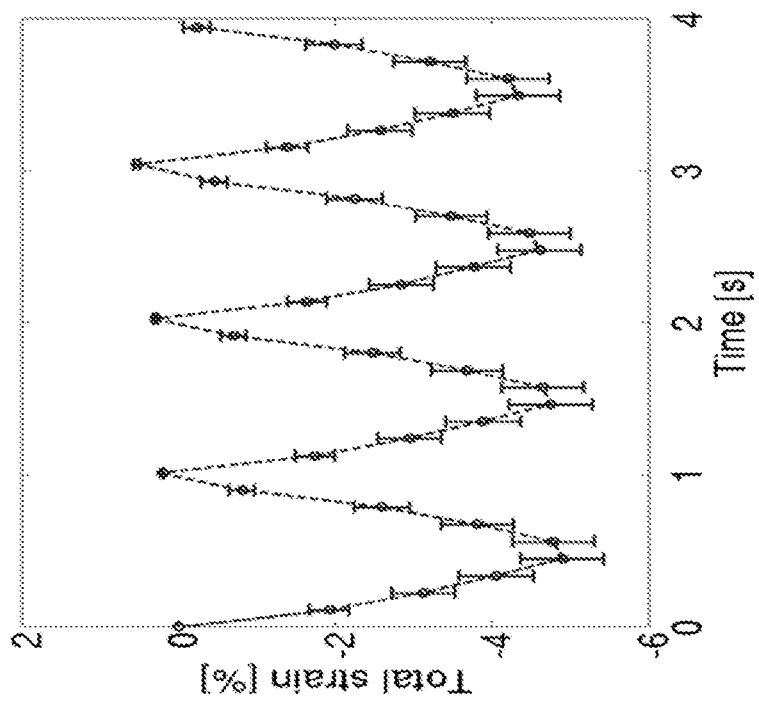

The total strain over 4 cycles in a 2 mm×2 mm region in rubber with the pump on is shown in FIG. 20 A. In FIG. 20B the thermal strain extracted via H-W with the pump on is compared with the thermal strain obtained via US-TSI only when the pump was off (i.e. when there is no mechanical strain). The error bars indicate spatial variability in the 2 mm×2 mm region. Somewhat higher thermal strain was observed when the phantom was static (i.e. the pump was off) throughout the entire imaging period. Note that the pattern of the thermal strain curves obtained via US-TSI+ H-W in FIG. 17 (simulation) and FIG. 20B (phantom experiment) are similar. Since the thermal strain developed in rubber during the 4 s of US-TSI is about 0.7% (FIG. 20B), assuming $\alpha=-0.15\%/°$ C. in Eq. (1), the expected temperature rise inside rubber would be 4.7° C.

US-TSI of excised human artery. US-TSI+H-W results from an excised atherosclerotic human femoral artery connected to a pulsatile pump are reported in this subsection. The thermal and peak mechanical strains extracted via US-TSI+H-W are shown in FIGS. 21A and B respectively. Oil-red-O staining of the imaged section is shown in FIG. 21C. A region in the vessel wall exhibits high positive thermal strain—indicating the presence of lipid which was confirmed by histology. The identified lipid area also exhibits high mechanical strain, indicating softness of lipid. The average thermal strain developed in the lipid rich region is about 0.75%. Assuming $\alpha=-0.15\%/°$ C. in Eq. (1), the expected temperature rise in lipid would be 5° C. FIG. 21D shows the thermal strain extracted using H-W in a 1 mm×1 mm region in lipid as a function of time, with the error bars indicating spatial variability in the said region.

Discussion

The data presented herein demonstrate that H-W successfully separates thermal strain from mechanical strain in the presence of pulsatile motion, which suggests the feasibility of US-TSI in conjunction with H-W algorithm to noninvasively detect large lipid pools in atherosclerotic plaques in the presence of cardiac pulsation. In FIG. 17, the US-TSI+ H-W estimate of thermal strain deviates slightly from the theoretical curve (about 4% in average over 4 s) obtained from FE simulation with realistic US heat and blood pressure inputs but otherwise ideal conditions. The deviation is due to errors induced by aperiodicity in the typical clinical blood pressure data and also by inaccuracies in speckle tracking. (In the hypothetical case where the blood pressure is precisely periodic with a constant period, the average error over 4 s was found to be as small as about 1.5%.) These deviations can be smoothed if wished by using appropriate physics-based filters based on the bioheat equation (a simple linear fit would have been inadequate to represent the thermal strain trend in the presence of heat dissipation as suggested by the bioheat equation). The advantages of using the H-W algorithm are: (i) It can extract the thermal strain within three to four cardiac cycles (i.e. about 4 s) which is reasonable for clinical applications. Since the H-W theory does not suggest that the extracted thermal strain will either diverge or converge to the true value with increasing number of cycles, there is no justification for using more than three to four cardiac cycles or as long as it takes to increase the tissue temperature sufficiently. (ii) The algorithm does not make any prior assumption about the shapes of the thermal and mechanical strain curves, both of which are expected to vary from patient to patient depending on the composition and structure of the plaque and the artery as well as the patient's heart condition. (iii) The H-W algorithm can work with relatively low frame rate (a frame rate of ten times the pump rate was used in our simulation and experiments—it would translate to ~10 Hz for clinical application considering human heart rate of ~1 Hz). US-TSI using a single transducer is limited to low frame rates since roughly 50 ms wait time must be allowed after each US heating cycle in order for the transducer to cool and also to dampen the effects of ARF if any. Therefore, an algorithm such as H-W that can work with low frame rates is very advantageous for US-TSI.

A few studies have reported observing a linear trend in the noninvasive US displacement measurement of the arterial wall in vivo even in the absence of heating (see for e.g. [36]). In [36], this trend was attributed to the sliding of the transducer on the skin of the patient due to hand movement of the operator. Since the metric of interest in our study is strain (which is the spatial derivative of the displacement), it is expected that any translational artifact due to transducer movement would be annihilated through the spatial derivative. As a general note, a trend in displacement does not automatically translate to a trend in strain. We did not observe any such trend in the strain signal in our in vitro experiments when the US heating source was absent. Therefore, within the scope of the current study, we assume that the trend in strain is caused mainly by the US speed change due to temperature rise (thermal strain). The current paper does not prescribe any compensation method for breathing induced strain artifacts. Such artifacts can be avoided in the clinic by asking the patient to hold his/her breath during US-TSI data collection for about 4 s with current design.

Experimental data from FIG. 20B shows that the thermal strain generated at a point in rubber with the pump off was somewhat higher than that with the pump running (about 25% deviation in average over 4 s). A possible explanation is that with the pump on, the point under consideration moved in and out of the US heating zone due to pulsation. Therefore, the average heating experienced by the point in the moving phantom might be lower compared to when the pump was off. Closer examination of the transducer pressure profile measured by hydrophone and 2DST displacement of the phantom could explain only about 10% difference in the total heat deposit. A major reason behind the deviation in FIG. 20B, therefore, remains unexplained. For in vivo applications, one must take this effect into consideration while designing the US heating beam.

Although the temperature rise in the in vitro experiments were not monitored directly using a temperature sensor, indirect temperature estimates from the thermal strain from FIGS. 20B and 21A indicated that the temperature rise due to US is around 4.6° C. in rubber and 5° C. in lipid. (The temperature rise in a different rubber phantom monitored using a thermocouple under the same transducer setup confirmed about 4-5° C. rise in 4 s). According to the American Institute of Ultrasound Medicine, no significant, adverse biological effects are expected for temperature increase of 5° C. if the exposure time is less than 2 minutes (for 4° C. rise, the corresponding allowable exposure time is 16 minutes). Since US-TSI of current design takes only about 4 s (plus a few tens of seconds for the tissue to cool down to normal body temperature) the technique is deemed temperature-safe. Also, the measured mechanical index (MI) for US-TSI was found to be 0.96, which is well below the FDA maximum allowance of 1.9.

A noteworthy point about FIG. 21 is that it is hard to exactly match the US imaging plane with the histology section even though surgical sutures were used for landmarking. Moreover, the imaging plane and the histology plane may be slightly skewed precluding an exact match. Multiple histology sections with 1 mm step that were stained around the imaging plane consistently show the presence of fat similar to what is seen in FIG. 21C; however, an exact match is not claimed.

Although noninvasive UEI can also detect large soft lipid pools in plaques, the results are sometimes difficult to interpret due to complex mechanical boundary conditions. US-TSI can provide complementary information to UEI, and the thermal strain image and elasticity image co-registered with US B-mode image can provide comprehensive information to assess the vulnerability of a plaque.

Conclusion

The above example demonstrates through in vitro experiments with phantom and excised tissue as well as computer simulation that H-W successfully separates thermal strain from mechanical strain, which suggests the feasibility of ECG-independent US-TSI to noninvasively detect large lipid pools in atherosclerotic plaques in the presence of pulsatile blood flow. The ECG-independent US-TSI can be implemented in a standalone commercial US transducer requiring only additional software installations: (i) to control US beamforming for inducing temperature rise, and (ii) to perform the signal processing for strain estimation and time series analysis as prescribed in the example.

Example 4—Integration of High Imaging Resolution and High Power Arrays for US-TSI In some embodiments, ultrasound-induced thermal strain imaging (US-TSI) for carotid artery plaque detection can be performed using both high imaging resolution (<100 μm) and sufficient US induced heating to elevate the tissue temperature (~1-3° C. within 1-3 cardiac cycles) in order to produce a noticeable change in sound speed in the targeted tissues. Since the optimization of both imaging and heating in a monolithic array design can be particularly expensive and inflexible, the following example provides a novel integrated approach that utilizes independent ultrasound arrays to meet the requirements for such applications.

As described below, in one embodiment, a novel dual-array construction provides a 3D printed manifold that support both a high resolution 20 MHz commercial imaging array and 6 custom heating elements operating in the 3.5-4 MHz range. For the application of US-TSI on carotid plaque characterization, the tissue target site can be 20 to 30 mm deep, with a typical target volume of 2 mm (elevation)×8 mm (azimuthal)×5 mm (depth). The custom heating array performance was fully characterized for two design variants (flat and spherical apertures), and, as described in detail below, can deliver sufficient total acoustic power (e.g., about 30 W or more) to produce intensities greater than 15 W/cm2 in tissue target region.

The flexible approaches described herein utilize independent US arrays that can be mechanically joined together in a low cost, high performance manner to suit a particular application. In one embodiment, a device can combine high resolution dedicated imaging array with a high power custom insonification array to produce a particular beam function. For example, an exemplary device developed for US-TSI can be configured to heat a 2×8 mm X-Y tissue region at a depth of 20-30 mm to achieve a 3° C. temperature rise quickly (e.g., in about 2 seconds) and permit simultaneous imaging with a wide band array.

Methods

Exemplary systems can comprise a custom array of elements mounted on a manifold to provide heating for US-TSI. This section includes a detailed description for the diverse spectrum of materials and methods employed in the prototype design process.

Figure 22:
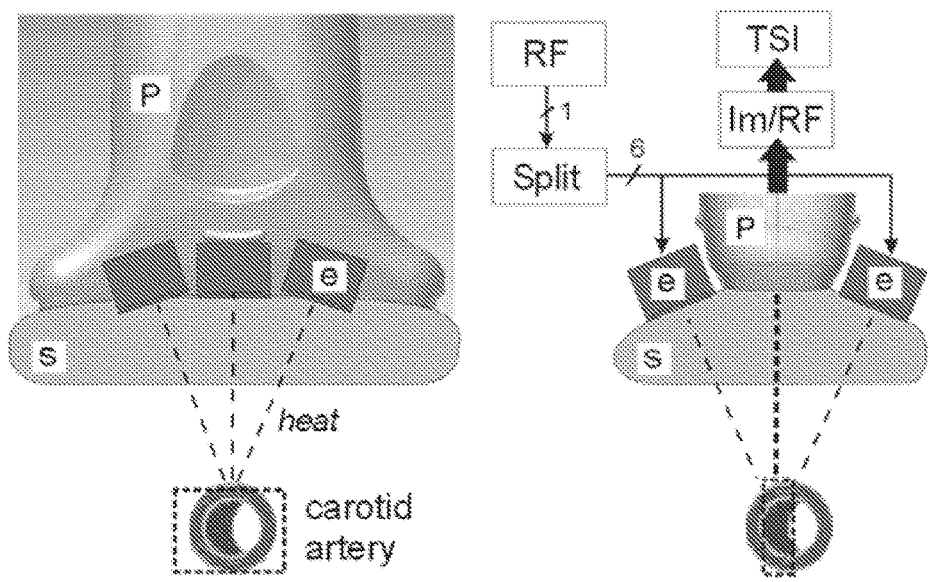
FIG. 22 illustrates an exemplary dual-mode US system for US-TSI.

Exemplary System. As shown in FIG. 22, an exemplary dual-mode US system for US-TSI is provided. The system can comprise an imaging array of choice (P), one or more US heating array elements (e), a single output power source (RF), and a splitter (Split). The A key contribution of this work is combining a 3D printed manifold designed to support and align the heating elements with a high efficiency RF power splitter which simplifies the power source requirements for this application. This heating manifold can be easily adapted to a chosen system. In this example, the flexible integration of the system was demonstrated using a commercial high-frequency ultrasound imaging system (Vevo 2100, FUJIFILM VisualSonics Inc., Toronto, Canada). In some embodiments, a linear heating array can be used. However, in this example, the system uses a collection of single elements, all driven with the same phase with overlapping beam foci. As discussed below, the frequency band of 3-4 MHz was used in order to conservatively optimize power delivery for a total beam path length of 35 to 40 mm and element sizes of 6-10 mm in order present a 50 Ohm load to the RF driving source.

Exemplary Heating Transducer Design and Construction. The heating transducer can be configured to provide a 3° C. temperature rise in about 2 seconds in a 2 mm×8 mm X-Y footprint with 5 mm or more depth while providing approximately a 50 Ohm electrical load to the RF source. In this example, a preferred operational frequency was first determined, then the size of the elements was selected, and, finally, the number and position of heating array elements were established.

(1) Determination of Heating Frequency and Element Size. It is assumed for simplicity the absorption coefficient, $\alpha$, is linear with frequency, the flat circular aperture with diameter D produces a natural focus at a depth $z=D^2/4\lambda$, where z is the total beam path to target from heating element, and $\lambda$ is the wavelength. The heating function is directly proportional to the product of beam intensity and absorption coefficient; however, an acoustic frequency change affects the magnitudes of absorption coefficient and intensity with opposing trends at a given depth. An estimate for an optimal insonification frequency can be found by solving $0=d[2\alpha I]/df$. The relative intensity at the focus, I, is $4\exp(-2a'Cfz)$. The frequency expression $\alpha'Cf$ replaces the absorption coefficient, $\alpha$ (in Np/m units). Thusly, the absorption coefficient, $\alpha'$ is in units of dB/cm/MHz, constant C is $(20\log(e))-1$, and f is in units of MHz. The estimate for the optimal frequency is:

$$f_{flat} = \frac{10\log(e)}{\alpha' z}, \quad (1)$$

where z is in units of cm. (Note that equations in the examples are independently numbered for convenience.) Early assessments were made for this best frequency, but some corrections were made using the average beam path absorption (e.g. $\alpha'=0.33$ dB/cm/MHz) which took into account a near field water stand-off path and a (total beam path) target depth of 37 mm from heating element. An preferred (e.g., optimal) frequency was determined to be 3.56 MHz using these calculations. The maximum frequency (or depth) calculation does not depend on the absorption coefficient at the heating depth, but rather the average absorption along the beam path before reaching the intended site at the heating depth.

After constraining the operating frequency to 3.5 MHz, the electrical impedance to 50 Ohms, and the total focus path length of 35 to 40 mm, an aperture diameter of 8.8 mm was chosen for a first set of flat aperture heating elements. To achieve an appropriate temperature rise, the intensity should be 15 W/cm2 in a 2×8 mm target region. Approximately ⅔ of the power is lost due to path loss and ¾ of the remaining power is lost due to beam diffraction. Using these assumptions (with detailed rationale described later), an estimated upper bound for total power from the entire transducer set was determined to be ~30 W total acoustic power for 2 second periods. As a result, a heating transducer set with six elements that each provided an acoustic power of 5 W was selected.

The above analysis was extended for the spherical aperture case. By combining the geometry of a spherical aperture and previously described optimal depth calculations, a preferred operating frequency for a spherical aperture can be determined. We examined the highly curved spherical aperture with kh>4. Here k is the wave number and h is the depth of the spherical aperture, or $z(1-\cos\theta)$. In this highly focused case, it can be shown that relative intensity at a focus depth z is $(kz)2(F(1-\cos\theta))2\exp(-2\alpha'Cfz)$ where F is the fraction of the active spherical surface and $\theta$ is the angle formed with a vertex at the geometric focus depth subtended by the spherical aperture centerline and a line from focus to aperture edge. The optimal frequency for delivering heat to a given depth z for a highly curved spherical aperture is:

$$f_{spherical} = \frac{30\log(e)}{\alpha'(z)}, \quad (2)$$

which is a very similar to (1) above. From (2), it is evident that the optimal frequency is three times the frequency predicted for a flat aperture, and (as shown in more detail later) this seems reasonable since the beam produced by the spherical aperture considered produces a beam energy density near its central axis which is a significant multiple of the flat beam.

(2) Transducer Modeling and Construction. The heating elements is preferably both capable of relatively high continuous acoustic power output with minimal internal heating and high heat capacity. Substantial increases in transducer temperatures (>60° C.) are not anticipated which permits the use of a simple design using a standard PZT-5H material with silver (Ag)-epoxy electrical contacts. An air backing is desired, but with an adequate front layer matching to assure front port transmission efficiency. Although narrow band operation is acceptable, a narrower bandwidth increases the difficulty in matching element output at a specific frequency; therefore a modest bandwidth was chosen to assure that all elements are within a 3 dB range.

Figure 23:
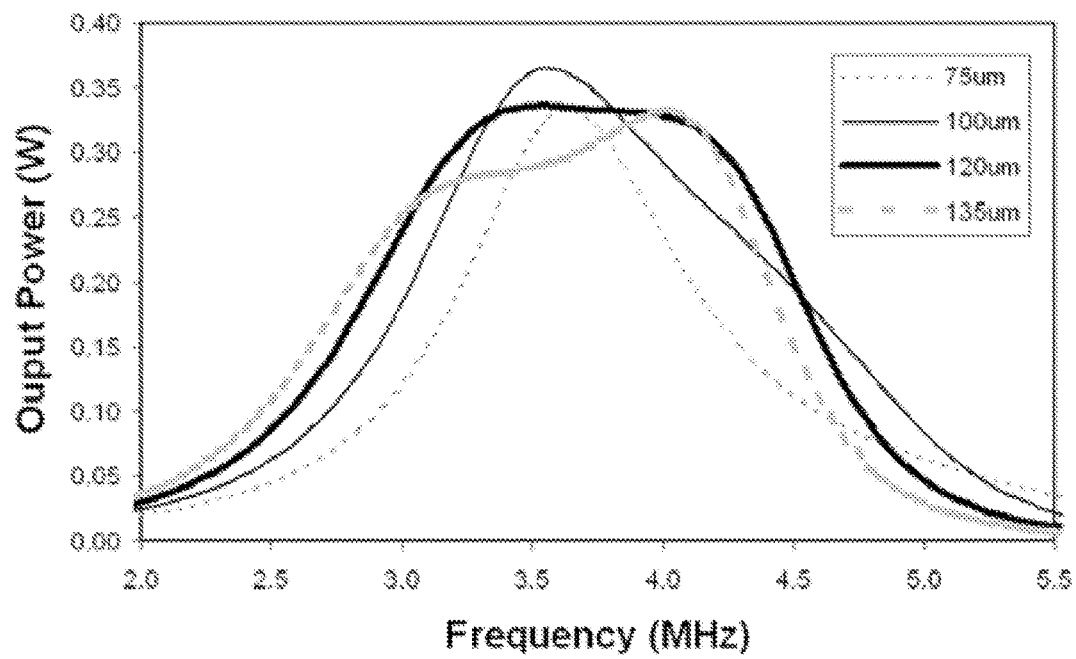
FIG. 23 illustrates KLM simulations showing spectral power band shapes for thickness ranges of Ag-Epoxy matching layer.

The transducer material (PZT-5H, Boston PiezoOptics, Bellingham, Mass.) was used with a thin Ag-Epoxy front matching layer (8331, MG Chemicals, Surrey, B.C., Canada) and a very thin insulation epoxy layer for protection (EpoTek 301, Epoxy Technology, Inc., Billerica, Mass.). A small thermistor (R805-103J-3518B, Redfish Sensors, Meridian, Id.) was mounted on the back side of the piezoceramic to monitor the core temperature of each transducer element. A KLM model served as a design tool and provided a means to verify the front layer thickness of each device by comparing the model (FIG. 23) to the spectral impedance (4396B, Agilent Technologies, Santa Clara, Calif.) during device bench testing. FIG. 23 illustrates KLM simulations showing spectral power band shapes for thickness ranges of Ag-Epoxy matching layer. The flat devices (3.5 MHz) targeted 100 µm thick and spherical devices (4 MHz) targeted 130 µm thick matching layers.

The Butterworth-Van Dyke (BVD) circuit model was useful to assist in transducer characterization. FIG. 24 shows the model used which was refined further with the aid of the more complete KLM model. FIG. 24 illustrates a simplified tank circuit model near resonance used to calculate the heating element electrical to acoustic efficiency. The cable used was 3 m, but had little effect as the transducer impedance magnitude was close to 50 Ohms (39 Ohms), and no tuning inductors were needed.

Attention was made to the spherical elements which were made after the earlier flat aperture prototypes with matching layer thicknesses in the 120 to 135 micron thick range to permit operation at a slightly higher frequency (at 4 MHz as determined earlier). With the values in the table shown in FIG. 25, the complex transducer impedance Zxd was calculated to be 30.5−j24 Ohms at 4 MHz and the transmit sensitivity, Sxd, was determined to be approximately 17.5 kPa/V. For these values, Ra and Rd values in the model (FIG. 24) are 45 and 73 Ohms, respectively. The voltage Vs necessary to produce a desired acoustic output power magnitude (Pa in Watts) can be found using equation (3).

$$P_a = \frac{(V_s S_{xd})^2}{2}\left|\left(\frac{Z_{xd}}{R_{out} + Z_{xd}}\right)\right|^2 \frac{A_{xd}}{Z_w} 10^{-4}, \quad (3)$$

where Rout is the generator output impedance, and Vs the peak voltage inside the generator which is equal to twice the peak voltage across a Rout dummy load (i.e., 50 Ohms) used to calibrate the source. Zw is the acoustic impedance of water and Axd is the area of the single element transducer. The effect of the cable was not considered in the calculation for reasons discussed below.

This acoustic power can now be used to find the dissipative power from the total electrical power and the expected reactive power component. First, the total electrical (i.e., apparent) power delivered to the transducer element is the product of the voltage and current magnitudes with its complex plane operators using the radian angle difference between voltage and current as θv−θi. This total power is $$P_e = \frac{V_s^2}{2}\left|\frac{Z_{xd}}{(R_{out} + Z_{xd})^2}\right|e^{j(\theta_v - \theta_i)}, \quad (4)$$

and the dissipative power is the real part of this total electrical power minus the acoustic power found in (3). The reactive power is the imaginary part of the apparent power. The power factor, which is ideally unity, is the ratio of the real power and the apparent power. Since the power factor in this design is approximately 0.78 with an element impedance magnitude close to 39 Ohms, there is relatively little use for inductor tuning to remove the effect of the cable capacitance. The only issue with a longer cable is the minor impact of the increased effective series cable resistance.

Figure 26:
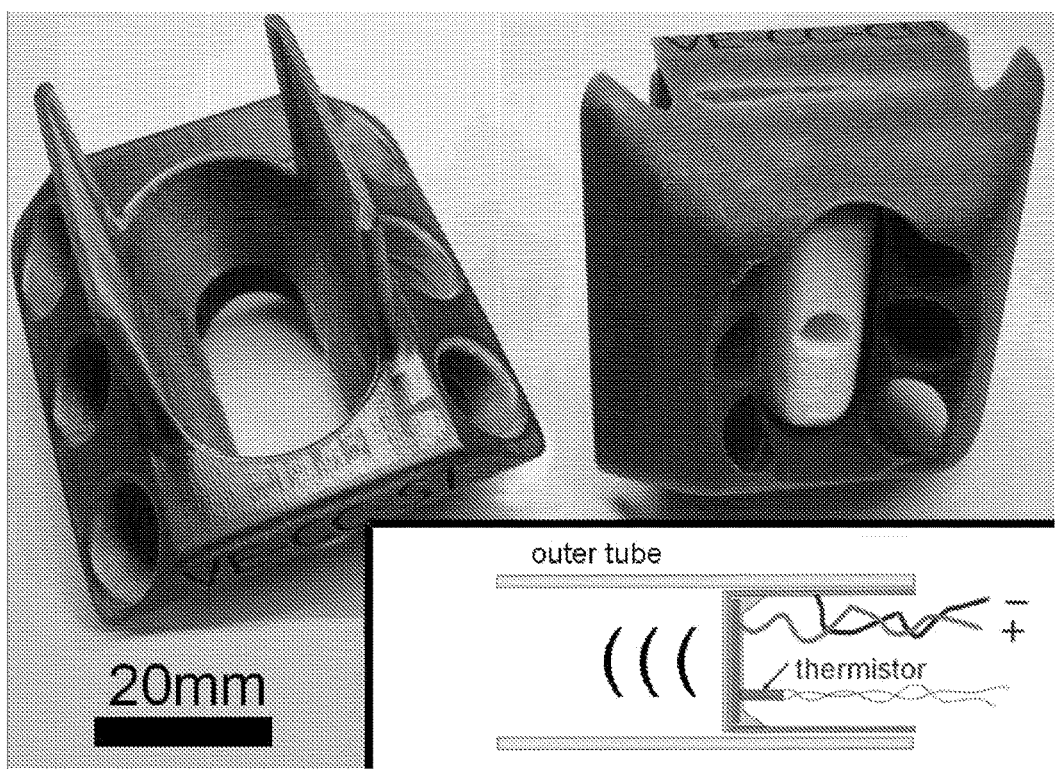
FIG. 26 shows an exemplary 3D printed array manifold.

Exemplary Heating Array Manifold Design and Construction. The exemplary 3D printed array manifold shown in FIG. 26 was constructed at the UC Davis Department of Biomedical Engineering TEAM prototyping facility using a 3D printer (Objet 260v, Objet Inc., MN). A shown in FIG. 26, (a) shows an individual circular element recessed in its alignment tube, (b) shows the manifold from the top showing the precision formed bay for the MS250 imaging probe body, and (c) shows the bottom with a plaster probe dummy where the imaging probe resides.

Figure 27:
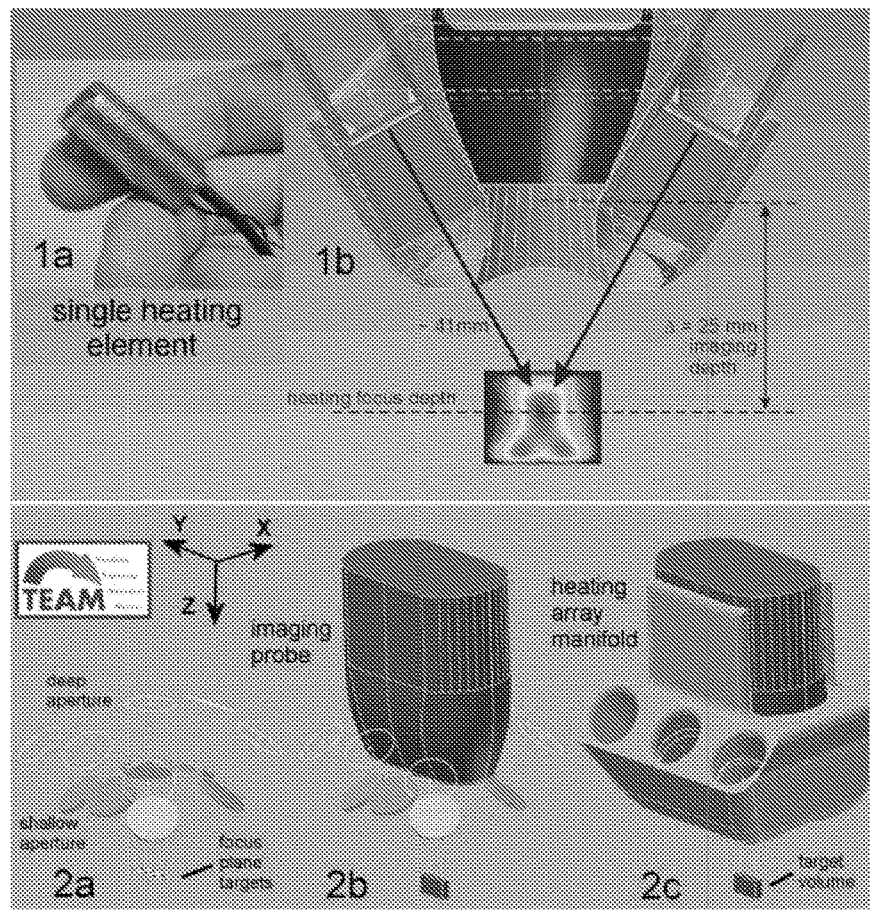
FIG. 27 illustrates individual heating elements and a heating array manifold for the same.

A 3D software casting of the imaging probe (MS250, FUJIFILM VisualSonics Inc., Toronto, Canada) was acquired by laser scanning (3D Scanner HD, NextEngine, CA). Based upon the 3D acoustic beam performance from simulations, the aperture positions of the heating elements were determined and a CAD design of the manifold was created with cavities to accommodate the imaging probe and heating array elements (FIG. 27). FIG. 27 illustrates each of the 6 individual heating elements (1a) inserted into the manifold (1b) to permit insonation of a heated region (X-Z heating plane is shown) in the tissue while allowing clear visualization with a imaging transducer. Each heating element positioned in a recessed location 16 mm deep at the rear of the gel-filled metal tube (i.e., "deep aperture," in 2a). The dark rectangular "target volume" (2b, 2c) describes the 2 mm by 8 mm by 5 mm heating target site. The CAD output can be exported as a stereo lithography (STL) file in point mesh format for use by the 3D printer. The part can be printed, water jet cleaned, and ready for immediate use.

Figure 28:
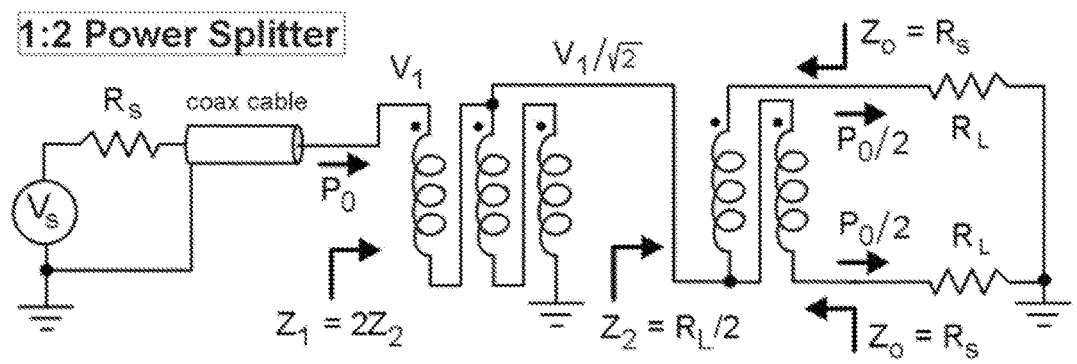
FIG. 28 illustrates a core 1:2 power splitter design that can be cascaded in three stages to provide a 1:8 overall power split.

Power Distribution Electronics. Although driving all the heating elements in equal phase will produce a fine grating lobe structure in the beam field, this will not result in major disadvantages in the production of mild hyperthermia. Thus, we chose to design a high efficiency power splitter driven by a single RF source. An RF power splitter design was chosen which offers relative simple construction, high efficiency, and the ability to be cascaded to create any 2N outputs. The design is shown in FIG. 28 using ferrite toroids (FT-114-61, Amidon, Costa Mesa, Calif.) with trifilar and bifilar winding. As shown in FIG. 28, the core 1:2 power splitter design can be cascaded in three stages to provide a 1:8 overall power split. A two stage design can offer the 50 Ohm impedance as both input and output impedances, which can help assure efficiency.

The output impedance of each power splitter port can be the same as the driving source impedance which makes this design easily cascadable. This splitter has better than 99% efficiency, 1 dB bandwidth of approximately 150 kHz to 8 MHz, and can accept over 100 W as an input with minimal signal compression. By creating an N=3 cascaded splitter arrangement, 8 outputs are available. The two unused outputs were terminated in 50 Ohm power resistors to maintain a balanced output for the other 6 splitter ports. The 1:8 power splitter is driven by a single RF source (Model 100A250A, Amplifier Research) which is capable to deliver over 100 W of RF output with less than 1 dB compression distortion.

Acoustic Heating Analysis (Flat vs. Spherical Elements). A heating array comprised of 6 elements with 2 mm nominal focal beam diameters is expected to adequately heat a 2×8 mm XY region at a tissue depth of 20-30 mm with a total beam path length of approximately 35-40 mm. For this reason, beam steering was not needed in this early design. If the elements are spaced at a distance d in a particular dimension, the expected grating lobes will appear at intervals of $\lambda z/d$ for a given depth z and assuming $d \gg \lambda$. At 3.5 MHz with a z depth of 41 mm (i.e., long beam path length utilizing the recessed heating element position), the grating lobes are expected at intervals of approximately 0.5 mm and 1.0 mm in elevational and azimuthal directions, respectively.

Rather than a "diffraction loss" calculation, which describes the effective power loss in a "pitch-catch" transducer set as a function of separation, we define a similar normalized beam power integration which we use to find the relative beam focusing capability of an aperture at a particular depth of interest, $z_i$. The beam power fraction (BPF) at the target depth $z_i$ can be defined for a circular aperture as the normalized fraction of the total power in the axial symmetrical beam from zero at the centerline to a lateral dimension of $x_0$ by $$BPF(x_0, z_i) = \frac{\int_0^{x_0} p(r, z_i) p^*(r, z_i) dr}{\int_0^{r_0} p(r, 0) p^*(r, 0) dr}, \quad (5)$$

where r is the radius in the x-y plane at some particular depth, $r_0$ is the radius of the aperture, p( ) is the pressure field, and p*( ) is its complex conjugate. The BPF approaches unity as the lateral dimension x0 becomes large. The BPF is computed for both the flat and spherical aperture cases using the Rayleigh-Sommerfeld equation to calculate the pressure. The flat aperture BPF (at $z_i$=41 mm) and the spherical BPF (at $z_i$=30 and 41 mm) are shown in FIG. 29 at (d). FIG. 29 illustrates simulation comparisons of flat and spherical beam characteristics. With the same aperture diameter of 8.8 mm, the flat beam (a) and spherical beam (b) profiles show peaks at 44 mm and 30 mm respectively (fine dots), with dashed line depth indicating the approximate target depth of interest, or 41 mm. The lateral beam patterns are shown in (c). The BPF near the aperture centerline is plotted in (d). The black and gray dots in the lower panels are the −3 dB lateral distances for the flat and spherical beams respectively.

Flat and spherical apertures were compared. There are advantages and disadvantages to both: the flat aperture device is easier to construct and has a broader beam profile with less phase deviation. The spherical aperture device has a higher energy density as compared to the flat aperture and shows a comparable beam shape at a depth past the element focus depth (i.e., 41 mm, FIG. 29(c), (d). The "long path" (recessed elements in the manifold) was used for both aperture cases.

Using previously described methods, the Rayleigh-Sommerfeld (RS) equation was used to obtain a combined volumetric pressure field for the 6 elements. With regards to the flat aperture beam modeling, it is expected that a single beam focus will occur at depth $z=D^2/4\lambda$ with a focal intensity of four times the aperture surface pressure and a full width half power beam (FWHP) angle of approximately $\lambda/D$. For the spherical aperture, RS simulations show that a focus depth of about 28 mm is expected for an 8.8 mm diameter spherical aperture at 3.5 MHz with a radius of curvature (ROC) of 50 mm (FIG. 29). Since the ratio VD is small, the estimate for the FWHP beam width at the focus distance and beyond is $\lambda z/D$. At a depth of 41 mm, the −3 dB beam diameter is approximately 2 mm for both flat and spherical aperture beams, however the BPF profiles are quite different.

3D Thermal Modeling. It is desirable to find the power input necessary to achieve a 3° C. temperature increase in 2 seconds with uniform insonification over an 8×5 mm region in the Y-Z plane. A 3D, general heating simulation (Comsol Multiphysics, v3.2, Comsol Inc., Burlington, Mass.) has been constructed to accept both 3D acoustic simulation data as well as laboratory data. Unless otherwise specified, the initial temperature for all simulation results was assumed to be 37° C. The 3D bio-heat transfer equation (BHTE) simulation was able to accept input data as volumetric heat flux points either from RS acoustic models or from laboratory pressure measurements. Beam data from both flat and spherical aperture element sets were examined. In each case studied the aggregate echo path attenuation was assumed to be ⅔ of the initial transmitted power (net attenuation considering both gel and tissue lengths).

Heat loss through perfusion was ignored due to short heating durations. In addition, diffusion will also be limited over the brief heating duration because the diffusion distance in 2 seconds will be ~0.75 mm. The nominal diffusion distance can be estimated as the square root of tissue diffusivity (~1.4 E-7 m2/sec) multiplied by time. A 3D BHTE simulation volume of 10×10×8 mm in X-Y-Z dimensions was used and the volume boundary conditions were assumed to be at 37° C. The simulation mesh density was set such that the separation between points was less than 0.5 mm throughout the entire 800 mm³ volume. The tissue heating simulation input is a 3D pressure magnitude field result of all 6 elements. The 3D pressure data are converted into volumetric flux density, Q3D, by $$Q_{3D} = \alpha |P_{3D}|^2 (Z_w)^{-1}. \quad (6)$$

With a single iteration, the simulation aperture pressure could be scaled to achieve the criterion of a 40° C. maximum in the simulated tissue volume. In this manner, the YZ plane heating region characteristics as well as the required input power could both be determined for each test case. The 3D BHTE simulation computes the temperature elevation of tissue by assuming the form of the heat equation $$Q + \nabla \cdot (\kappa \nabla T) = C_v \frac{\partial T}{\partial t}, \quad (7)$$

where Q is the volumetric heat flux (W/m3) derived from the acoustic input data set and κ is the thermal conductivity. This expression however can be simplified to enable an estimate for the acoustic intensity required for the first few seconds (by ignoring conductive loss during these first few seconds), as $$2\alpha I = C_v \frac{\Delta T}{\Delta t}, \quad (8)$$

where α is the absorption coefficient (Np/m), and is assumed to be 25 Np/m at 3.5 MHz with an arbitrary frequency dependent tissue characteristic of 0.62 dB/cm/MHz. Using (8), an intensity of 12 W/cm2 was necessary given $Cv=4.07\times10^6$ J/m$^3$/° C. and assuming a 3° C. rise over 2 seconds.

Thermal Strain Imaging with a Phantom. An in vitro validation study of the US-TSI system was conducted by first assembling an imaging phantom of gelatin with a rubber inclusion as the TSI target. To make an approximately 6 mm diameter cylindrical rubber target for the phantom, scatterers (0.5% by weight Amberlite, 16641, Sigma Aldrich Corp, St. Louis, Mo.) were added to a hot (450° C.) liquid 80:1 mixture of plastic hardener/softener (M-F Manufacturing, Ft. Worth, Tex.) and allowed to cool. The cooled rubber cylinder was introduced to the liquid gelatin matrix. The gelatin matrix was made by combining gelatin (G-2500, Sigma Aldrich Corp., St. Louis, Mo.), water, and ultrasound scatterers (1% cellulose by wt, S3504, Sigma Aldrich Corp., St. Louis, Mo.). The physical properties of the test phantom are listed in Table II of FIG. 30. The properties for the rubber target were measured while those of gelatin matrix were estimated from the literature.

The TSI imaging/heating sequence used in the study has been described previously. It consists of standard B-mode imaging sequences interleaved with heating sequences. The phantom was imaged with the MS250 transducer on the Vevo 2100 system. The heating transducer was excited using parameters listed in Table III (which is shown in FIG. 30). Two-dimensional speckle tracking was applied on RF data to estimate displacement between a reference image and an image taken after heating. The apparent thermal strain is the derivative of displacement along short-time echo beams and was estimated using a 2nd order Savitzky-Golay filter. TSI was applied to the same phantom using both the spherical and flat elements.

Results and Discussion. RS derived axial and lateral responses for both flat and spherical aperture elements exhibited good agreement with laboratory acoustic measurements. The spherical element had a spectrum similar to spectrum for the KLM model with a 120 μm matching layer (FIG. 23).

Figure 31:
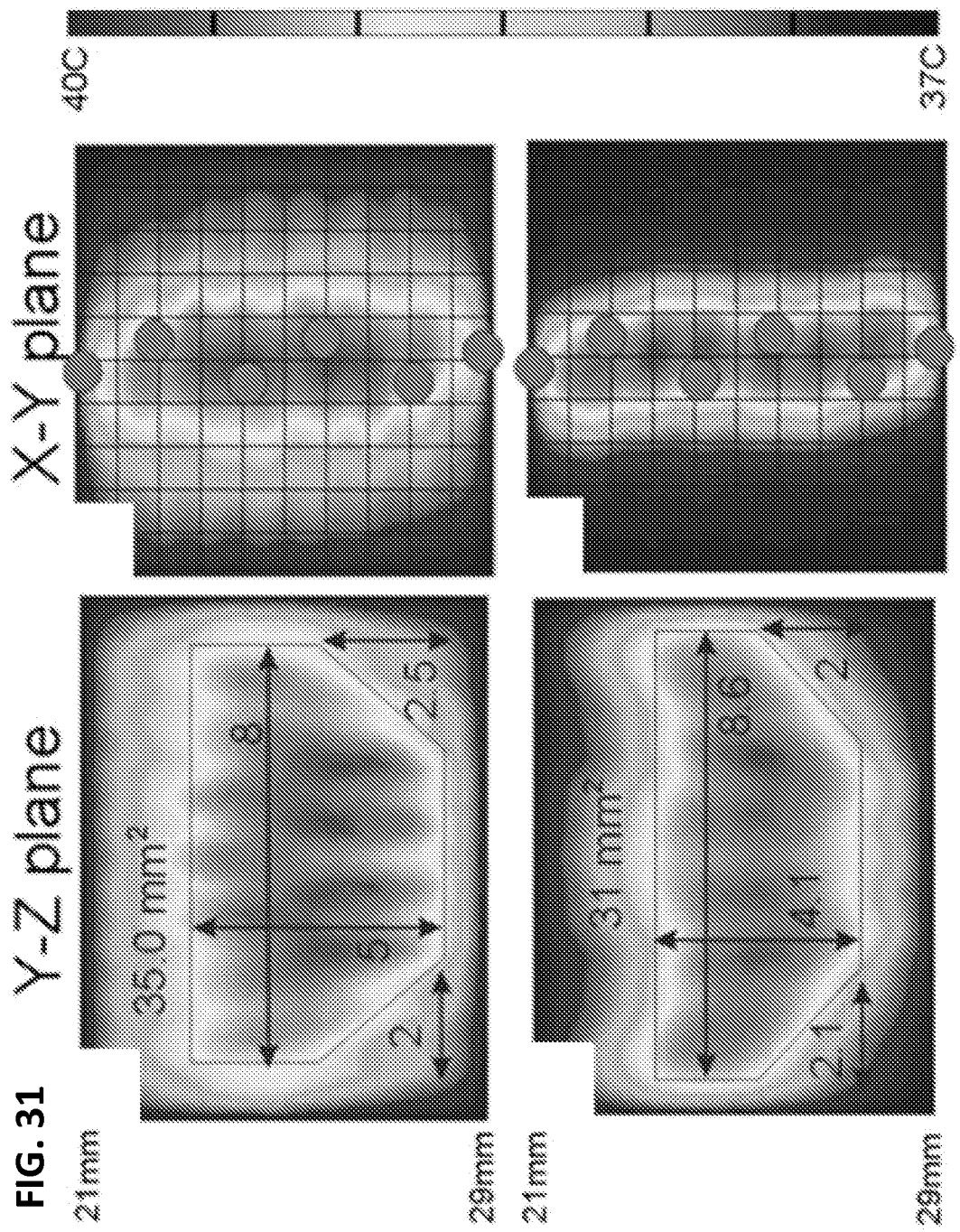
FIG. 31 shows a comparison of heating profiles for two different arrays.

Using the elements' spatial positions and simulated beam characteristics, the theoretical heating profiles for the two array types (FIGS. 31(a) and (c)) were examined to determine a reasonable set of element target foci. It was found that a staggered arrangement (FIGS. 31(b) and (d)) provided a good acoustic beam power coverage in the target plane. FIG. 31 illustrates orthogonal heating plane simulations for the flat aperture (a, b) and the spherical aperture (c, d) studies with planimetry. Blue dots represent the center focus target for a particular heating element. The entire temperature range plotted is 37° C. to 40° C. with planimetry borders defining the 39-40° C. regions.

Tables IV and V are presented in FIG. 32. The parameters necessary to achieve a 3° C. temperature rise in 2 seconds for the flat and spherical elements are summarized in Table IV. The modest peak pressures and MI indicate little concern for acoustically driven mechanical cavitation effects. The simulation derived average intensities in the heating region agree well with the calculation using (8). Table V shows the summary of simulation results on expected heating effectiveness. Approximate planimetry (FIG. 31) was used to assess the YZ plane area between 39° C. and 40° C. The "efficiency ratio" is a metric indicator showing the ratio of this YZ plane area and the total aperture power (Pwap) required to heat the desired target region. This metric shows that the spherical aperture design uses 56% less power to heat a similarly sized region as compared to the flat aperture design.

For every 1 W delivered to the transducer, the transducer converts 0.78 W into real power and 0.62 W into reactive power. The real power is divided into 0.48 W of acoustic power and the remaining of 0.3 W is lost to heat. These values were calculated using the modified BVD model (FIG. 23), and confirmed with both KLM and Comsol modeling as well as lab measurements. The thermistor mounted on the back of every PZT element provided laboratory readings to confirm the heat dissipation magnitudes predicted with an axisymmetric 3D thermal model of the transducer itself. Typical single element self-heating performance showed a PZT temperature elevation from 22° C. to 50° C. in 13 seconds at 2.5 W of dissipation and an output of 4 W acoustic power.

Using simulations and laboratory measurements for confirmation, a power flow link budget (FIG. 33) was assembled for both flat and spherical apertures to account for the translation efficiencies at each point in the transmission pathway. The laboratory pressure field data revealed a ~two-fold difference in overall power requirements between the two designs which agrees with the difference shown in FIG. 33. The numbered pathways in FIG. 33 have explanatory narratives which are presented here.

1. The 3 stage cascaded RF power splitter produces 8 outputs of which we only use 6.

2. This acoustic power is estimated from 3D BHTE modeling with 6 apertures. Individual beam estimates were computed using a 3D RS acoustic model. A single recursion approach with the BHTE model produces the estimated aperture pressure necessary to produce 3° C. temperature rise in 2 seconds.

3. The previously discussed transducer efficiency analysis has revealed that 48% of the input electrical power is converted to acoustic output, while 30% is dissipated as heat.

4. Reactive (imaginary) electrical power is approximately 62% of the total input power.

5. The fractional loss of acoustic power due to tissue absorption is calculated as $1-\exp(-2\alpha z)$ where a is an arbitrary 25 Np/m (0.62 dB/cm/MHz and 3.5 MHz) and a tissue path length of 22 mm is used.

6. The quantity of tissue heating power is derived both from a) the 3D BHTE simulation where the average acoustic intensity in the 2×8 mm X-Y target region is ~12 W/cm$^2$ and, b) the hand calculation of intensity neglecting perfusion and diffusion as in equation (8).

7. The beam loss is the acoustic power which is far enough from the heating target area such that it does not significantly contribute to heating. The beam loss fractional estimates are the result of total input acoustic power minus the power needed in the target region heating, and match reasonably well the beam characteristics shown in FIG. 29.

Figure 34:
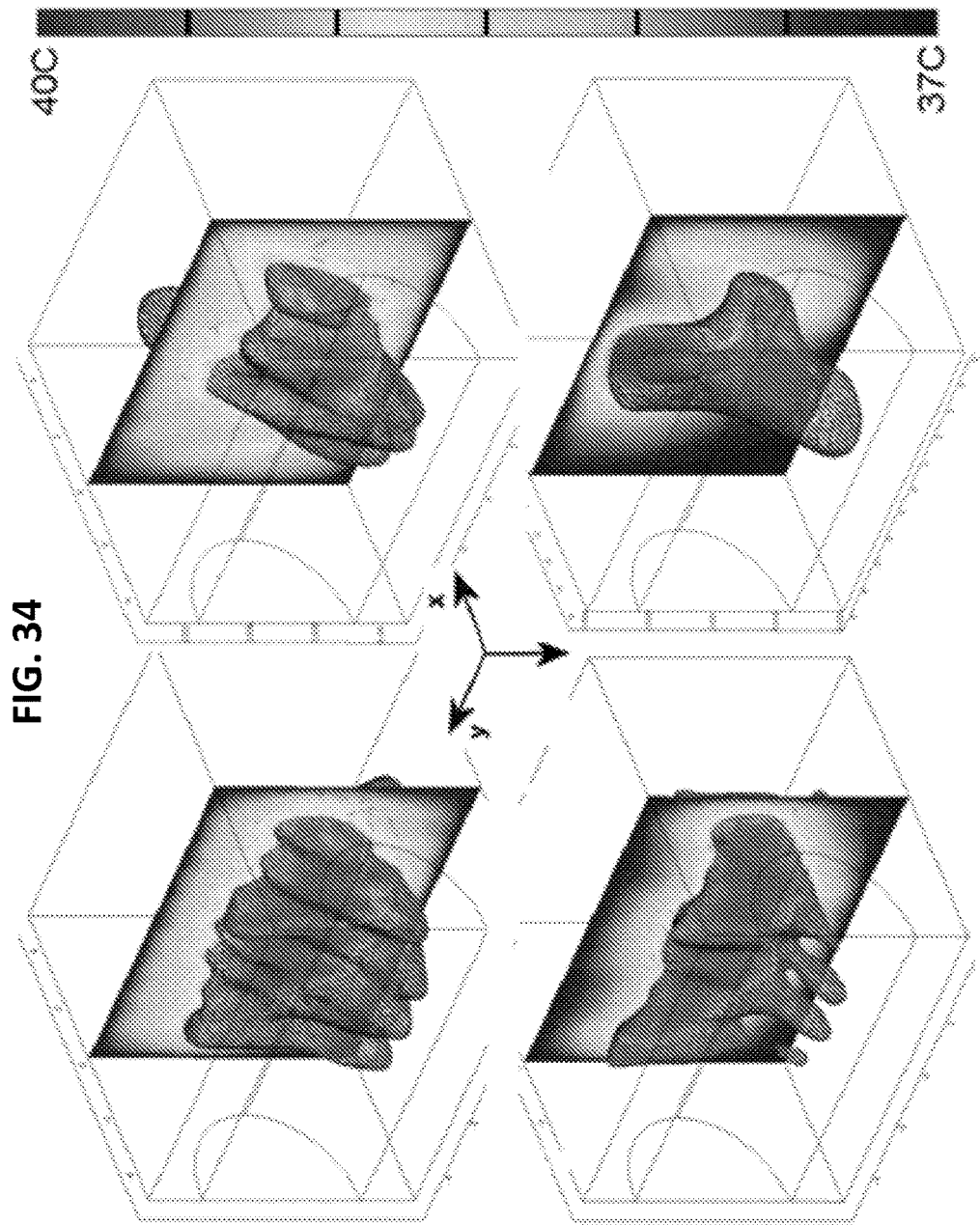
FIG. 34 shows target depth region BHTE volumetric heating results using 3D acoustic data sets.

Several early array manifolds were built with the 3D printer. Testing was completed with combined imaging and heating using a single RF power source and 1-input 6-output custom RF power splitter. The custom heating array acoustic and electrical performance was compared against KLM modeling and can easily deliver 30 W of total acoustic power which produces intensities beyond 12 W/cm$^2$ in the 2 mm by 8 mm target region. For tissue this would result in a 3° C. rise in temperature in two seconds. Custom beam modeling software was used to determine arbitrarily the beam target points for the custom arrays, and then implemented in the desired array manifold configuration. The flat and spherical aperture elements with the staggered manifold design were evaluated for their ability to produce effective and uniform heating in the desired target volume. The 39° C. 3D heating contour comparison of the flat and spherical elements is shown in FIG. 34. As shown in FIG. 34, the target depth region BHTE volumetric heating results using the 3D acoustic data set in each case are shown. The temperature range in this plot is 37° C. to 40° C. For each set, the peak temperature was limited to 40° C. in 2 seconds of insonation. The red isothermal surface in each is 39° C. with YZ imaging plane at center. (a) and (b) are the simulation and lab for the flat aperture array set; (c) and (d) are the simulation and lab for the spherical aperture array set.

Figure 35:
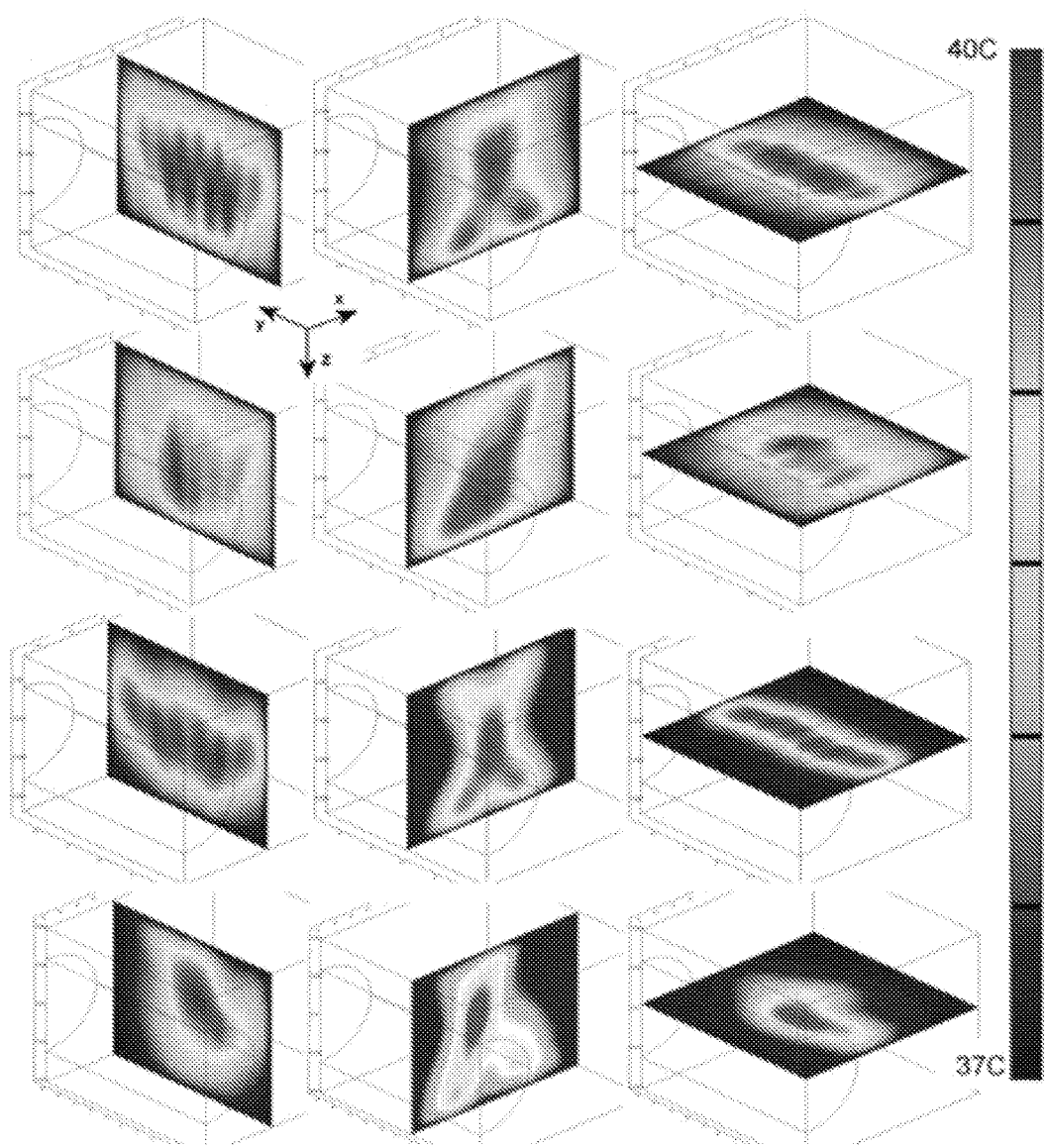
FIG. 35 shows the equivalent 2D heating planes for the same designs and conditions shown in FIG. 34.

The equivalent 2D heating planes are shown in FIG. 35. FIG. 35 illustrate the target depth region BHTE planar heating results for the same two designs and conditions as shown in FIG. 34. The heating planes are Y-Z (left column), X-Z (middle), and X-Y (right). FIGS. 35(a) and (b) are the simulation and lab for the flat aperture array set; FIGS. 35(c) and (d) are the simulation and lab for the spherical aperture array set, respectively. The manifold design fixes the position of the element such that only the rotation can be adjusted. Element rotation helped ameliorate beam skew errors but was unable to adequately compensate for all 6 beam positions as is evident from the undesirable beam skew in the right side of FIG. 35(d). In addition, it is apparent that the defocused flat aperture beam has a greater tolerance for beam skew as compared to the focused spherical beam despite the fact that the spherical beam is focused at 41 mm which is 37% greater than the individual focus of each spherical element (29 mm).

Figure 36:
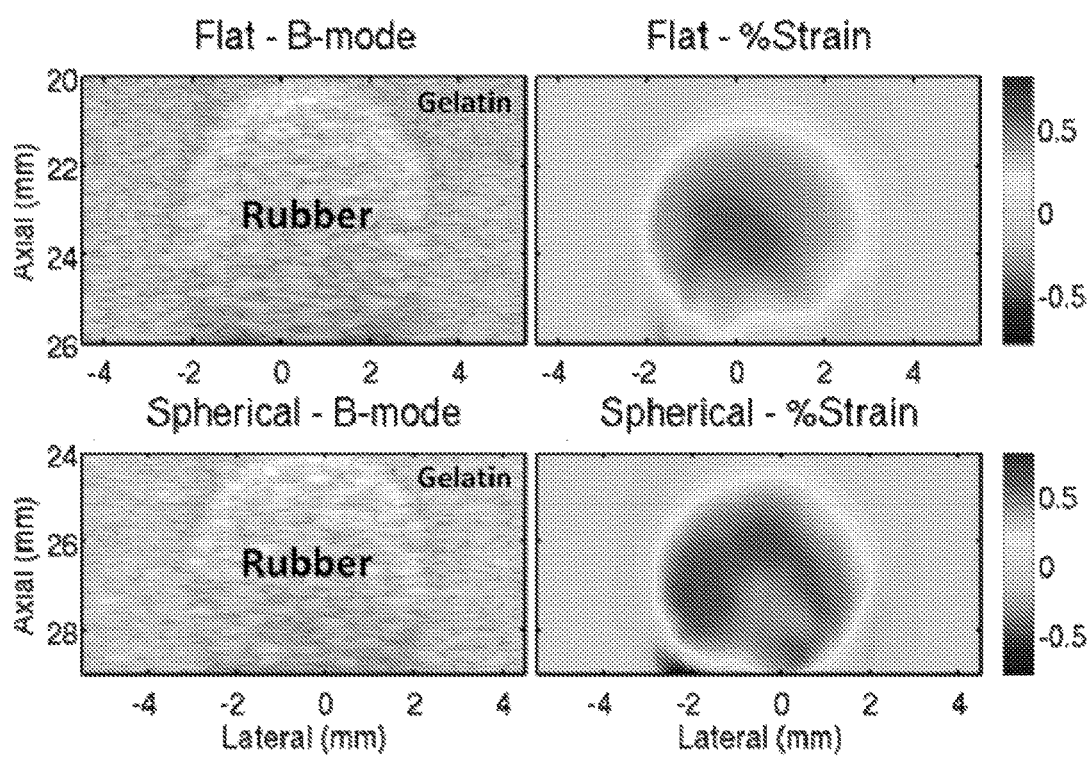
FIG. 36 shows B-mode and the corresponding US-TSI of an exemplary custom phantom for both flat and spherical aperture cases.

FIG. 36 shows B-mode and the corresponding US-TSI of the custom phantom with the 6 mm rubber inclusion for both flat and spherical aperture cases. In FIG. 36, both B-mode (left) and TSI images (right) of cylindrical rubber inclusion embedded in gelatin. The flat aperture array was used in FIGS. 36(a) and (b); the spherical aperture array for FIGS. 36(c) and (d). Rubber is known to produce a large, positive thermal strain when heated, whereas gelatin produces small negative thermal strain. This is evident in the US-TSI image with the rubber inclusion appearing red and the gelatin background appearing to be very slightly blue. The maximum thermal strain generated in the inclusion using the flat and spherical arrays was 0.59% for 0.5 sec, and 0.66% for 6.8 sec, respectively. Considering the ratio of thermal strain per unit time, the spherical aperture array generated about 12 times more thermal strain per second in comparison to the flat aperture array. This is a considerable difference and can be explained by a number of factors. First, the same electrical power, the flat elements deliver approximately half as much power to the target region. Second, the actual alignment of individual elements may be different between the water tank experiments used to generate the simulation data and the phantom experiments. Finally, the total time in which heating was applied to the flat elements is approximately five times as long as that used for the spherical elements. Over the course of 6.8 seconds, it is likely that the temperature rise with respect to time was no longer linear and that there were thermal diffusion losses. This illustrates two points: first, less efficient power delivery to the target region forces a longer heating time in order to obtain a robust and detectable signal and, second, as the length of time required to heat an object increases, the heating process becomes less efficient due to conductive loss of heat which is described by the BHTE.

The use of only 6 heating elements appears to provide enough power and beam uniformity to be useful for tissue heating and is still simple with respect to cost and complexity. Spherical heating elements can reduce the diffraction loss of a flat aperture beam and reduce the system power requirements, but this comes at the cost of a more precise beam alignment procedure. The main drawbacks with this heating array implementation are in element matching and beam alignment; the former can be addressed with robust manufacturing procedures, while the latter can be either solved through the use of more monolithic arrays, or by using approaches presented in the next section.

The US-TSI array manifold design is still in its infancy with several significant improvements to be made which will permit greater heating uniformity and ease of use. It has proven somewhat difficult to construct each element with a consistently accurate axial beam alignment. In the short term it will be essential to adjust the beam orientation ensure optimal performance. However, the design has already shown promise as it is currently being used for early TSI animal studies.

One way of ensuring proper axial alignment in the short term is to use a custom 3D film (25-30 C film, ThermometerSite.com, Glenview, Ill.) mounted in the X-Y plane at 25 mm in depth from the expected placement of the imaging array. The manifold, with a single element printed "cradle" for the manifold. The cradle supports a 15 mm by 20 mm thermochromic liquid crystal (TLC, 25-30C film, ThermometerSite.com, Glenview, Ill.) connected to an RF generator, is placed on top of the cradle in a water bath at room temperature. Using modest heating bursts (1 sec. on, 1 sec off), the TLC film will visibly indicate the location of the heating beam which permits easy adjustment of the individual element in the manifold with a precision of about 0.5 mm.

Tissue temperature tolerance is a significant concern, however this has been well studied over the last 20 years with guidance adopted by the American Institute of Ultrasound in Medicine (AIUM) [23]. For non-fetal tissue heating with 2 seconds of expected exposure, the AIUM standards predict the highest safe temperature rise to be 10.9° C. The safety margin of 7.9° C. is reasonable for this application. In an effort to monitor the heating exposure and to protect the transducers from overheating, an electronic controller is being designed to monitor the acoustic power delivery and provide tissue heating feedback to enhance safety.

One important reason to enable a US heating system with substantial power is to counter the substantial cooling effects of arterial blood flow close to the intended site of TSI. These effects have been studied which show very high heat transfer loss to blood. A short time, uniform, high intensity heating regime may be the proper means to permitting good TSI. This will be a major topic of interest as development of TSI for the carotid artery progresses.

This example demonstrates the feasibility to construct a low cost, highly flexible integrated solution in cases where typical commercial imaging systems cannot deliver enough continuous power into tissue for US-TSI. As described above, using this novel system a relatively small number of heating elements can be sufficient to achieve uniform heating in small regions. The application of spherically focused beams can also provide higher efficiency heating compared to flat beams and 3D printing of custom transducer manifolds may be a highly efficient means of developing a new "dual-mode" array paradigm.

Example 5—Additional Embodiments of Systems and Method for Detecting Fatty Livers As discussed above, this disclosure provides various quantitative approaches to diagnosing fatty livers using direct US thermal strain imaging (TSI). This technique is based on the different sound speed dependency on temperature rise between normal control and fatty livers. As sound speed changes with temperature rise, US echo signals shift in time and produce a temporal or thermal strain.

In the following example, US-TSI is used to differentiate between fatty and normal control livers in an ex vivo mouse model of NAFLD. Using a custom designed US-TSI setups, including beamforming and hardware a slight temperature increase of less than 2° C. was induced while capturing RF-US frames. Phase-sensitive speckle tracking was used to estimate small temporal shifts due to sound speed changes and then thermal strain maps of control and fatty livers were reconstructed and co-registered to B-scans. US thermal strain measurements were compared with oil red O histology for validation in order to determine the sensitivity and specificity of identifying fatty livers.

Methods and Materials

US-TSI was performed ex vivo to compare thermal strains measured in 10 fatty livers with those of 10 control livers. Fatty livers were excised from 10 obese (ob/ob) mice (7-13 week-old). It was reported that the ob/ob mouse model developed steatosis in 50% of hepatic cells at 7-weeks and 85% of hepatic cells at 13-week old. Control livers were excised from 10 wild type (C57B6) mice (7-13 week-old) fed with a normal diet.

Freshly harvested livers were embedded in 6% gelatin blocks (G-2500, Sigma Aldrich Corp., St. Louis, Mo.). One percent cellulose (S3504, Sigma Aldrich Corp., St. Louis, Mo.) was added to gelatin to generate US scatterers around the liver in order to avoid computational errors during signal processing. Then, US-TSI was performed at room temperature as described below.

Equipment

US-TSI requires acquiring US-RF imaging frames while gradually increasing tissue temperature. Two different experimental arrangements were used in this study for US-TSI. The first set was performed using a clinical US machine (SonixTouch, Ultrasonix Medical Corporation, Richmond, BC, Canada) that allows for custom pulse sequences and RF data access. Both US imaging and heating were performed using the same linear US transducer (L14-5/38, 5-14 MHz). The interleaved imaging-heating pulse sequence described in was slightly modified by increasing the waiting period after single heating-imaging sequence to 76 ms. An US transmit frequency of 6 MHz was used and B-mode image resolution was approximately 190 µm (axial)×300 µm (lateral).

Figure 37A:
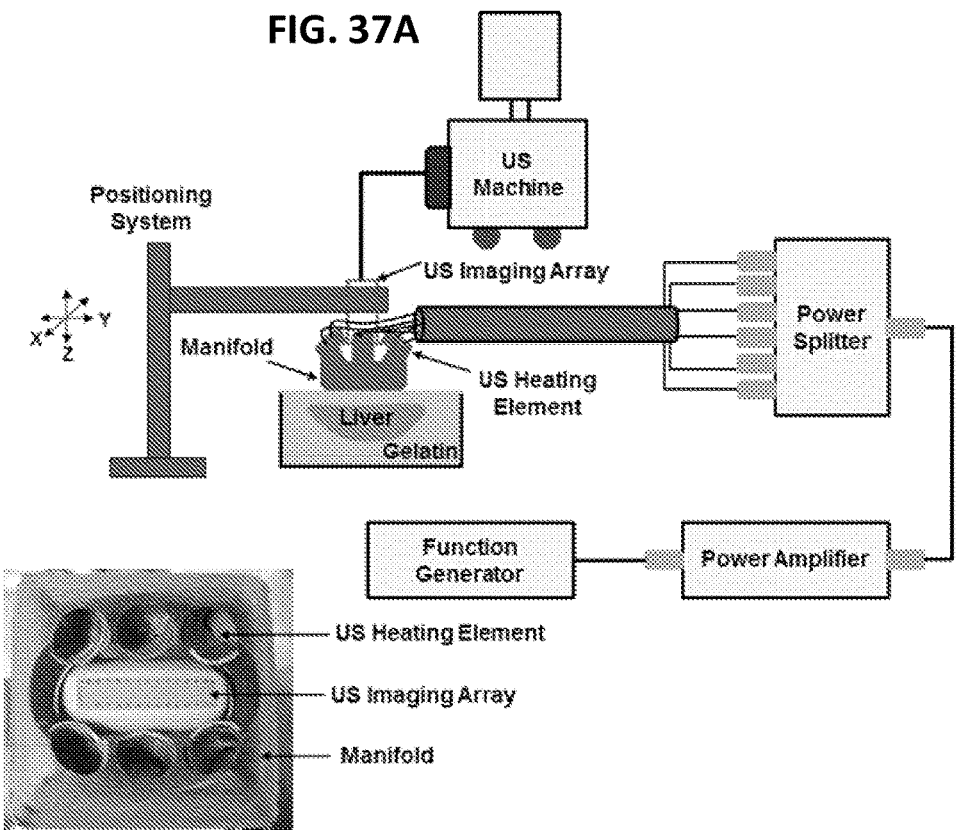
FIG. 37 illustrates an experimental configuration for ultrasound thermal strain imaging (US-TSI) with a schematic diagram (a) with an image showing the heating array manifold surrounding the high-frequency imaging array, and a timing diagram (b) illustrating an exemplary imaging-heating sequence.
Figure 37B:
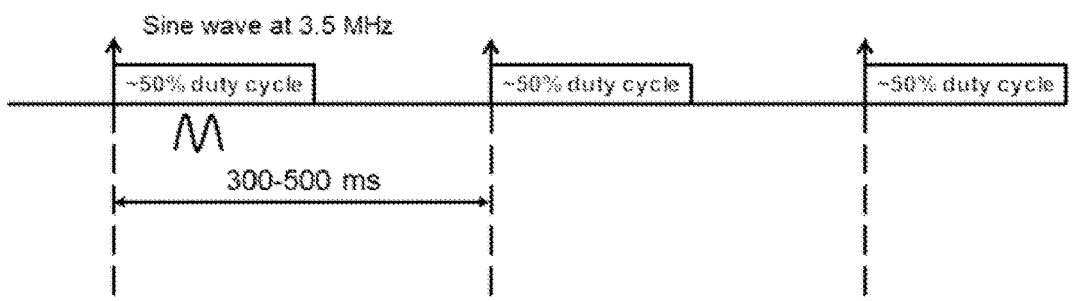

The second set of US-TSI experiments employed a more efficient heating scheme to scan 6 fatty and 5 control livers with higher imaging resolution. This was achieved by combining a high frequency US imaging array (13-24 MHz) of a small animal imaging system (Vevo2100, FUJIFILM VisualSonics Inc., Canada) with a custom designed US heating array that can achieve more efficient heating. FIG. 37(a) is a schematic of this experimental setup. A 3.55 MHz, 1.414 Vp-p sine wave was generated using an arbitrary waveform generator (33250A, Agilent Technologies, CA) and was fed into an RF power amplifier (100A250A, Amplifier Research, PA) to provide a 282.8 Vp-p signal (Gain=46 dB). Then, this heating excitation signal was divided equally on heating transducer elements via 1:8 power splitter. The heating array consists of 6 elements positioned equally on both sides of the imaging array in a custom designed manifold as described in the lower panel of FIG. 1(a). An imaging frame rate of 10 Hz was used while heating was performed using an average of ~50% duty cycle (FIG. 37(b)). An US imaging transmit frequency of 21 MHz was used and B-mode image resolution was approximately 70 µm (axial)×180 µm (lateral).

The first configuration using the clinical system produced a mean thermal strain of 0.15% in water-based tissues, corresponds to ~1.5° C. temperature rise, after 9.2 s, while the second configuration using the high-resolution system achieved the same strain after ~3 s. These heating periods were used for US-TSI of all livers.

Signal Processing

A 2D phase-sensitive correlation-based speckle tracking algorithm was applied to the US-RF data to estimate the temporal shifts associated with sound speed changes due to temperature rise. Temporal shifts can be seen in US frames as apparent axial displacements in the direction of US propagation. To measure these apparent displacements, a kernel that was approximately as large as the average speckles size was used to estimate the complex cross-correlation coefficients between two frames. Then correlation coefficient functions were digitally filtered to reduce the potential tracking error and the pick hopping probability. Axial displacements were then initially estimated from the position of the maximum correlation coefficient. Further refinement for axial displacement measurements were applied using the phase zero-crossing of the complex correlation function. The kernel size used for speckle tracking frames recorded by SonixTOUCH was approximately 200 µm (axial)×300 µm (lateral), while for high-resolution frames recorded by Vevo2100 it decreased to approximately 70 µm (axial)×180 µm (lateral). A correlation filter size of about 1.5 times the kernel size was used for both systems.

Thermal, or temporal, strains were computed as the spatial derivative of axial displacements along the axis of the US beam. Thermal strain maps for heated regions within the liver were color coded such that red and blue indicated the positive and negative strain respectively. Thermal strain maps were co-registered and superimposed on B-scan US images. Median filters of 0.58 mm (axial)×1.80 mm (lateral) and 0.12 mm (axial)×1.80 mm (lateral) were applied to SonixTOUCH displacement and strain maps, respectively. While for Vevo2100 frames, filer sizes were 0.55 mm (axial)×0.27 mm (lateral) and 0.11 mm (axial)×0.27 mm (lateral), respectively.

Histology

After completing US-TSI, livers were cleaned and fixed with formalin, embedded in molds of OCT compound, and frozen at −80° C. Sections (8-10 µm thick) were stained using oil red O and hematoxylin counterstaining for lipid staining. To quantify the percentage fat in livers approximately from histology, the red stained area in oil red O stains was computed and divided by the total area of the section. This analysis was conducted using Image J software (National institutes of Health, Bethesda, Md.).

Statistical Analysis

Statistical analyses were performed using the Statistics Toolbox of Matlab 7.12.0. All thermal strain values are expressed as the mean±SD. For each liver, thermal strain was measured as the mean strain within an area of 3 mm (axial)×3 mm (lateral) across 4 different elevational slices which were spaced 1-3 mm apart. Thermal strain measurements in control and fatty livers were compared using a two-tailed Student's t test. A p-value <0.05 was considered significant. Receiver operating characteristics (ROC) curve statistical analyses were performed using MedCalc for Windows, version 12.5 (MedCalc Software, Ostend, Belgium).

Results and Discussion

Using representative oil red O slides, percentage fat was estimated in each liver. Fatty livers exhibited a wide range of fat accumulation from 29.4% to 62.8%, whereas in control livers this percentage was less than 10%. US-TSI measurements in control and fatty livers were significantly different ($p<0.05$). Thermal strains in fatty and control livers were −0.065±0.079% and −0.124±0.037%, respectively, due to a temperature rise of approximately 1.5° C.

Figure 38A:
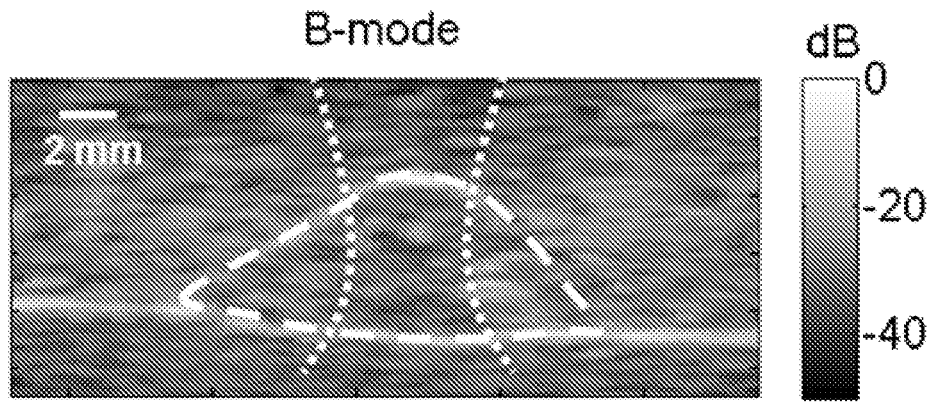
FIG. 38 illustrates ultrasound images acquired using a clinical ultrasound scanner for a control liver, including a B-mode image (a) of a typical cross-section in the liver (dashed contour). The dotted line shows the heating beam (from maximum in the center to approximately −3 dB at the boundaries).
FIG. 38(b) illustrates US-TSI for the section in (a)
FIG. 38(c) illustrates an oil red O histology for a cross-section within the liver.
Figure 38B:
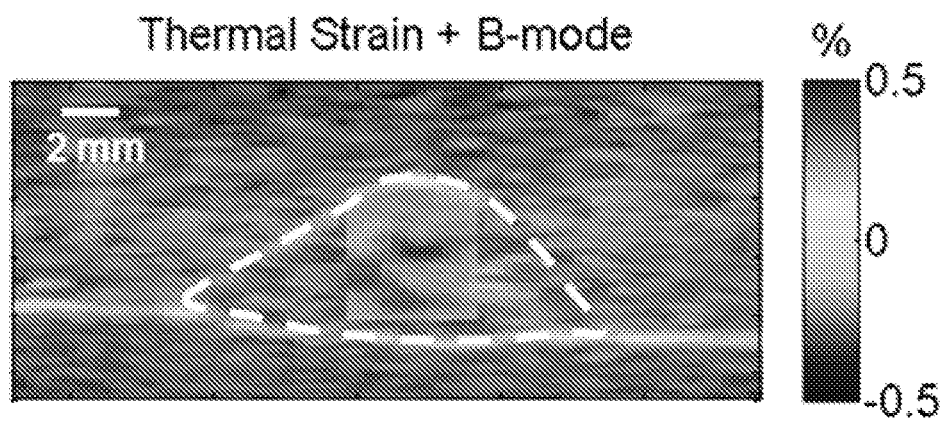
Figure 38C:
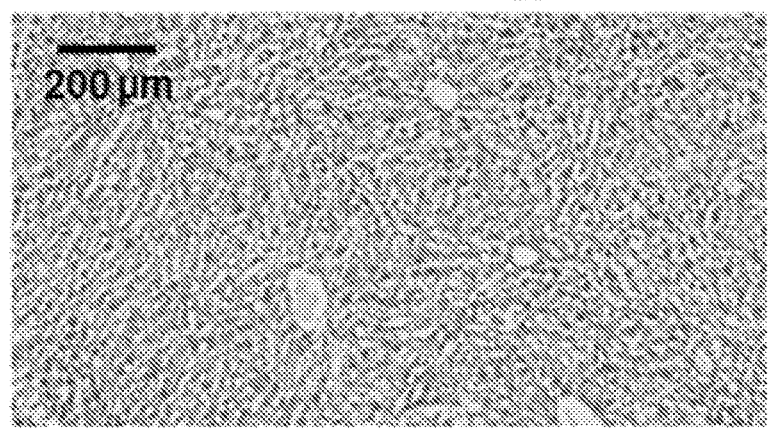

FIG. 38(a) shows conventional US B-mode image for a typical control liver, bounded by the dashed contour, embedded in gelatin. US-TSI was performed using the clinical system. Liver temperature was gradually increased while imaging using the US heating beam described approximately by the dotted line in FIG. 38(a) and subsequent figures. US-TSI was performed to the same section in FIG. 38(a) and the strain map was superimposed on the B-mode image as in FIG. 38(b). This control liver exhibited mostly negative strain of −0.158±0.037%. Oil red O histological findings of this liver (FIG. 38(c)) do not show noticeable fat accumulation as red color, which confirm its classification as control.

Figure 39A:
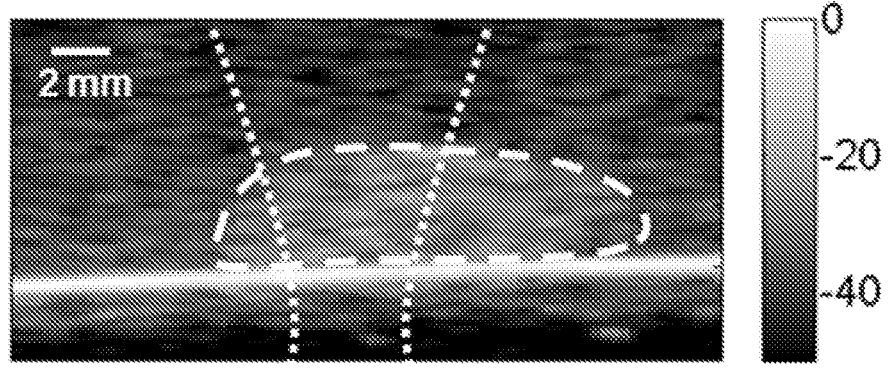
FIG. 39 illustrates ultrasound images acquired using a clinical ultrasound scanner for a fatty liver with FIG. 39(a) illustrating a B-mode image of a typical cross-section in the liver (dashed contour). The dotted line shows the heating beam (from maximum in the center to approximately −3 dB at the boundaries).
FIG. 39(b) illustrates US-TSI for the section in (a)
FIG. 39(c) illustrates oil red O histology for a cross-section within the liver.
Figure 39B:
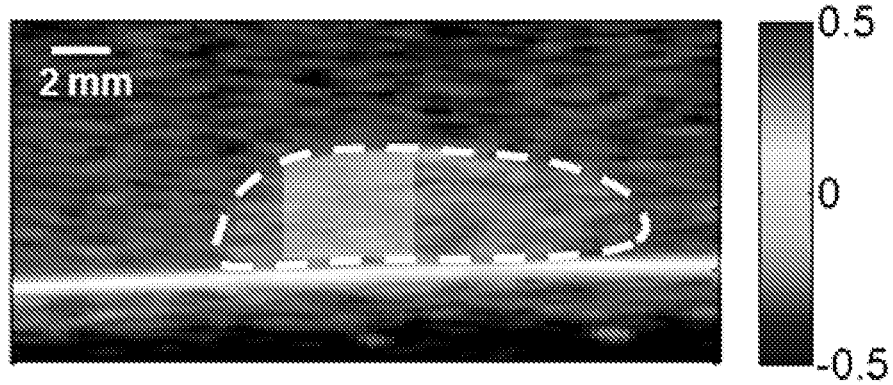
Figure 39C:
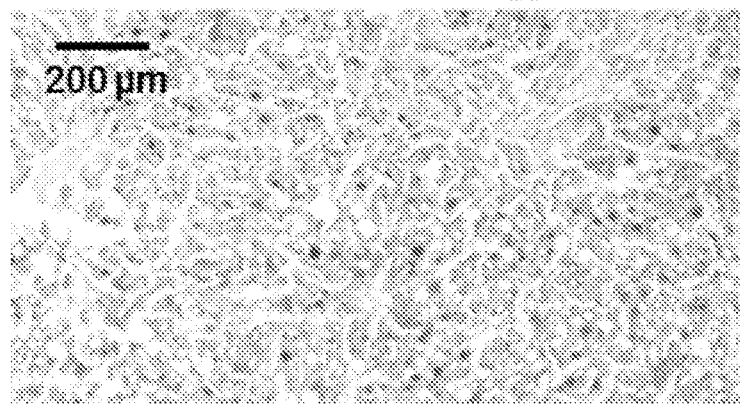

The same US-TSI procedures were applied to image a typical fatty liver using the clinical system. FIG. 39(a) shows B-mode image of the fatty liver bounded by the dashed contour. The corresponding US-TSI exhibited areas of positive and negative thermal strains as in FIG. 39(b) with higher strain of −0.070±0.007%. A strong red color staining was observed in the oil red O histology of this liver as in FIG. 39(b), which indicates increased fat accumulation.

Figure 40A:
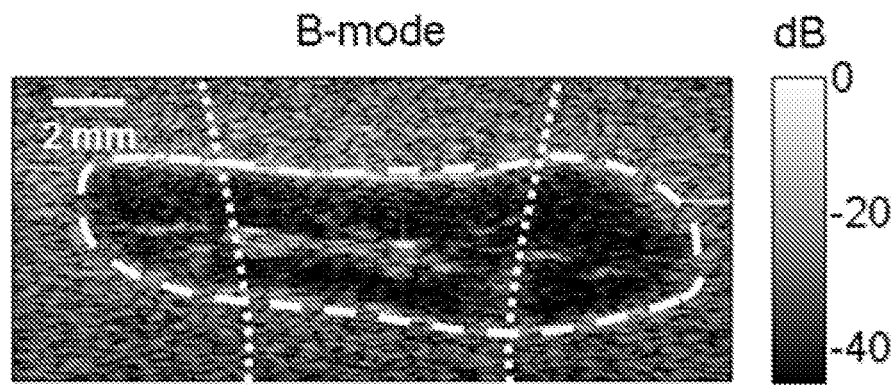
FIG. 40(a) illustrates a B-mode image of a typical cross-section in the liver (dashed contour). The dotted line shows the heating beam (from maximum in the center to approximately −3 dB at the boundaries).
Figure 40B:
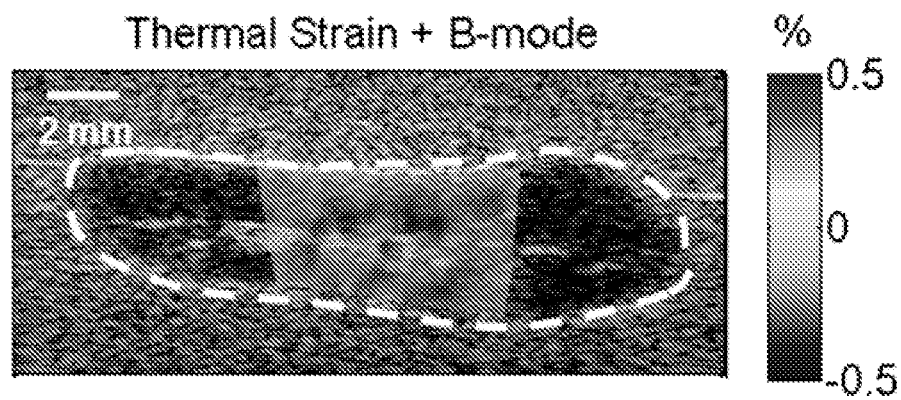
FIG. 40(b) illustrates US-TSI for the section in (a)
Figure 40C:
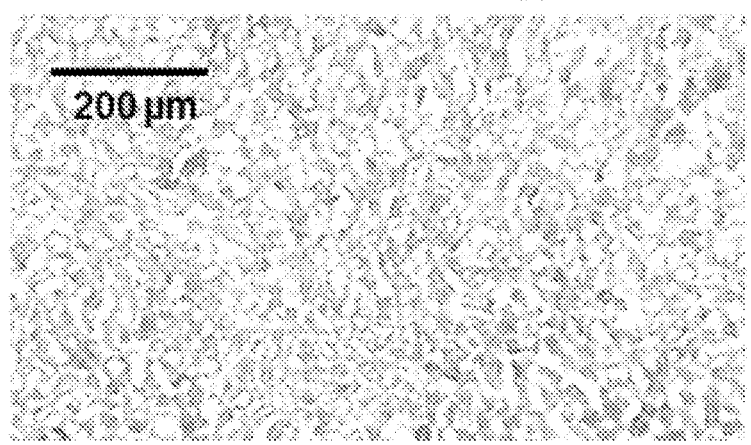
FIG. 40(c) illustrates oil red O histology for a cross-section within the liver.
Figure 41A:
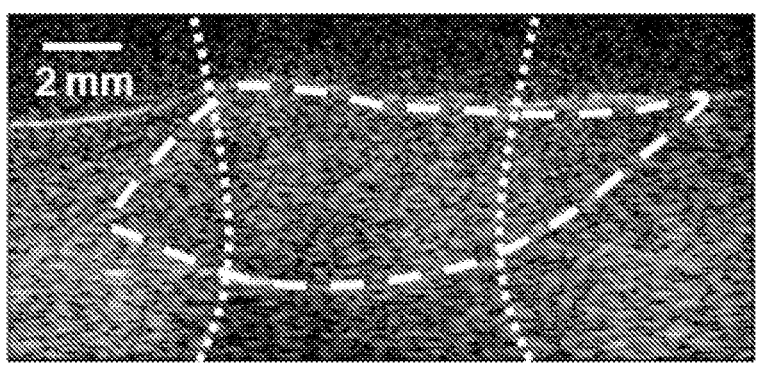
FIG. 41(a) illustrates B-mode image of a typical cross-section in the liver (dashed contour). The dotted line shows the heating beam (from maximum in the center to approximately −3 dB at the boundaries).
Figure 41B:
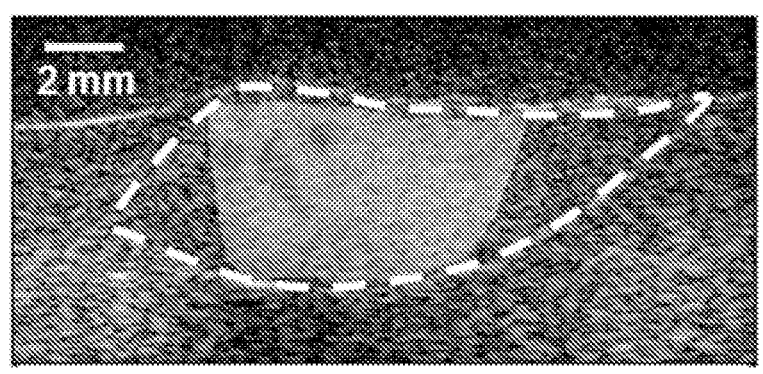
FIG. 41(b) illustrates US-TSI for the section in (a)

US-TSI was applied using the high-frequency configuration to reconstruct high-resolution US images while providing wider heating beam. Small anatomical details can be observed in the high-resolution B-mode image of the control liver in FIG. 40(a). The heating beam width of this configuration (FIG. 40(a)) was, at least, 3 mm wider than that of the clinical system. The corresponding US-TSI in FIG. 40(b) shows mostly negative strains and thermal strain of −0.118±0.023% was measured in this liver. Oil red O histology exposed predominantly blue color (FIG. 40(c)), which classifies the liver as normal. FIGS. 41(a) and (b) show high-resolution B-mode image and the corresponding US-TSI for a fatty liver cross-section. A positive thermal strain of 0.082±0.006% was measured in this liver, which reflects the dominant areas of positive strain observed in the US-TSI (FIG. 41(b)). Oil red O histology of this liver shows strong red staining due to increased fat accumulation.

Figure 42:
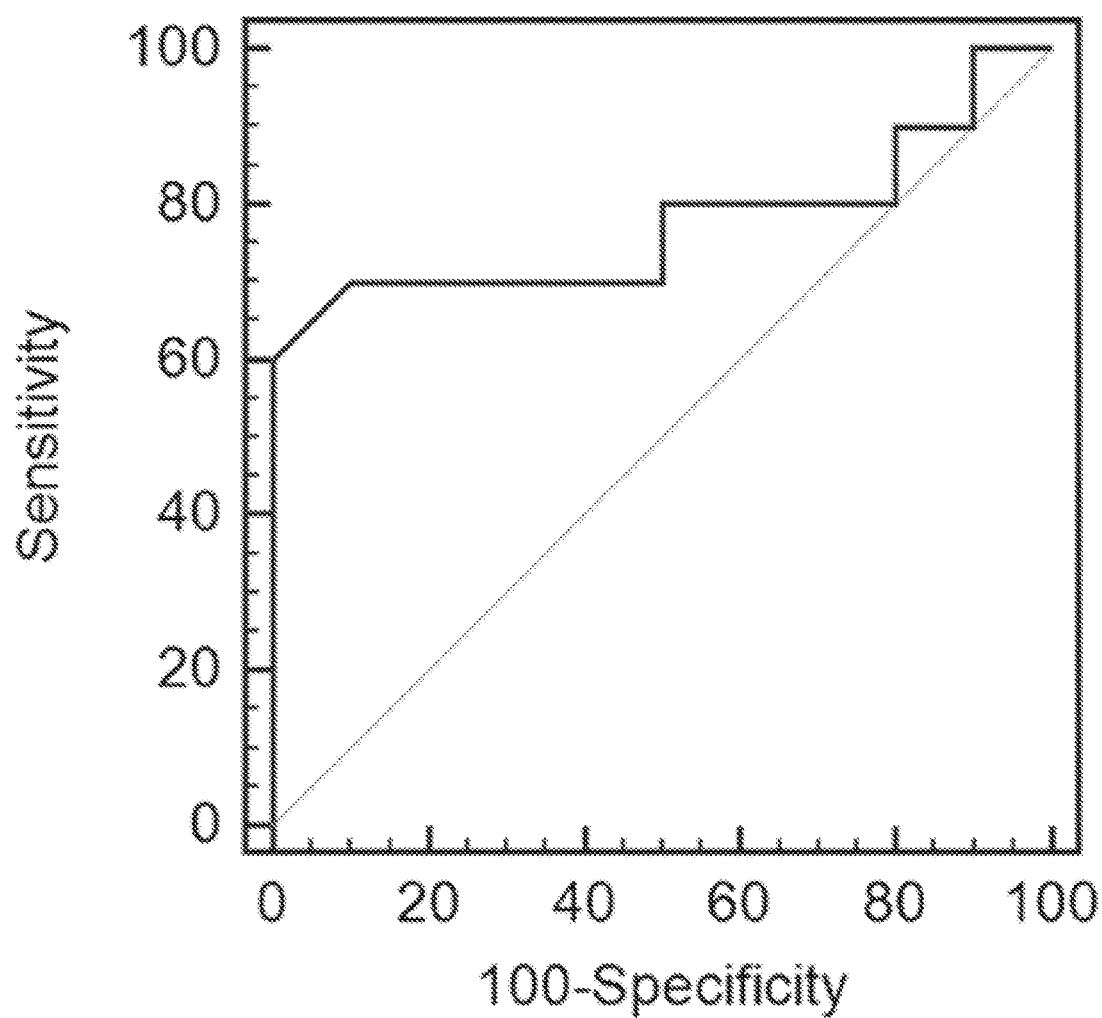
FIG. 42 illustrates a receiver operating characteristics (ROC) curve for ultrasound thermal strain measurements.

The ROC curve in FIG. 42 was reconstructed to evaluate the capability of US-TSI measurements to distinguish between 10 control and 10 fatty livers. The area under the ROC curve (AUC) was 0.775 with a standard error of 0.116 ($p<0.05$). Using an optimal thermal strain cut-off level of −0.097%, the sensitivity and specificity were 70% and 90%, respectively.

This work demonstrated ex vivo the feasibility of identifying fatty livers using US-TSI. This approach provides a quantitative assessment and can be used as a complementary diagnostic tool to conventional B-mode techniques. The increased fat accumulations, of negative temperature dependent sound speed, in fatty livers slowdown or reverse the sound speed positive dependency of normal water-based liver tissue (ref). In this study, US-TSI was implemented and tested successfully on two different configurations including mid-frequency clinical system and high-frequency small animal systems. No significant difference in strain measurements was observed between the two configurations in fatty ($p=0.637$) and control ($p=0.484$) livers. Most of fatty livers showed slightly negative mean strains instead of positive strains expected in pure fat. This may be due to the application of US-TSI at a relatively low temperature range (21-25° C.) and with liver fat concentration range from 29.4% to 62.8%, where the slope of temperature dependent sound speed can be slightly positive. However, thermal strain was significantly higher in fatty than control livers ($p<0.05$) using a temperature rise of approximately 1.5° C.

US-TSI exhibited 70% sensitivity and 90% specificity with 0.775 AUC. In order to compare US-TSI performance with B-mode techniques, we applied the quantitative B-mode technique described in Web et al. 2009 on the same livers with the gelatin background used as a reference instead of kidney. We measured higher sensitivity of 90% and lower specificity of 80% with a larger AUC (0.900) compared to US-TSI. However, we observed that two livers that were misclassified using the B-mode technique, were correctly classified using US-TSI. This may suggest that the use of hybrid measurements from B-mode and US-TSI shall improve the overall diagnostic accuracy of fatty liver disease.

Figure 41C:
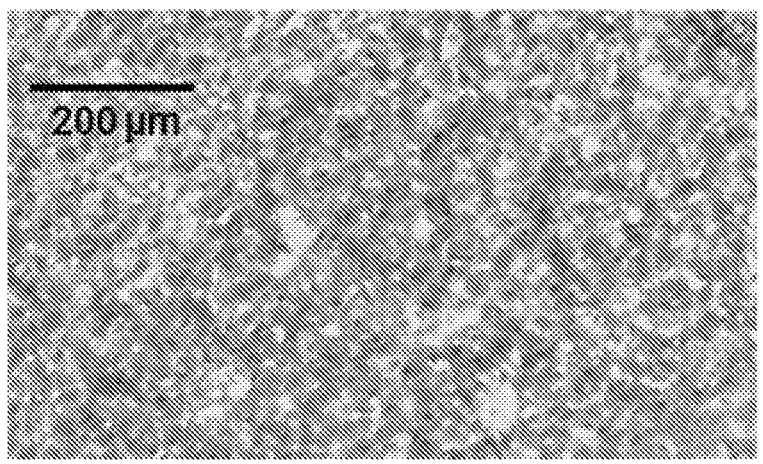
FIG. 41(c) illustrates oil red O histology for a cross-section within the liver.

Although attempts have been made to modify the beamforming of the clinical transducer to perform both imaging and heating, there are still inherent limitations, such as limited heating efficiency and beam width since it was originally designed for conventional US "imaging". Further investigations are required to design a separate heating transducer that can be incorporated with any imaging transducer, and provide compactness and ease of translation. In this effort, a prototype heating transducer was developed and tested with the Vevo2100 US system. Our data showed more efficient heating (~3 times) and uniform pattern for US-TSI (FIGS. 40 and 41). Currently, this high power heating array can deliver total acoustic power of 30 W to produce intensities greater than 15 W/cm2 in a tissue target depth from 20-30 mm. For future clinical translation of this technology, the flexible design of this high power heating array can be adapted to increase the heating depth up to 60 mm.

Safety is an important consideration for the future in vivo application of US-TSI in preclinical or clinical studies. According to the American Institute of Ultrasound in Medicine (AIUM), no significant adverse biological effects were observed due to temperature increases of less than or equal to 2° C. above normal for exposure durations up to 50 hours. Also, when the maximum heat exposure time is limited to 10 s, the maximum allowable safe temperature increase shall increase to 8.5° C. above normal. The peak negative pressure of the US heating pulse used in our study was estimated from experimental measurements to evaluate the mechanical index (MI), which is the peak negative pressure amplitude in MPa divided by the square root of the transmitted frequency in MHz. The clinical system exhibited a peak negative pressure amplitude of −1.27 MPa, while it was −1.40 MPa using the custom heating array. Consequently, the MI was found to be a maximum of 0.75, which is below the FDA maximum allowance (MI <1.9) to avoid adverse biological effects. These in vitro acoustic measurements suggest the safe use of US-TSI, however, an important next step would be to conduct extensive monitoring for these acoustic parameters during in vivo animal studies.

One major challenge for translating this technology into clinics is the physiological motion artifacts due to breathing and cardiac pulsation. These physiological motions in the liver can produce mechanical displacements and corresponding strains that may reach an order of magnitude bigger than those of US-TSI. One possible solution to overcome this problem is to ask patients to hold breathing for few seconds (<5 s) while synchronizing US-TSI frame acquisition with ECG to compensate for cardiac pulsation. Another solution is to adopt time series analysis to separate the linear trend thermal strains from these cyclic mechanical strains.

Example 6—TSI on Human Carotid Plaques

A further example is provided to illustrate the applicability of TSI as a clinical tool to detect lipid contents in human carotid arteries and help assessing plaque vulnerability. The schematic in FIG. 43(a) illustrates an exemplary experimental set-up used for the in vitro testing of the TSI technique using human tissue specimens of CEA. In vitro specimens are collected under Institutional Review Board (IRB) approved by the University of Pittsburgh. Under the IRB approval, cardiovascular surgeons of the university of Pittsburgh medical center (UPMC) provide the arterial specimens. FIG. 43(b) shows an optical image of a typical CEA specimen including the internal carotid artery (ICA), external carotid artery (ECA), and common carotid artery (CCA). Surgeons mark the sites of severe atherosclerosis with stitches that can be used as landmarks during ultrasound scanning besides morphological matching that are required for histology comparison. Upon receiving fresh specimens, right after surgery, they were embedded in gelatin blocks made of porcine skin and 1% cellulose to provide scattering particles mimicking those of human tissue around CEA specimen. These particles generate ultrasound speckles around specimens to assure the effectiveness of the speckle tracking algorithm in measuring temporal displacements. Specimens were then placed in a water tank for ultrasound B-mode and TSI scanning using a 5-14 MHz linear array transducer attached to an ultrasound machine with research capabilities (SonixTouch, Ultrasonix Medical Corp., Richmond, BC, Canada). Ultrasound frame acquisition was initialized by a TTL trigger corresponds to the QRS of a simulated ECG signal via using an arbitrary function generator (33250A, Agilent Technologies, CA). The ultrasound transducer was attached to a 3D positioning system, and ultrasound scanning was performed for different sections 1-2 mm of the short and long axes of CEA specimens. After completing the acquisition process, the data is transferred to Matlab 7.12.0 (The MathWorks, Inc., Natick, Mass., USA) for post processing and TSI reconstruction. After completing the ultrasound procedures, vessels were cleaned, and then sent for histology at the University of Pittsburgh. Landmarks and morphology description including simple drawings were taken along with the specimens to the histology staff for recommended orientation while sectioning. Samples were frozen in aqueous media, cryosectioned and then stained with Oil-Red-O to detect and quantify lipids. Cross-sections from histology were approximately compared with both B-mode and TSI measurements.

Figure 44:
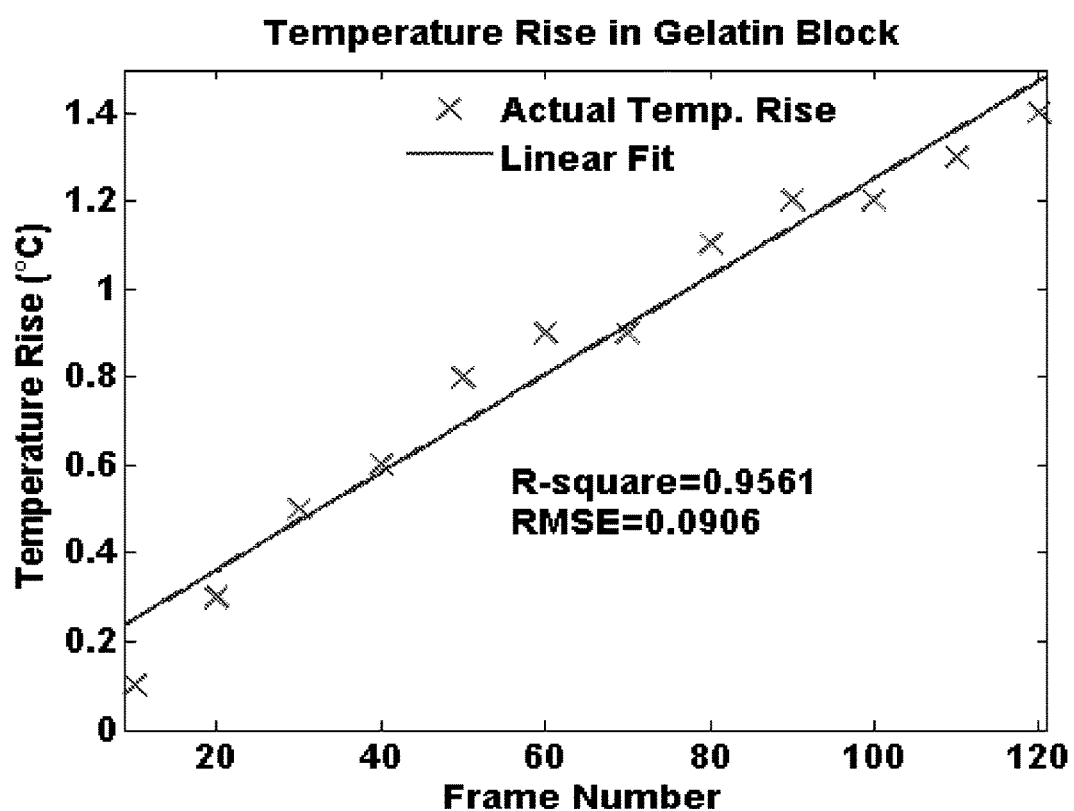
FIG. 44 shows a temperature rise in gelatin as frame number increases.

TSI was applied on fresh CEA specimens with AP embedded in gelatin block on same day of surgery. The temperature rise imposed by TSI heating sequence was monitored in gelatin using a temperature probe attached to a multimeter (Fluke 116, Fluke Corporation, WA). The temperature probe was inserted in gelatin 3 mm above the heating focal depth where CEA specimens are approximately placed. FIG. 44 shows the temperature rise in gelatin as frame number increases. Data was fitted into a linear model with R-square of 0.96 and root mean square error (RMSE) of 0.09° C. Note that a period of 300 ms between successive frames was used. A strong linear correlation was observed between temperature rise and frame number with an average rate of temperature increase 0.01° C. per frame. TSI was applied in vitro to detect lipids in human CEA specimens with AP, and multiple longitudinal and radial scans were acquired.

Figure 45:
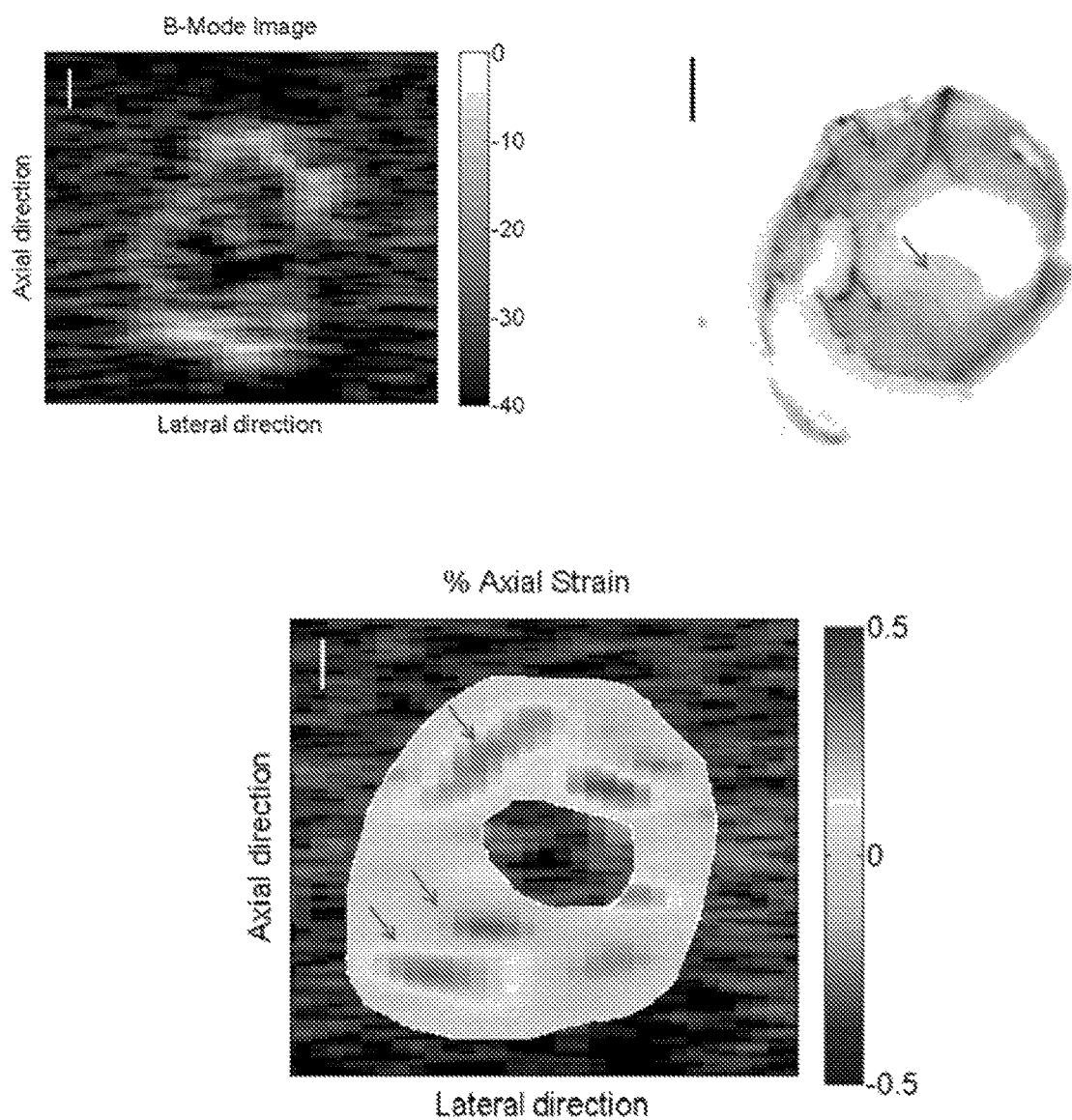
FIG. 45 illustrates in vitro images for a cross-section of the internal carotid artery of a patient diagnosed with atherosclerosis after a carotid endarterectomy.

FIG. 45 illustrates in vitro images for a cross-section of the internal carotid artery of a patient diagnosed with atherosclerosis (62-old female) after carotid endarterectomy. (a) B-mode ultrasound image for the cross-section, (b) approximately matched histology for the cross-section stained with Oil-Red-O, and (c) corresponding thermal strain image (TSI). Red and blue arrows superimposed to highlight lesions of positive strain (lipid based), and negative strain (water-based), respectively. Histology shows large lesions of high lipid content within the plaque. The TSI image shows a good agreement with histology, where large lesions of positive strains that correspond to lipid are noted. (Bar=2 mm).

The B-mode ultrasound image illustrated in FIG. 45(a) for a across-section within the ICA of a patient diagnosed with atherosclerosis includes an atherosclerotic legion marked by the cardiovascular surgeon using surgical stitch. The image indicates a luminal stenosis that was confirmed via the histology of an approximately cross-section (FIG. 45(b)). Oil-Red-O was used to stain histology slides and impose a red color into lesions of fat deposits within the vessel's cross-section. TSI image for the same cross-section is shown in FIG. 45(c), where a good match with histology in detecting lipid can be seen. Red and blue arrows were superimposed to highlight lesions of positive strain (lipid-based), and negative strain (water-based), respectively. Both histology and TSI show large lesions of high lipid content within the plaque.

In order to demonstrate the repeatability of TSI in detecting lipid contents within the same AP, similar findings were found in FIG. 46 for a cross-section 1 mm apart from the one in FIG. 45. FIG. 46 illustrates (a) B-mode ultrasound image for the cross-section, (b) approximately matched histology for the cross-section stained with Oil-Red-O, and (c) corresponding thermal strain image (TSI). Red and blue arrows superimposed to highlight lesions of positive strain (lipid based), and negative strain (water-based), respectively. In this figure, the B-mode image showed luminal stenosis, and good match was found between the histology and TSI in detecting lipid-based and water-based tissues.

Figure 47:
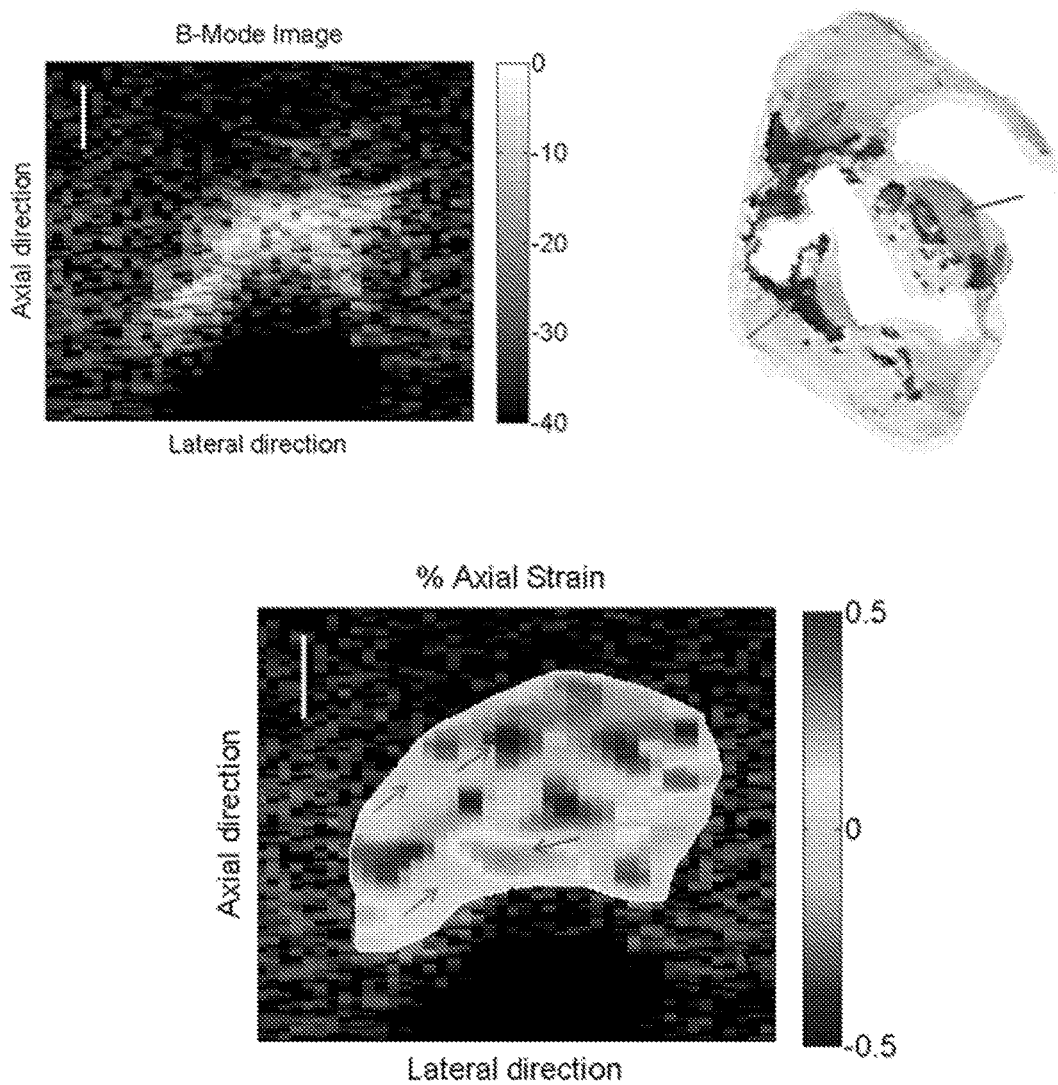
FIG. 47 shows the results of another in vitro study to image an atherosclerotic cross-section.

FIG. 47 shows the results of another in vitro study to image an atherosclerotic cross-section within the ICA of a patient diagnosed with atherosclerosis after CEA surgery. The B-mode ultrasound image and the approximately matched histology cross-section stained with Oil-Red-O are shown in FIGS. 47(a) and (b), respectively. Histology cross-section shows mostly calcified lesions within the AP in dark blue color and few lipid-rich lesions in red. FIG. 47(c) describes the corresponding TSI image with the red, blue, and green arrows superimposed to highlight lesions of positive strain (lipid based), negative strain (water-based), and near-zero strain, respectively. TSI shows a good agreement with histology, where small lesions of positive strains corresponding to lipids were observed and lesions of negative strains were mostly observed. Based on different studies, a high correlation was observed between lesions of very low negative (near-zero) in TSI measurements and calcified lesions from histology (green arrows).

Figure 48:
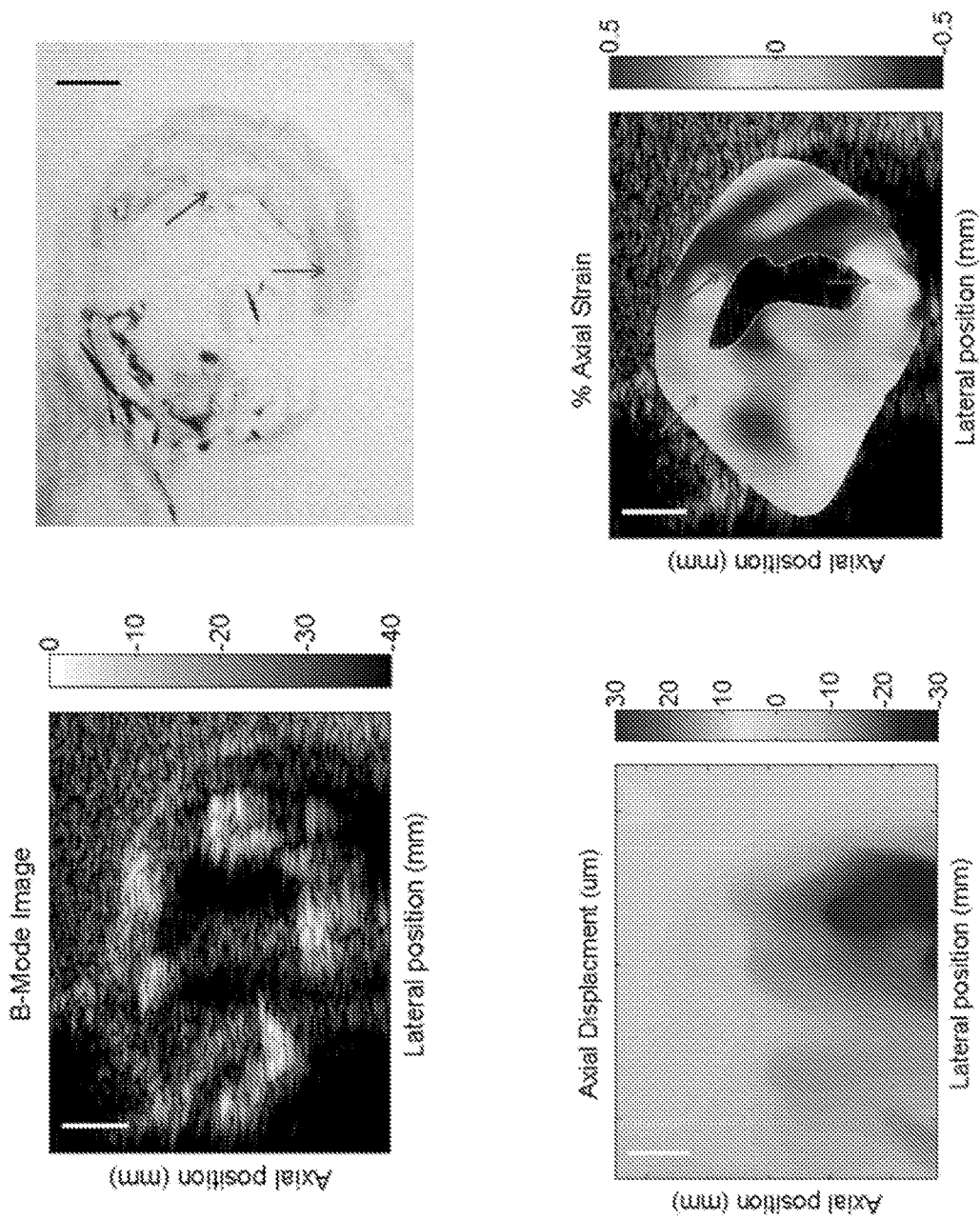
FIG. 48 illustrates the results of testing the thermal array using CEA tissue specimen of a patient diagnosed with atherosclerosis.

A novel transducer in conjunction with high frequency ultrasound imaging system (Vevo2100, VisualSonics, Toronto, Canada) was used to image CEA tissue specimen of a patient diagnosed with atherosclerosis. FIG. 48 illustrates the results of testing the thermal array using CEA tissue specimen of a patient diagnosed with atherosclerosis. The specimen was embedded in gelatin block with ultrasound scatterers. Ultrasound scans for the ICA were acquired using VisualSonics MS250 20 MHz probe attached to the high-resolution ultrasound system (Vevo2100). (a) illustrates B-mode ultrasound image for a cross-section in the ICA, (b) illustrates the approximately matched histology for the cross-section stained with Oil-Red-O, (c) illustrates temporal displacement image of the cross-section due to approximately 1° C. temperature rise (c) corresponding thermal strain image. Red, blue, and green arrows superimposed to highlight lesions of positive strain (lipid based), negative strain (water-based), and near-zero strain, respectively. Histology shows small lesions of low lipid contents, while calcified lesions were mostly observed within the plaque. TSI shows a good agreement with histology.

The new transducer was able to impose approximately 1° C. temperature rise in the sample within few simulated cardiac cycles (3-4). Temporal displacements generated in the same cross-section due to approximately 1° C. temperature rise are measured in FIG. 48(*c*). Corresponding thermal strain image is shown in FIG. 48(*d*), where red, blue, and green arrows superimposed to highlight lesions of positive strain (lipid based), negative strain (water-based), and near-zero strain, respectively. TSI shows good agreement with histology, where small lesions of mild lipid contents and large lesions of water-based and calcified tissues were mostly observed within the plaque.

Example 7—Adaptive Displacement Estimation

As discussed elsewhere herein, ultrasound thermal strain imaging (TSI) utilizes the temperature dependence of the speed of sound to identify lipid and water-based tissues. In soft tissue with temperature changes less than 3° C., TSI typically produces relatively small strains measuring between −0.3-0.6%. This is a result of a gradient in displacement with very small displacements present at the top of the target and larger displacements present at the bottom. The gradient in displacement can span two orders of magnitude.

Two-dimensional normalized cross-correlation with zero-phase crossing (2DCC) has been used to estimate displacements created by TSI. 2DCC has been shown to perform better for larger strains up to 1-2%, but less effectively for very small displacement estimates near the top of targets. Phase-shift estimators such as Kasai's autocorrelator can provide small displacement estimation, however, they are limited to displacement estimates $<\lambda/2$. TSI typically generates displacements greater than $\lambda/2$ near the bottom of an inclusion. As disclosed herein, an adaptive displacement estimation algorithm incorporating both 2DCC and Kasai can provide improved displacement estimates throughout the entire target region.

Methods

A gelatin phantom with a 6 mm diameter cylindrical rubber inclusion was constructed. The phantom was simultaneously imaged and heated using VisualSonics MS250 (fc=21 MHz) with a custom-designed heating transducer designed to provide a broad heating beam. Displacement was estimated on raw data using both 2DST and Kasai. All other signal processing steps were the same.

If the problem is posed as $\Pr(\mu_{true} = \mu_{est} | 2DCC \text{ or Kasai})$, then $\mu_{est}$ is a sufficient statistic for this decision and can be compared to a displacement threshold, $\gamma$, to determine most accurate estimate at a given location.

Results and Discussion

Figure 49:
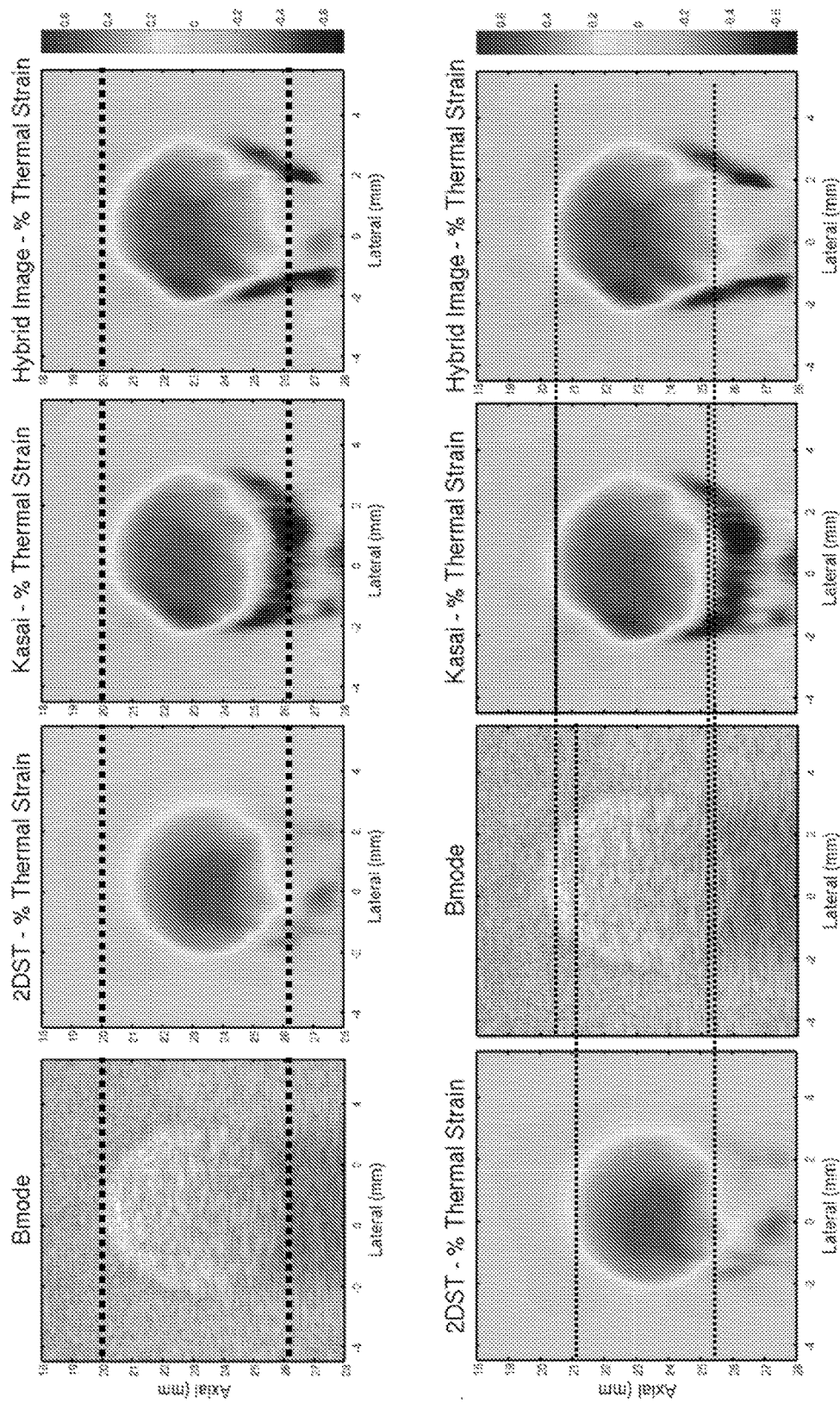
FIG. 49 is a comparison of a B-mode image with TS images generated using 2DCC, Kasai, and a novel combined algorithm.

FIG. 49 is a comparison of a B-mode image with TS images generated using 2DCC, Kasai, and a novel combined algorithm. 2DCC misses the top 0.5 mm of the lesion whereas Kasai misses the bottom 1 mm of the lesion. $\gamma$ was determined empirically from phantom data to be 9.2 μm and a combined estimate was generated, identifying the top and bottom of the lesion with accuracy to within 0.1 mm at the top and within 0.5 mm at the bottom as compared to the B-mode image.

Phase-shift estimators tend to correctly estimate small displacement and 2DCC correctly estimates large displacement. For low SNR and displacement <30 μm, normalized cross-correlation can be more biased than Kasai, while above this threshold, Kasai can be more biased. The adaptive estimation disclosed herein combines these two estimators and can be used to reconstruct TSI more accurately than either approach individually.

Additional Discussion

Figure 50:
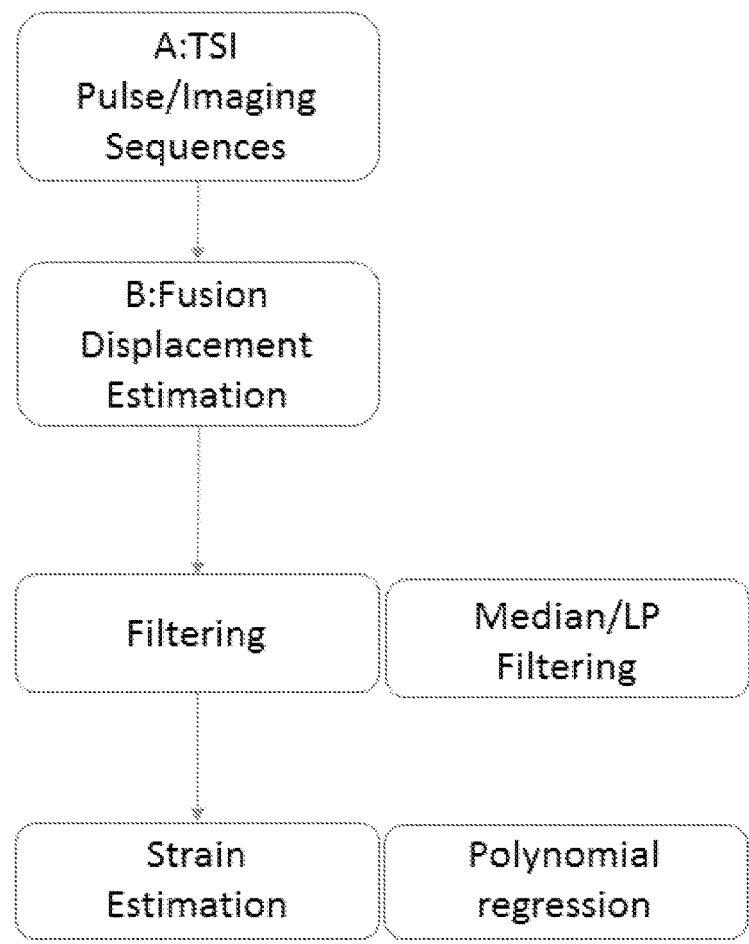
FIG. 50 illustrates an exemplary flow chart for TSI pluse/imaging sequences and strain estimation.

FIG. 50 illustrates an exemplary flow chart for TSI pluse/imaging sequences and strain estimation. As shown in FIG. 50, after pulse/imaging sequences, B:fusion displacement estimation can be performed. Filtering and strain estimation can also be performed as shown in FIG. 50 and as discussed elsewhere herein.

Figure 51:
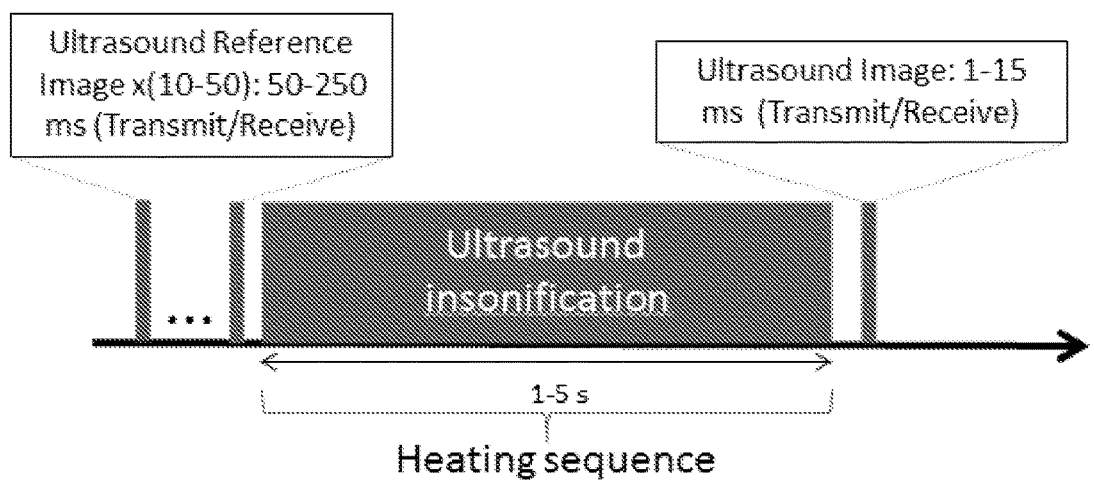
FIG. 51 illustrates an exemplary heating sequence for performing some of the embodiments disclosed herein.

FIG. 51 illustrates an exemplary heating sequence for performing some of the embodiments disclosed herein. For example, as shown in FIG. 51, one or more ultrasound reference images can be obtained, a heating sequence performed (e.g., 1-5 seconds in duration) and one or more additional ultrasound images obtained after the heating sequence.

Figure 52:
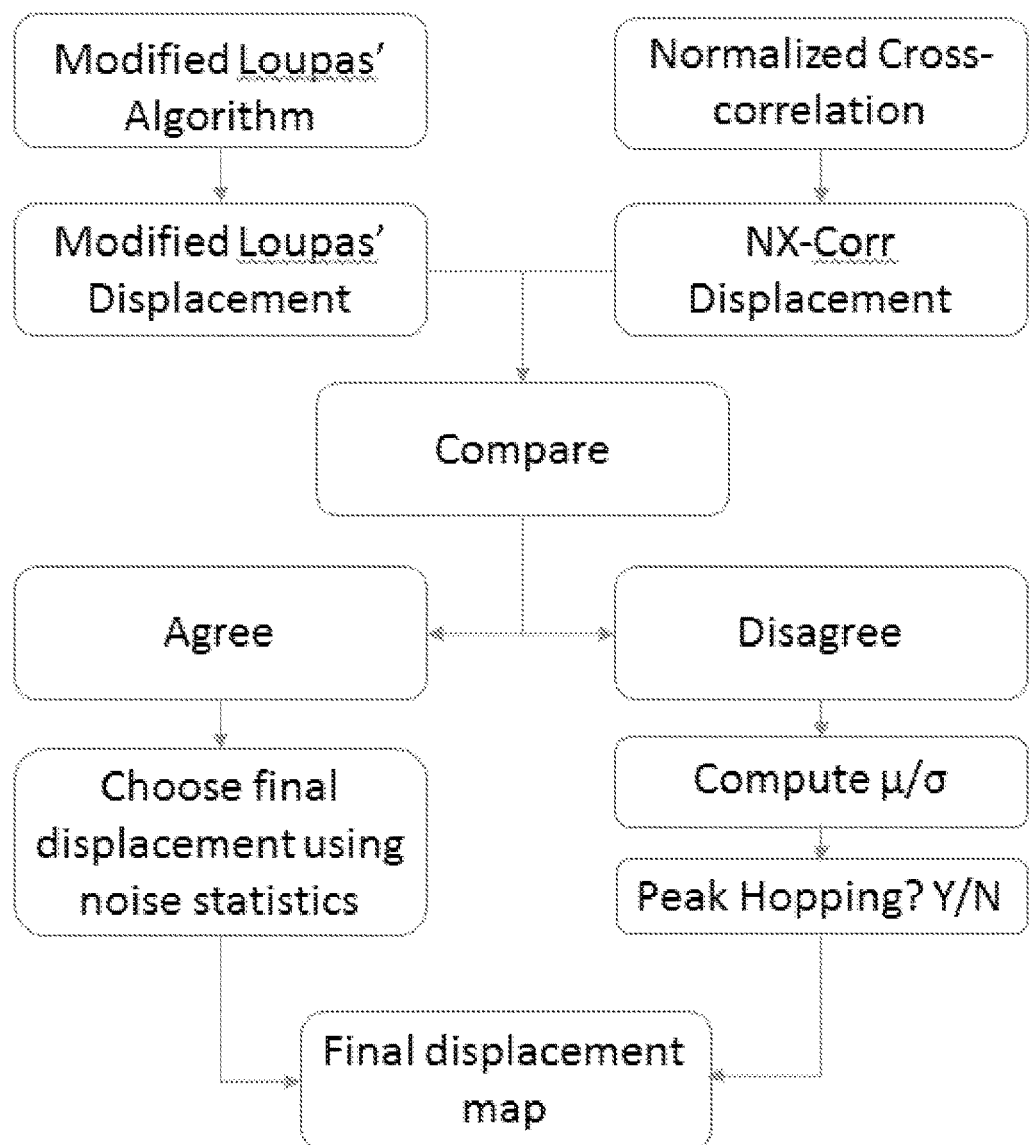
FIG. 52 illustrates an exemplary method of performing B:fusion displacement estimation.

FIG. 52 illustrates an exemplary method of performing B:fusion displacement estimation. Loupas' algorithm typically estimates small displacements well, but can only track displacements less than one quarter wavelength in magnitude. Beyond this point it experiences "phase-wrapping" error which results in a gradual loss of accuracy. Normalized cross-correlation (XCorr) estimates larger displacements better than Loupas' algorithm. However, it can experience large "peak hopping" errors which results in a sharp, large change in local displacement.

When the two algorithms are in close agreement, the overall error can be minimized by choosing the algorithm that performs better. The choice of which algorithm performs better can be based on the displacement magnitude and the noise properties of the B-mode image (e.g. electronic and speckle signal-to-noise ratios). When the two algorithms disagree, this is because either "peak hopping" or "phase-wrapping" errors have caused large discrepancies between the estimates. In real-imaging scenarios, we expect the trend in displacement to change relatively smoothly. As a result, $$\frac{\mu}{\sigma},$$

the value of the mena, μ, divided by the standard deviation, σ, should be relatively large over a small spatial region. Small values suggest that the XCorr estimate has been corrupted by peak hopping errors and that the Loupas estimate should be used. Large values suggest that "phase-wrapping" has occurred and that normalized cross-correlation is the better estimate.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for quantifying an amount of fat contained in a liver of a living human subject in vivo, the method comprising:
    imaging thermal strain of a target area of the liver of the subject using an ultrasound scanner to obtain a first thermal strain imaging sequence at a first temperature and a second thermal strain imaging sequence at a second temperature, the first and second thermal strain imaging sequences being obtained while the subject is holding their breath to reduce breathing-induced strain artifacts;
    increasing the temperature of the target area in the subject from the first temperature to the second temperature; and
    generating and displaying a thermal strain map to quantify the amount of fat in the target area based on the thermal strain imaging by differentiating between fat-based tissue and water-based tissue based on the displayed thermal strain map,
    wherein the first temperature is a normal body temperature of the target area for the subject and the second temperature is less than three degrees Celsius higher than the first temperature, and
    wherein the act of increasing the temperature of a target area of a liver in a subject comprises applying heat to the target area of the liver from an external heating device in a controlled manner until the target area is at the second temperature.

2. The method of claim 1, wherein the thermal strain imaging comprises high-resolution, phase-sensitive speckle tracking.

3. The method of claim 1, wherein the increase in temperature from the first temperature to the second temperature is less than two degrees Celsius.

4. The method of claim 1, wherein the external heating device is a near infrared heating source that is coupled to the ultrasound scanner.

5. The method of claim 1, wherein the external heating device is a near infrared heating source that is separate from the ultrasound scanner.

6. The method of claim 1, wherein the heating of the target area comprises:
    directing a second ultrasound device at the target area to heat the target area.

7. The method of claim 1, wherein the first and second thermal strain imaging sequences are obtained in less than 10 seconds.

8. The method of claim 7, wherein the act of increasing the temperature of the target area is interleaved between the imaging of the target area to obtain the first thermal strain imaging sequence and the imaging of the target area to obtain the second thermal strain image sequence.

9. The method of claim 1, further comprising obtaining a third thermal strain imaging sequence at a temperature between the first and second temperature, wherein the first, second, and third thermal strain imaging sequences are obtained in less than 10 seconds.

10. The method of claim 1, wherein the first and second thermal strain imaging sequences are obtained in about 4 seconds.

11. The method of claim 1, wherein the total heat delivered to the target area is less than 8 W/kg over a period of less than 5 minutes.

12. The method of claim 1, wherein the ultrasound scanner is the external heating device.

13. The method of claim 1, wherein the second temperature is less than two degrees Celsius higher than the first temperature.

14. The method of claim 1, further comprising obtaining a third thermal strain imaging sequence at a temperature between the first and second temperature, wherein the first, second, and third thermal strain imaging sequences are obtained in less than 10 seconds.

15. A system for identifying, in vivo, fat-containing tissue in a liver of a living subject, the system comprising:
    an ultrasound imaging device for providing high-resolution, phase-sensitive speckle tracking;
    a temperature variation device configured to increase and modulate the temperature of a target area of the liver of the subject from a first temperature to a second temperature while the ultrasound imaging device is in operation, the first temperature being a normal liver temperature for the subject and the second temperature being less than three degrees Celsius higher than the first temperature; and
    a display configured to receiving imaging information from the ultrasound imaging to display a thermal strain map to quantify the amount of fat in the target area,
    wherein the temperature variation device comprises an external heating device, the external heating device being a near infrared heating source that is configured to apply heat in a controlled manner to reach the second temperature without exceeding the second temperature.

16. The system of claim 15, wherein the external heating device is coupled to and integrated with the ultrasound imaging device.

17. The system of claim 15, wherein the external heating device comprises a second ultrasound source.

* * * * *